US010485865B2

(12) United States Patent
Voss

(10) Patent No.: US 10,485,865 B2
(45) Date of Patent: Nov. 26, 2019

(54) METHOD AND COMPOSITIONS

(71) Applicant: GlaxoSmithKline Biologicals, S.A., Rixensart (BE)

(72) Inventor: Gerald Hermann Voss, Rixensart (BE)

(73) Assignee: GlaxoSmithKline Biologicals SA (BE)

( * ) Notice: Subject to any disclaimer, the term of this patent is extended or adjusted under 35 U.S.C. 154(b) by 36 days.

(21) Appl. No.: 15/242,904

(22) Filed: Aug. 22, 2016

(65) Prior Publication Data

US 2017/0196960 A1 Jul. 13, 2017

Related U.S. Application Data

(63) Continuation of application No. 13/744,867, filed on Jan. 18, 2013, now Pat. No. 9,717,788, which is a continuation of application No. 12/529,062, filed as application No. PCT/EP2008/052448 on Feb. 28, 2008, now abandoned.

(60) Provisional application No. 60/892,714, filed on Mar. 2, 2007.

(51) Int. Cl.

| | |
|---|---|
| ***A61K 39/02*** | (2006.01) |
| ***A61K 39/04*** | (2006.01) |
| ***A61K 39/00*** | (2006.01) |
| ***A61K 39/21*** | (2006.01) |
| ***A61K 39/015*** | (2006.01) |
| ***A61K 39/12*** | (2006.01) |
| ***C12N 7/00*** | (2006.01) |

(52) U.S. Cl.

CPC ............ *A61K 39/21* (2013.01); *A61K 39/015* (2013.01); *A61K 39/04* (2013.01); *A61K 39/12* (2013.01); *C12N 7/00* (2013.01); *A61K 2039/5254* (2013.01); *A61K 2039/5256* (2013.01); *A61K 2039/54* (2013.01); *A61K 2039/545* (2013.01); *A61K 2039/55566* (2013.01); *A61K 2039/55572* (2013.01); *A61K 2039/55577* (2013.01); *C12N 2710/10043* (2013.01); *C12N 2710/10334* (2013.01); *C12N 2710/10343* (2013.01); *C12N 2710/10371* (2013.01); *C12N 2740/16034* (2013.01); *C12N 2740/16134* (2013.01); *C12N 2740/16234* (2013.01); *C12N 2740/16334* (2013.01); *C12N 2799/022* (2013.01); *C12N 2799/04* (2013.01); *Y02A 50/412* (2018.01)

(58) Field of Classification Search

CPC ........ A61K 39/00; A61K 39/12; A61K 39/02; A61K 39/04

USPC ......... 424/184.1, 185.1, 190.1, 204.1, 234.1, 424/248.1, 278.1

See application file for complete search history.

(56) References Cited

U.S. PATENT DOCUMENTS

| | | | |
|---|---|---|---|
| 7,531,182 | B2 | 5/2009 | King et al. |
| 2006/0240039 | A1 | 10/2006 | Hill et al. |
| 2007/0054395 | A1 | 3/2007 | Emini et al. |
| 2008/0131461 | A1 | 6/2008 | Pau et al. |
| 2008/0233083 | A1 | 9/2008 | Ansari et al. |
| 2009/0208515 | A1 | 8/2009 | Ertl et al. |
| 2010/0055166 | A1 | 3/2010 | Voss |
| 2010/0209451 | A1 | 8/2010 | Clarke |
| 2011/0236468 | A1 | 9/2011 | Lorin |
| 2011/0268762 | A1 | 11/2011 | Toro et al. |
| 2012/0058138 | A1 | 3/2012 | Draper et al. |

FOREIGN PATENT DOCUMENTS

| | | | |
|---|---|---|---|
| CA | 2737761 | A1 | 3/2010 |
| EP | 2324050 | | 5/2011 |
| GB | 2452958 | A | 3/2009 |
| WO | 2001/054719 | A2 | 8/2001 |
| WO | 2002/022080 | A2 | 3/2002 |
| WO | 2003/011334 | A1 | 2/2003 |
| WO | 2004/110482 | A1 | 12/2004 |
| WO | 2006/013106 | A2 | 2/2006 |
| WO | 2006/120034 | A1 | 11/2006 |
| WO | 2006117240 | A2 | 11/2006 |
| WO | 2007/003384 | A1 | 1/2007 |
| WO | 2008/107370 | A1 | 9/2008 |
| WO | 2010/023260 | A1 | 3/2010 |

OTHER PUBLICATIONS

Rollman, et al. , "Evaluation of immunogenicity and efficacy of combined DNA and adjuvanted protein vaccination in a human immunodeficiency virus type 1/murine leukemia virus pseudotype challenge model." Vaccine; 2007; pp. 2145-2154; vol. 25 (11).

Koopman, et al. , "Immune-response profiles induced by human immunodeficiency virus type 1 vaccine DNA, protein or mixed-modality immunization: increased protection from pathogenic simian-human immunodeficiency virus viraemia with protein/DNA combination." Journal of General Virology; 2008; pp. 540-553; vol. 89.

(Continued)

*Primary Examiner* — Rodney P Swartz

(74) *Attorney, Agent, or Firm* — Joseph J. Schuller

(57) ABSTRACT

The present invention relates to, inter alia, a method of raising an immune response against a pathogen which comprises administering (i) one or more first immunogenic polypeptides derived from said pathogen; (ii) one or more adenoviral vectors comprising one or more heterologous polynucleotides encoding one or more second immunogenic polypeptides derived from said pathogen; and (iii) an adjuvant; wherein the one or more first immunogenic polypeptides, the one or more adenoviral vectors and the adjuvant are administered concomitantly. The invention also relates to vaccines, pharmaceutical compositions, kits and uses employing said polypeptides, adenoviral vectors and adjuvants.

7 Claims, 31 Drawing Sheets

Specification includes a Sequence Listing.

(56) References Cited

OTHER PUBLICATIONS

Ganne, et al., "Enhancement of the efficacy of a replication-defective adenovirus-vectored vaccine by the addition of oil adjuvants." Vaccine; 1994; pp. 1190-1196; vol. 12(13).
Jones, et al., "Protection of Aotus Monkeys by Plasmodium falciparum EBA-175 Region II DNA Prime-Protein Boost Immunization Regimen" The Journal of Infectious Diseases; 2001; pp. 303-312; vol. 183.
Steel, J. C., et al., "Microsphere-liposome complexes protect adenoviral vectors from neutralising antibody without losses in transfection efficiency, in-vitro." Journal of Pharmacy and Pharmacology; 2004; pp. 1371-1378; vol. 56.

Anti-F4 serology

METHOD AND COMPOSITIONS

FIELD OF THE INVENTION

This invention relates to novel vaccine compositions and their use in the stimulation of immune responses in mammals, especially humans, and in particular for the prevention and treatment of infection by pathogens. In particular it relates to compositions capable of inducing CD4+ and CD8+ T-cell responses as well as antibody responses in subjects without recourse to complex prime-boost schedules.

BACKGROUND TO THE INVENTION

Inactivated whole organisms have been used in successful vaccination since the late nineteenth century. In more recent times, vaccines involving the administration of extracts, subunits, toxoids and capsular polysaccharides have been employed. Since genetic engineering techniques have been available, the use of recombinant proteins has been a favoured strategy, obviating many of the risks associated with use of purified proteins from natural sources.

Early vaccine approaches were based on the administration of proteins which stimulated some aspect of the immune response in vivo. Subsequently it was appreciated that immune responses could also be raised by administration of DNA which could be transcribed and translated by the host into an immunogenic protein.

The mammalian immune response has two key components: the humoral response and the cell-mediated response. The humoral response involves the generation of circulating antibodies which will bind to the antigen to which they are specific, thereby neutralising the antigen and favouring its subsequent clearance by a process involving other cells that are either cytotoxic or phagocytic. B-cells are responsible for generating antibodies (plasma B cells), as well as holding immunological humoral memory (memory B-cells), i.e. the ability to recognise an antigen some years after first exposure to it eg through vaccination. The cell mediated response involves the interplay of numerous different types of cells, among which are the T cells. T-cells are divided into a number of different subsets, mainly the CD4+ and CD8+ T cells.

Antigen-presenting cells (APC) such as macrophages and dendritic cells act as sentinels of the immune system, screening the body for foreign antigens. When extracellular foreign antigens are detected by APC, these antigens are phagocytosed (engulfed) inside the APC where they will be processed into smaller peptides. These peptides are subsequently presented on major histocompatibility complex class II (MHC II) molecules at the surface of the APC where they can be recognised by antigen-specific T lymphocytes expressing the CD4 surface molecules (CD4+ T cells). When CD4+ T cells recognise the antigen to which they are specific on MHCII molecules in the presence of additional adequate co-stimulatory signals, they become activated and secrete an array of cytokines that subsequently activate the other arms of the immune system. In general, CD4+ T cells are classified into T helper 1 (Th1) or T helper 2 (Th2) subsets depending on the type of response they generate following antigen recognition. Upon recognition of a peptide-MHC II complex, Th1 CD4+ T cells secrete interleukins and cytokines such as interferon gamma thereby activating macrophages to release toxic chemicals such as nitric oxide and reactive oxygen/nitrogen species. IL-2 and TNF-alpha are also commonly categorized as Th1 cytokines. In contrast, Th2 CD4+ T cells generally secrete interleukins such as IL-4, IL-5 or IL-13.

Other functions of the T helper CD4+ T cells include providing help to activate B cells to produce and release antibodies. They can also participate to the activation of antigen-specific CD8+ T cells, the other major T cell subset beside CD4+ T cells.

CD8+ T cells recognize the peptide to which they are specific when it is presented on the surface of a host cell by major histocompatibility class I (MHC I) molecules in the presence of appropriate costimulatory signals. In order to be presented on MHC I molecules, a foreign antigen need to directly access the inside of the cell (the cytosol or nucleus) such as it is the case when a virus or intracellular bacteria directly penetrate a host cell or after DNA vaccination. Inside the cell, the antigen is processed into small peptides that will be loaded onto MHC I molecules that are redirected to the surface of the cell. Upon activation CD8+ T cells secrete an array of cytokines such as interferon gamma that activates macrophages and other cells. In particular, a subset of these CD8+ T cells secretes lytic and cytotoxic molecules (e.g. granzyme, perforin) upon activation. Such CD8+ T cells are referred to as cytotoxic T cells.

More recently, an alternative pathway of antigen presentation involving the loading of extracellular antigens or fragments thereof onto MHCI complexes has been described and called "cross-presentation".

The nature of the T-cell response is also influenced by the composition of the adjuvant used in a vaccine. For instance, adjuvants containing MPL & QS21 have been shown to activate Th1 CD4+ T cells to secrete IFN-gamma (Stewart et al. Vaccine. 2006, 24 (42-43):6483-92).

Whereas adjuvants are well known to have value in enhancing immune responses to protein antigens, they have not generally been used in conjunction with DNA or DNA-based vector vaccination. There are several hypotheses as to why adjuvants have not been used in conjunction with DNA-vector based vaccines. Indeed, interferences between the adjuvant and the vector may have an impact on their stability. In addition, one might expect that adding an adjuvant to an attenuated vector could increase the reactogenicity induced by such product. Finally, increasing the immunogenicity of a DNA-vector based vaccine may lead to an enhanced neutralizing immune response against the vector itself, thereby precluding any boosting effect of subsequent injections of the same vector-based vaccine. In fact, in a vaccination protocol directed towards protection against *P. falciparum* infection, Jones et al (2001, J Infect Diseases 183, 303-312) have reported an adverse outcome after combining DNA, recombinant protein and adjuvant as a boosting composition following a prime by DNA. Indeed, the levels of parasitemia were significantly lower in a group in which the boosting composition contained protein and adjuvant only. It was concluded that use of the combination of DNA, recombinant protein and adjuvant in this protocol adversely affected the outcome on parasitemia as well as antibody responses.

On the other hand, there has been a report of enhancement of the efficacy of an adjuvanted DNA-based vector vaccine (Ganne et al. Vaccine (1994) 12(13) 1190-1196). In particular, the enhanced efficacy of a replication-defective adenovirus-vectored vaccine by the addition of oil adjuvants was correlated with higher antibody levels but the impact on CD4 and CD8 T cell responses was not reported.

The use of an apathogenic virus as an adjuvant has been disclosed in WO2007/016715. It was not mentioned that said virus could contain any heterologous polynucleotide.

It is generally thought that stimulation of both CD4+ and CD8+ cells are needed for optimal protective immunity, especially in certain diseases such as HIV infection/AIDS. In order to induce an optimal immune response either prophylactically or therapeutically, stimulation of both CD4+ and CD8+ cells is desirable. This is one of the main goal of "prime-boost" vaccination strategies in which the alternate administration of protein-based vaccines (inducing mostly CD4+ T cells) with DNA-vector based vaccines, i.e. naked DNA, viral vectors or intracellular bacterial vectors such as *listeria*, (inducing mostly CD8+ T cells) or vice versa most likely activates both CD4+ and CD8+ T cell responses.

However, although prime-boost vaccine strategies may generally give rise to a greater or more balanced response, the requirement to vaccinate on more than one occasion and certainly on more than two occasions can be burdensome or even unviable, especially in mass immunization programs for the developing world.

Furthermore, as already mentioned above, it is often not possible to boost the viral vector component because of immunity that may have been raised against the vector itself.

Thus the objects of the invention include one or more of the following: (a) to provide a complete vaccination protocol and a vaccine composition which stimulates the production of CD4+ and/or CD8+ cells and/or antibodies and in particular which obviates or mitigates the need for repeated immunizations; (b) to provide a vaccination protocol and a vaccine composition which better stimulates production of CD4+ cells and/or CD8+ cells and/or antibodies relative to vaccine compositions containing an immunogenic polypeptide alone or a polynucleotide alone or relative to a conventional prime-boost protocol involving separate administration of immunogenic polypeptide and polynucleotide; (c) to provide a vaccine composition which stimulates or better stimulates Th1 responses; (d) to provide a vaccine composition and vaccination protocol in which required doses of components, especially viral vectors, are minimised; and (e) more generally to provide a useful vaccine composition and vaccination protocol for treatment or prevention of diseases caused by pathogens. By "better stimulates" is meant that the intensity and/or persistence of the response is enhanced.

SUMMARY OF THE INVENTION

Thus according to the invention there is provided a method of raising an immune response against a pathogen which comprises administering (i) one or more first immunogenic polypeptides derived from said pathogen; (ii) one or more adenoviral vectors comprising one or more heterologous polynucleotides encoding one or more second immunogenic polypeptides derived from said pathogen; and (iii) an adjuvant; wherein the one or more first immunogenic polypeptides, the one or more adenoviral vectors and the adjuvant are administered concomitantly.

According to a specific aspect of the invention there is provided a vaccine composition comprising (i) one or more first immunogenic polypeptides derived from a pathogen; (ii) one or more adenoviral vectors comprising one or more heterologous polynucleotide encoding one or more second immunogenic polypeptides derived from said pathogen; and (iii) an adjuvant.

There is also provided an immunogenic composition comprising (i) one or more first immunogenic polypeptides derived from a pathogen; (ii) one or more adenoviral vectors comprising one or more heterologous polynucleotides encoding one or more second immunogenic polypeptides derived from said pathogen; and (iii) an adjuvant.

Said vaccines and immunogenic compositions suitably stimulate production of pathogen-specific CD4+ T-cells and/or CD8+ T-cells and/or antibodies.

By "pathogen-specific CD4+ T-cells and/or CD8+ T-cells and/or antibodies" is meant CD4+ T-cells and/or CD8+ T-cells and/or antibodies which specifically recognise the whole pathogen or a part (eg an immunogenic subunit) thereof. By "specifically recognise" is meant that the CD4+ T-cells and/or CD8+ T-cells and/or antibodies recognise in an immunospecific rather than a non-specific manner said pathogen (or part thereof).

There is also provided a method of stimulating an immune response in a mammal which comprises administering to a subject an immunologically effective amount of such a composition.

There is also provided use of such a composition in the manufacture of a medicament for stimulating an immune response in a mammal.

There is also provided such a composition for use in stimulating an immune response in a mammal.

There is also provided a method of stimulating the production of pathogen-specific CD4+ T-cells and/or CD8+ T-cells and/or antibodies in mammals which comprises administering to said mammal (i) one or more first immunogenic polypeptides derived from a pathogen; (ii) one or more adenoviral vectors comprising one or more heterologous polynucleotides encoding one or more second immunogenic polypeptides derived from said pathogen; and (iii) an adjuvant; wherein the one or more first immunogenic polypeptides, the one or more adenoviral vectors and the adjuvant are administered concomitantly, for example by administering an immunologically effective amount of an aforeseaid composition.

There is also provided use of aforesaid compositions in the manufacture of a medicament for stimulating the production of pathogen specific CD4+ and/or CD8+ cells and/or antibodies in mammals.

For example, production of CD4+ T-cells or CD8+ T-cells or antibodies is stimulated. Suitably production of 2 and especially 3 of CD4+ T-cells and/or CD8+ T-cells and/or antibodies is stimulated.

Suitably production of CD8+ T-cells is stimulated. Suitably production of CD4+ and CD8+ T-cells is stimulated. Suitably production of CD4+ and CD8+ T-cells and antibodies is stimulated.

Alternatively suitably production of CD4+ T-cells is stimulated. Suitably production of CD4+ and antibodies is stimulated.

Alternatively suitably production of antibodies is stimulated.

The methods of the invention are suitably intended to provide the steps adequate for a complete method for raising an immune response (although the method may, if desired, be repeated). Therefore suitably the methods do not involve use of a priming dose of any immunogenic polypeptide or polynucleotide (e.g. in the form of a vector such as an adenoviral vector) encoding any immunogenic polypeptide.

For example there is provided a method of raising an immune response against a pathogen which consists of (a) administering (i) one or more first immunogenic polypeptides derived from said pathogen; (ii) one or more adenoviral vectors comprising one or more heterologous polynucleotides encoding one or more second immunogenic polypeptides derived from said pathogen; and (iii) an adjuvant; wherein the one or more immunogenic polypeptide, the one or more adenoviral vector and the adjuvant are administered concomitantly; and (b) optionally repeating the steps of (a).

The steps of the method may be repeated (e.g. repeated once) if a repeat gives rise to an improved immune response. An adequate response, at least as far as a T-cell response is concerned, may be obtained without any need for repetition.

There is also provided a method of raising an immune response against a pathogen which comprises (a) administering (i) one or more first immunogenic polypeptides derived from said pathogen; (ii) one or more adenoviral vectors comprising one or more heterologous polynucleotides encoding one or more second immunogenic polypeptides derived from said pathogen; and (iii) an adjuvant; wherein the one or more first immunogenic polypeptides, the one or more adenoviral vectors and the adjuvant are administered concomitantly; and wherein the method does not involve administering any priming dose of immunogenic polypeptide or polynucleotide encoding immunogenic polypeptide.

There is also provided a kit comprising (i) one or more first immunogenic polypeptides derived from a pathogen; (ii) one or more adenoviral vectors comprising one or more heterologous polynucleotides encoding one or more second immunogenic polypeptides derived from said pathogen; and (iii) an adjuvant; and in particular comprising (i) one or more first immunogenic polypeptides derived from a pathogen and an adjuvant; and (ii) one or more second adenoviral vectors comprising one or more heterologous polynucleotides encoding one or more immunogenic polypeptides derived from said pathogen; for use in a method according to the invention.

Compositions and methods of the invention may be useful for the prevention of infection by pathogens in naïve subjects, or prevention of re-infection in subjects who have previously been infected by pathogen or treatment of subjects who have been infected by pathogen.

BRIEF DESCRIPTION OF THE FIGURES

FIGS. 2A-8 show the results of experiments discussed in Example 1, specifically:

FIGS. 2A, 2B, 3A, 3B: CD4+ and CD8+ T-cell responses in response to restimulation by pools of peptides derived from p24, RT, Nef and p17 following various immunization protocols and at different timepoints;

FIG. 4: antibody responses against F4;

FIGS. 5-8 antibody responses against F4 components p24, RT, p17 and Nef respectively;

FIGS. 10-12 show the results of experiments discussed in Example 3, specifically:

FIG. 10 shows the lymphoproliferative response of rabbit PBMC against peptide pools covering the F4 sequence;

FIG. 11 shows the timecourse of antibody responses against F4;

SUMMARY OF SEQUENCE LISTINGS

Figure 1:
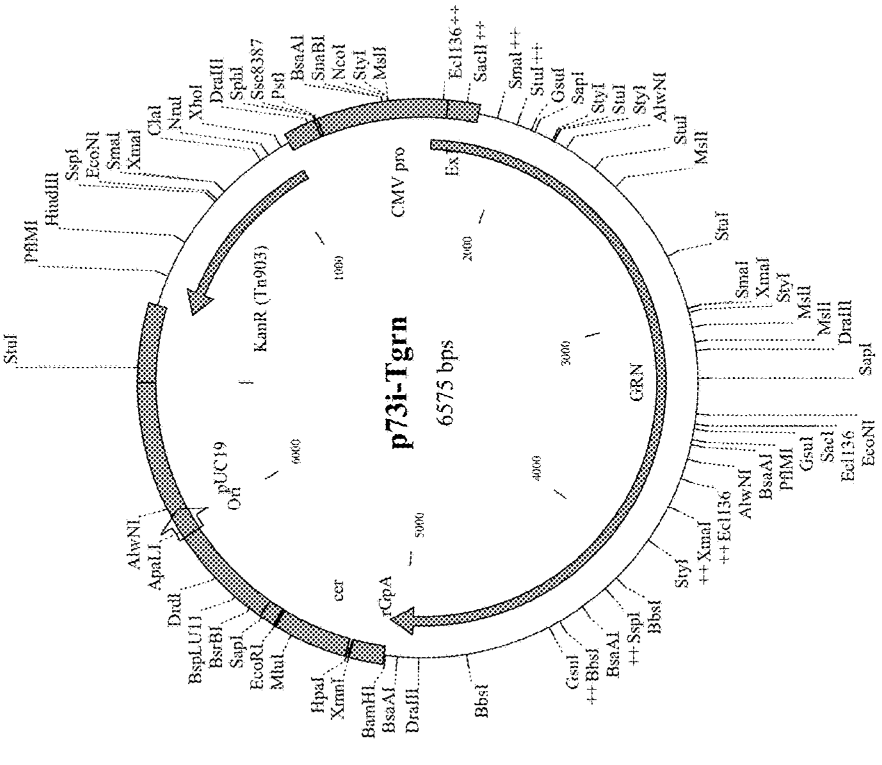
FIG. 1 shows a graphical representation of the construction of plasmid p73i-Tgrn

| Amino acid or polynucleotide description | Sequence Identifier (SEQ ID No) |
|---|---|
| HIV Gag-RT-Nef (“GRN”) (Clade B) (cDNA) | 1 |
| HIV Gag-RT-Nef (“GRN”) (Clade B) (amino acid) | 2 |
| HIV Gag-RT-integrase-Nef (“GRIN”) (Clade A) (cDNA) | 3 |
| HIV Gag-RT-integrase-Nef (“GRIN”) (Clade A) (amino acid) | 4 |
| HIV gp140 (Clade A) (cDNA) | 5 |
| HIV gp140 (Clade A) (amino acid) | 6 |
| HIV gp120 (Clade B) (cDNA) | 7 |
| HIV gp120 (Clade B) (amino acid) | 8 |
| TB antigens fusion protein M72 (cDNA) | 9 |
| TB antigens fusion protein M72 (amino acid) | 10 |
| *P. falciparum* CS protein-derived antigen (cDNA) | 11 |
| *P. falciparum* CS protein-derived antigen (amino acid) | 12 |
| *P. falciparum* CS protein-derived fusion protein “RTS” (cDNA) | 13 |
| *P. falciparum* CS protein-derived fusion protein “RTS” (amino acid) | 14 |
| HIV p24-RT-Nef-p17 (cDNA) | 15 |
| HIV p24-RT-Nef-p17 (amino acid) | 16 |

The above recited sequences may be employed as polypeptides or polynucleotides encoding polypeptides of use in exemplary aspects of the invention. Said polypeptides may consist of or comprise the above mentioned sequences. Initial Met residues are optional. N-terminal His residues (including His residues immediately following an initial Met, as in SEQ ID No 9) are optional or an N-terminal His tag of a different length may be employed (eg typically up to 6 His residues may be employed to facilitate isolation of the protein). Analogue proteins which have significant sequence identity eg greater than 80% eg greater than 90% eg greater than 95% eg greater than 99% sequence identity over the whole length of the reference sequence may be employed, especially when the analogue protein has a similar function and particularly when the analogue protein is similarly immunogenic. For example up to 20 eg up to 10 eg 1-5 substitutions (eg conservative substitutions) may be tolerated. Nucleic acids which differ from those recited above which encode the same proteins, or the aforementioned analogue proteins, may be employed. Sequence identity may be determined by conventional means eg using BLAST. In one specific variant of SEQ ID No 16 that may be mentioned, reside 398 is Ser and not Cys.

DETAILED DESCRIPTION OF THE INVENTION

As used herein the term "concomitantly" means wherein the one or more immunogenic polypeptides, the one or more adenoviral vectors and the adjuvant are administered within a period of no more than 12 hours eg within a period of no more than 1 hour, typically on one occasion e.g. in the course of the same visit to the health professional, for example the one or more immunogenic polypeptides, the one or more adenoviral vectors and the adjuvant are administered sequentially or simultaneously.

As used herein, the term "epitope" refers to an immunogenic amino acid sequence. An epitope may refer to a minimum amino acid sequence of typically 6-8 amino acids which minimum sequence is immunogenic when removed from its natural context, for example when transplanted into a heterologous polypeptide. An epitope may also refer to that portion of a protein which is immunogenic, where the polypeptide containing the epitope is referred to as the antigen (or sometimes "polypeptide antigen"). A polypeptide or antigen may contain one or more (eg 2 or 3 or more) distinct epitopes. The term "epitope" embraces B-cell and T-cell epitopes. The term "T-cell epitope" embraces CD4+ T-cell epitopes and CD8+ T-cell epitopes (sometimes also referred to as CTL epitopes).

The term "immunogenic polypeptide" refers to a polypeptide which is immunogenic, that is to say it is capable of eliciting an immune response in a mammal, and therefore contains one or more epitopes (eg T-cell and/or B-cell epitopes). Immunogenic polypeptides may contain one or more polypeptide antigens eg in an unnatural arrangement such as in a fusion protein.

Immunogenic polypeptides will typically be recombinant proteins produced eg by expression in a heterologous host such as a bacterial host, in yeast or in cultured mammalian cells.

The term "polypeptide derived from a pathogen" means a polypeptide which partially or wholly contains sequences (i.e. antigens) which occur naturally in pathogens or bear a high degree of sequence identity thereto (eg more than 95% identity over a stretch of at least 10 eg at least 20 amino acids).

Immunogenic polypeptides may contain one or more (eg 1, 2, 3 or 4) polypeptide antigens.

Unless otherwise specified, an "immune response" may be a cellular and/or a humoral response.

In one embodiment of the invention one or more of said one or more first immunogenic polypeptides is substantially the same as one or more of said one or more second immunogenic polypeptides. For example one of the at least one first immunogenic polypeptides and one of the at least one second immunogenic polypeptides may have an overall sequence identity of 90% or more eg 95% or more eg 98% or 99% or more over the length of one or other immunogenic polypeptides.

In another embodiment of the invention one or more of said one or more first immunogenic polypeptides contains at least one antigen which is substantially the same as an antigen contained in one or more of said one or more second immunogenic polypeptides. For example one of the at least one first immunogenic polypeptides and one of the at least one second immunogenic polypeptides may have an overall sequence identity of 90% or more eg 95% or more eg 98% or 99% or more over a stretch of 20 amino acids or more eg 40 amino acids or more eg 60 amino acids or more.

Suitably one or more first immunogenic polypeptides comprise at least one T cell epitope.

Suitably one or more second immunogenic polypeptides comprise at least one T cell epitope.

Suitably the one or more first immunogenic polypeptides comprise at least one B cell epitope.

Suitably the one or more second immunogenic polypeptides comprise at least one B cell epitope In another embodiment of the invention one or more of said one or more first immunogenic polypeptides and one or more of said one or more second immunogenic polypeptides share one or more identical B-cell and/or T-cell epitopes. Suitably they share one or more identical amino acid sequences of length 10 amino acids or more eg 15 amino acids or more eg 25 amino acids or more.

In another embodiment of the invention, none of the one or more of said one or more first immunogenic polypeptides is substantially the same as or contains any antigen in common with one or more of said one or more second immunogenic polypeptides, for example they may have an overall sequence identity of less than 90% over a stretch of 20 amino acids or more eg 40 amino acids or more eg 60 amino acids or more.

Thus, they may not share any B-cell or T-cell epitopes. For example, they may note share any identical amino acid sequences of length 10 amino acids or more eg at 15 amino acids or more eg 25 amino acids or more.

In one specific embodiment of the invention a first immunogenic polypeptide and a second immunogenic polypeptide contain the same antigens in the same arrangement or in a different arrangement (eg in a different arrangement). By "different arrangement" is meant that they may be arranged in a different order and/or they may be divided. In another specific embodiment of the invention a first immunogenic polypeptide and a second immunogenic polypeptide are the same.

The composition according to the invention may contain one first immunogenic polypeptide as the only immunogenic polypeptide in the composition. Alternatively the composition according to the invention may contain more than one first immunogenic polypeptides eg 2 or 3 or 4 or more immunogenic polypeptides.

The composition according to the invention may comprise one adenoviral vector. Alternatively it may comprise more than one adenoviral vector eg 2 adenoviral vectors.

In compositions according to the invention an adenoviral vector may comprise a heterologous polynucleotide which encodes for one second immunogenic polypeptide or it may comprise more than one heterologous polynucleotide which together encode for more than one second immunogenic polypeptide under the control of more than one promoter.

As well as for prophylactic vaccination, the compositions of the invention may also be used in individuals that are already infected with pathogen, and result in improved immunological control of the established infection. This is of particular interest when the pathogen is HIV. In the case of HIV, this control is believed to be achieved by CD8-positive T cells that specifically recognize HIV-infected cells. Such CD8-positive T cell response is maintained by the presence of HIV-specific CD4-positive helper T cells. Therefore, the induction of both types of immune response is particularly useful, and can be achieved by combining different vaccine compositions. A combination of an adjuvanted protein and a recombinant adenovirus is of particular interest. The HIV-infected patients that will benefit from the above-described vaccination are either in the primary infection, latency or terminal phase of HIV infection at the time of vaccination. The patients may or may not undergo other therapeutic treatment interventions against pathogen (in the case of HIV—for example highly active antiretroviral therapy) at the time of vaccination.

Antigens

Antigens of use according to the invention are derived from pathogens. Pathogens include viruses, bacteria, protozoa and other parasitic organisms harmful to mammals including man.

Suitable polypeptide antigens to be administered as polypeptide or polynucleotide encoding polypeptide according to the invention include antigens derived from HIV (eg HIV-1), human herpes viruses (such as gH, gL gM gB gC gK gE or gD or derivatives thereof or Immediate Early protein such as ICP27, ICP 47, ICP4, ICP36 from HSV1 or HSV2), cytomegalovirus, especially Human, (such as gB or derivatives thereof), Epstein Barr virus (such as gp350 or derivatives thereof), Varicella Zoster Virus (such as gp1, II, III and IE63), or from a hepatitis virus such as hepatitis B virus (for example Hepatitis B Surface antigen, PreS1, PreS2 and Surface env proteins, Hepatitis B core antigen or pol), hepatitis C virus (eg Core, E1, E2, P7, NS2, NS3, NS4A, NS4B, NS5A and B) and hepatitis E virus antigen, or from other viral pathogens, such as paramyxoviruses: Respiratory Syncytial virus (such as F and G proteins or derivatives thereof), or antigens from parainfluenza virus, measles virus, mumps virus, human papilloma viruses (for example HPV6, 11, 16, 18, eg L1, L2, E1, E2, E3, E4, E5, E6, E7), flaviviruses (e.g. Yellow Fever Virus, Dengue Virus, Tick-borne encephalitis virus, Japanese Encephalitis Virus) or Influenza virus (such as haemaggluttin, nucleoprotein, NA, or M proteins, or combinations thereof), or antigens derived from bacterial pathogens such as *Neisseria* spp, including *N. gonorrhea* and *N. meningitidis*, eg, transferrin-binding proteins, lactoferrin binding proteins, PDC, adhesins); *S. pyogenes* (for example M proteins or fragments thereof, C5A protease, *S. agalactiae, S. mutans; H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis, M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp., including *C. trachomatis, C. pneumoniae, C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. falciparum* and *P. vivax; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; leishmania* spp., including *L. major; Pneumocystis* spp., including *P. carinii; Trichomonas* spp., including *T. vaginalis; Schisostoma* spp., including *S. mansoni*, or derived from yeast such as *Candida* spp., including *C. albicans; Cryptococcus* spp., including *C. neoformans.*

Further bacterial antigens include antigens derived from *Streptococcus* spp, including *S. pneumoniae* (PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other bacterial antigens include antigens derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

In particular, the methods or compositions of the present invention may be used to protect against or treat viral disorders such as those caused by Hepatitis B virus, Hepatitis C virus, Human papilloma virus, Human immunodeficiency virus (HIV), or Herpes simplex virus; bacterial diseases such as those caused by *Mycobacterium tuberculosis* (TB) or *Chlamydia* sp; and protozoal infections such as malaria.

It is to be recognised that these specific disease states, pathogens and antigens have been referred to by way of example only, and are not intended to be limiting upon the scope of the present invention.

TB Antigens

The pathogen may, for example, be *Mycobacterium tuberculosis.*

Exemplary antigens derived from *M. tuberculosis* are for example alpha-crystallin (HspX), HBHA, Rv1753, Rv2386, Rv2707, Rv2557, Rv2558, RPFs: Rv0837c, Rv1884c, Rv2389c, Rv2450, Rv1009, aceA (Rv0467), ESAT6, Tb38-1, Ag85A, -B or -C, MPT 44, MPT59, MPT45, HSP10, HSP65, HSP70, HSP 75, HSP90, PPD 19 kDa [Rv3763], PPD, 38 kDa [Rv0934]), PstS1, (Rv0932), SodA (Rv3846), Rv2031c, 16 kDa, Ra12, TbH9, Ra35, Tb38-1, Erd 14, DPV, MTI, MSL, DPPD, mTCC1, mTCC2, hTCC1 (WO 99/51748) and hTCC2, and especially Mtb32a, Ra35, Ra12, DPV, MSL, MTI, Tb38-1, mTCC1, TbH9 (Mtb39a), hTCC1, mTCC2 and DPPD. Antigens derived from *M. tuberculosis* also include fusion proteins and variants thereof where at least two, or for example, three polypeptides of *M. tuberculosis* are fused into a larger protein. Such fusions may comprise or consist of Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI (WO 99/51748), Ra12-Tbh9-Ra35-Ag85B and Ra12-Tbh9-Ra35-mTCC2. A particular Ra12-Tbh9-Ra35 sequence that may be mentioned is defined by SEQ ID No 6 of WO2006/117240 together with variants in which Ser 704 of that sequence is mutated to other than serine, eg to Ala, and derivatives thereof incorporating an N-terminal His tag of an appropriate length (eg SEQ ID No 2 or 4 of WO2006/117240). See also SEQ ID No 10 which is a sequence containing an optional starting M and an optional N-terminal His-His tag (positions 2 and 3) and in which the Ala mutated relative to the wild-type Ser is at position 706.

*Chlamydia* Antigens

The pathogen may, for example, be a *Chlamydia* sp. eg *C. trachomatis*.

Exemplary antigens derived from *Chlamydia* sp eg *C. trachomatis* are selected from CT858, CT 089, CT875, MOMP, CT622, PmpD, PmpG and fragments thereof, SWIB and immunogenic fragments of any one thereof (such as PmpDpd and PmpGpd) and combinations thereof. Preferred combinations of antigens include CT858, CT089 and CT875. Specific sequences and combinations that may be employed are described in WO2006/104890.

*Plasmodium* Antigens

The pathogen may, for example be a parasite that causes malaria such as a *Plasmodium* sp. eg *P. falciparum* or *P. vivax*.

For example, antigens derived from *P. falciparum* include circumsporozoite protein (CS protein), PfEMP-1, Pfs 16 antigen, MSP-1, MSP-3, LSA-1, LSA-3, AMA-1 and TRAP. A particular hybrid antigen that may be mentioned is RTS. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. When expressed in yeast RTS is produced as a lipoprotein particle, and when it is co-expressed with the S antigen from HBV it produces a mixed particle known as RTS,S The structure or RTS and RTS,S is disclosed in WO 93/10152. TRAP antigens are described in WO 90/01496. Other *Plasmodium* antigens include *P. falciparum* EBA, GLURP, RAP1, RAP2, Sequestrin, Pf332, STARP, SALSA, PfEXP1, Pfs25, Pfs28, PFS27/25, Pfs48/45, Pfs230 and their analogues in other *Plasmodium* spp. One embodiment of the present invention is a composition comprising RTS,S or CS protein or a fragment thereof such as the CS portion of RTS, S in combination with one or more further malarial antigens which may be selected for example from the group consisting of MSP-1, MSP-3, AMA-1, Pfs 16, LSA-1 or LSA-3. Possible antigens from *P. vivax* include circumsporozoite protein (CS protein) and Duffy antigen binding protein and immunogenic fragments thereof, such as PvRII (see eg WO02/12292).

Thus in one suitable embodiment of the invention, the first and second immunogenic polypeptides are selected from antigens derived from *Plasmodium falciparum* and/or *Plasmodium vivax*.

For example, the first and/or second immunogenic polypeptides are selected from antigens derived from *Plasmodium falciparum* and/or *Plasmodium vivax* are selected from RTS (eg as RTS,S), circumsporozoite (CS) protein, MSP-1, MSP-3, AMA-1, LSA-1, LSA-3 and immunogenic derivatives thereof or immunogenic fragments thereof.

One specific derivative that may be mentioned is the hybrid protein known as RTS, especially when presented in the form of a mixed particle known as RTS,S.

An exemplary RTS sequence is shown in SEQ ID No 14.

An exemplary *P. falciparum* CS protein-derived antigen is shown in SEQ ID No 12. This particular sequence corresponds to the CSP sequence of *P. falciparum* (3D7 strain), which also contains a 19 aa insertion coming from 7G8 strain (81-100).

In one specific embodiment of the invention, a first immunogenic polypeptide is RTS,S and a second immunogenic polypeptide is the CS protein from *Plasmodium falciparum* or an immunogenic fragment thereof.

HPV Antigens

The pathogen may, for example, be a Human Papilloma Virus.

Thus antigens of use in the present invention may, for example, be derived from the Human Papilloma Virus (HPV) considered to be responsible for genital warts (HPV 6 or HPV 11 and others), and/or the HPV viruses responsible for cervical cancer (HPV16, HPV18, HPV33, HPV51, HPV56, HPV31, HPV45, HPV58, HPV52 and others). In one embodiment the forms of genital wart prophylactic, or therapeutic, compositions comprise L1 particles or capsomers, and fusion proteins comprising one or more antigens selected from the HPV proteins E1, E2, E5 E6, E7, L1, and L2. In one embodiment the forms of fusion protein are: L2E7 as disclosed in WO96/26277, and proteinD (1/3)-E7 disclosed in PCT/EP98/05285.

A preferred HPV cervical infection or cancer, prophylaxis or therapeutic composition may comprise HPV 16 or 18 antigens. For example, L1 or L2 antigen monomers, or L1 or L2 antigens presented together as a virus like particle (VLP) or the L1 alone protein presented alone in a VLP or capsomer structure. Such antigens, virus like particles and capsomer are per se known. See for example WO94/00152, WO94/20137, WO94/05792, and WO93/02184. Additional early proteins may be included alone or as fusion proteins such as E7, E2 or preferably E5 for example; particularly preferred embodiments of this includes a VLP comprising L1 E7 fusion proteins (WO 96/11272). In one embodiment the HPV 16 antigens comprise the early proteins E6 or E7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, preferably a Protein D-E6/E7 fusion. Such a composition may optionally provide either or both E6 and E7 proteins from HPV 18, preferably in the form of a Protein D-E6 or Protein D-E7 fusion protein or Protein D E6/E7 fusion protein. Additionally antigens from other HPV strains, preferably from strains HPV 31 or 33 may be employed.

HIV Antigens

The pathogen may, for example, be HIV eg HIV-1.

Thus, antigens may be selected from HIV derived antigens, particularly HIV-1 derived antigens.

HIV Tat and Nef proteins are early proteins, that is, they are expressed early in infection and in the absence of structural protein.

The Nef gene encodes an early accessory HIV protein which has been shown to possess several activities. For example, the Nef protein is known to cause the removal of CD4, the HIV receptor, from the cell surface, although the biological importance of this function is debated. Additionally Nef interacts with the signal pathway of T cells and induces an active state, which in turn may promote more efficient gene expression. Some HIV isolates have mutations or deletions in this region, which cause them not to encode functional protein and are severely compromised in their replication and pathogenesis in vivo.

The Gag gene is translated from the full-length RNA to yield a precursor polyprotein which is subsequently cleaved into 3-5 capsid proteins; the matrix protein p17, capsid protein p24 and nucleic acid binding protein (Fundamental Virology, Fields B N, Knipe D M and Howley M 1996 2. Fields Virology vol 2 1996).

The Gag gene gives rise to the 55-kilodalton (Kd) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the Pol gene) during the process of viral maturation into four smaller proteins designated MA (matrix [p17]), CA (capsid [p24]), NC (nucleocapsid [p9]), and p6.(4).

In addition to the 3 major Gag proteins (p17, p24 and p9), all Gag precursors contain several other regions, which are cleaved out and remain in the virion as peptides of various sizes. These proteins have different roles e.g. the p2 protein has a proposed role in regulating activity of the protease and contributes to the correct timing of proteolytic processing.

The MA polypeptide is derived from the N-terminal, myristoylated end of p55. Most MA molecules remain attached to the inner surface of the virion lipid bilayer, stabilizing the particle. A subset of MA is recruited inside the deeper layers of the virion where it becomes part of the complex which escorts the viral DNA to the nucleus. These MA molecules facilitate the nuclear transport of the viral genome because a karyophilic signal on MA is recognized by the cellular nuclear import machinery. This phenomenon allows HIV to infect non-dividing cells, an unusual property for a retrovirus.

The p24 (CA) protein forms the conical core of viral particles. Cyclophilin A has been demonstrated to interact with the p24 region of p55 leading to its incorporation into HIV particles. The interaction between Gag and cyclophilin A is essential because the disruption of this interaction by cyclosporine inhibits viral replication.

The NC region of Gag is responsible for specifically recognizing the so-called packaging signal of HIV. The packaging signal consists of four stem loop structures located near the 5' end of the viral RNA, and is sufficient to mediate the incorporation of a heterologous RNA into HIV-1 virions. NC binds to the packaging signal through interactions mediated by two zinc-finger motifs. NC also facilitates reverse transcription.

The p6 polypeptide region mediates interactions between p55 Gag and the accessory protein Vpr, leading to the incorporation of Vpr into assembling virions. The p6 region also contains a so-called late domain which is required for the efficient release of budding virions from an infected cell.

The Pol gene encodes three proteins having the activities needed by the virus in early infection, reverse transcriptase RT, protease, and the integrase protein needed for integration of viral DNA into cellular DNA. The primary product of Pol is cleaved by the virion protease to yield the amino terminal RT peptide which contains activities necessary for DNA synthesis (RNA and DNA directed DNA polymerase, ribonuclease H) and carboxy terminal integrase protein. HIV RT is a heterodimer of full-length RT (p66) and a cleavage product (p51) lacking the carboxy terminal RNase H domain.

RT is one of the most highly conserved proteins encoded by the retroviral genome. Two major activities of RT are the DNA Pol and ribonuclease H. The DNA Pol activity of RT uses RNA and DNA as templates interchangeably and like all DNA polymerases known is unable to initiate DNA synthesis de novo, but requires a pre existing molecule to serve as a primer (RNA).

The RNase H activity inherent in all RT proteins plays the essential role early in replication of removing the RNA genome as DNA synthesis proceeds. It selectively degrades the RNA from all RNA-DNA hybrid molecules. Structurally the polymerase and ribo H occupy separate, non-overlapping domains within the Pol covering the amino two thirds of the Pol.

The p66 catalytic subunit is folded into 5 distinct subdomains. The amino terminal 23 of these have the portion with RT activity. Carboxy terminal to these is the RNase H domain.

After infection of the host cell, the retroviral RNA genome is copied into linear double stranded DNA by the reverse transcriptase that is present in the infecting particle. The integrase (reviewed in Skalka A M '99 Adv in Virus Res 52 271-273) recognises the ends of the viral DNA, trims them and accompanies the viral DNA to a host chromosomal site to catalyse integration. Many sites in the host DNA can be targets for integration. Although the integrase is sufficient to catalyse integration in vitro, it is not the only protein associated with the viral DNA in vivo—the large protein-viral DNA complex isolated from the infected cells has been denoted the pre integration complex. This facilitates the acquisition of the host cell genes by progeny viral genomes.

The integrase is made up of 3 distinct domains, the N terminal domain, the catalytic core and the C terminal domain. The catalytic core domain contains all of the requirements for the chemistry of polynucleotidyl transfer.

HIV-1 derived antigens for us in the invention may thus for example be selected from Gag (for example full length Gag), p17 (a portion of Gag), p24 (another portion of Gag), p41, p40, Pol (for example full length Pol), RT (a portion of Pol), p51 (a portion of RT), integrase (a portion of Pol), protease (a portion of Pol), Env, gp120, gp140 or gp160, gp41, Nef, Vif, Vpr, Vpu, Rev, Tat and immunogenic derivatives thereof and immunogenic fragments thereof, particularly Env, Gag, Nef and Pol and immunogenic derivatives thereof and immunogenic fragments thereof including p17, p24, RT and integrase. HIV vaccines may comprise polypeptides and/or polynucleotides encoding polypeptides corresponding to multiple different HIV antigens for example 2 or 3 or 4 or more HIV antigens which may be selected from the above list. Several different antigens may, for example, be comprised in a single fusion protein. More than one first immunogenic polypeptide and/or more than one second immunogenic polypeptide each of which is an HIV antigen or a fusion of more than one antigen may be employed.

For example an antigen may comprise Gag or an immunogenic derivative or immunogenic fragment thereof, fused to RT or an immunogenic derivative or immunogenic fragment thereof, fused to Nef or an immunogenic derivative or immunogenic fragment thereof wherein the Gag portion of the fusion protein is present at the 5' terminus end of the polypeptide.

A Gag sequence of use according to the invention may exclude the Gag p6 polypeptide encoding sequence. A particular example of a Gag sequence for use in the invention comprises p17 and/or p24 encoding sequences.

A RT sequence may contain a mutation to substantially inactivate any reverse transcriptase activity (see WO03/025003).

The RT gene is a component of the bigger pol gene in the HIV genome. It will be understood that the RT sequence employed according to the invention may be present in the context of Pol, or a fragment of Pol corresponding at least to RT. Such fragments of Pol retain major CTL epitopes of Pol. In one specific example, RT is included as just the p51 or just the p66 fragment of RT.

The RT component of the fusion protein or composition according to the invention optionally comprises a mutation to remove a site which serves as an internal initiation site in prokaryotic expression systems.

Optionally the Nef sequence for use in the invention is truncated to remove the sequence encoding the N terminal region i.e. removal of from 30 to 85 amino acids, for example from 60 to 85 amino acids, particularly the N terminal 65 amino acids (the latter truncation is referred to herein as trNef). Alternatively or additionally the Nef may be modified to remove the myristylation site. For example the Gly 2 myristylation site may be removed by deletion or substitution. Alternatively or additionally the Nef may be modified to alter the dileucine motif of Leu 174 and Leu 175 by deletion or substitution of one or both leucines. The importance of the dileucine motif in CD4 downregulation is described e.g. in Bresnahan P. A. et al (1998) Current Biology, 8(22): 1235-8.

The Env antigen may be present in its full length as gp160 or truncated as gp140 or shorter (optionally with a suitable mutation to destroy the cleavage site motif between gp120 and gp41). The Env antigen may also be present in its naturally occurring processed form as gp120 and gp41. These two derivatives of gp160 may be used individually or together as a combination. The aforementioned Env antigens may further exhibit deletions (in particular of variable loops) and truncations. Fragments of Env may be used as well.

An exemplary gp120 sequence is shown in SEQ ID No 8. An exemplary gp140 sequence is shown in SEQ ID No 6.

Immunogenic polypeptides according to the invention may comprise Gag, Pol, Env and Nef wherein at least 75%, or at least 90% or at least 95%, for example, 96% of the CTL epitopes of these native antigens are present.

In immunogenic polypeptides according to the invention which comprise p17/p24 Gag, p66 RT, and truncated Nef as defined above, 96% of the CTL epitopes of the native Gag, Pol and Nef antigens are suitably present.

One embodiment of the invention provides an immunogenic polypeptide containing p17, p24 Gag, p66 RT, truncated Nef (devoid of nucleotides encoding terminal amino-acids 1-85—"trNef") in the order Gag, RT, Nef. In polynucleotides encoding immunogenic polypeptides of the invention, suitably the P24 Gag and P66 RT are codon optimized.

Specific polynucleotide constructs and corresponding polypeptide antigens according to the invention include:

1. p17, p24 (codon optimised) Gag-p66 RT (codon optimised)-truncated Nef;
2. truncated Nef-p66 RT (codon optimised)-p17, p24 (codon optimised) Gag;
3. truncated Nef-p17, p24 (codon optimised) Gag-p66 RT (codon optimised);
4. p66 RT (codon optimised)-p17, p24 (codon optimised) Gag-truncated Nef;
5. p66 RT (codon optimised)-truncated Nef-p17, p24 (codon optimised) Gag;
6. p17, p24 (codon optimised) Gag-truncated Nef-p66 RT (codon optimised).

An exemplary fusion is a fusion of Gag, RT and Nef particularly in the order Gag-RT-Nef (see eg SEQ ID No 2). Another exemplary fusion is a fusion of p17, p24, RT and Nef particularly in the order p24-RT-Nef-p17 (see eg SEQ ID No 16, referred to elsewhere herein as "F4").

In another embodiment an immunogenic polypeptide contains Gag, RT, integrase and Nef, especially in the order Gag-RT-integrase-Nef (see eg SEQ ID No 4).

In other embodiments the HIV antigen may be a fusion polypeptide which comprises Nef or an immunogenic derivative thereof or an immunogenic fragment thereof, and p17 Gag and/or p24 Gag or immunogenic derivatives thereof or immunogenic fragments thereof, wherein when both p17 and p24 Gag are present there is at least one HIV antigen or immunogenic fragment between them.

For example, Nef is suitably full length Nef.

For example p17 Gag and p24 Gag are suitably full length p17 and p24 respectively.

In one embodiment an immunogenic polypeptide comprises both p17 and p24 Gag or immunogenic fragments thereof. In such a construct the p24 Gag component and p17 Gag component are separated by at least one further HIV antigen or immunogenic fragment, such as Nef and/or RT or immunogenic derivatives thereof or immunogenic fragments thereof. See WO2006/013106 for further details.

In fusion proteins which comprise p24 and RT, it may be preferable that the p24 precedes the RT in the construct because when the antigens are expressed alone in *E. coli* better expression of p24 than of RT is observed.

Some constructs according to the invention include the following:

1. p24-RT-Nef-p17
2. p24-RT*-Nef-p17
3. p24-p51RT-Nef-p17
4. p24-p51RT*-Nef-p17
5. p17-p51RT-Nef
6. p17-p51RT*-Nef
7. Nef-p17
8. Nef-p17 with linker
9. p17-Nef
10. p17-Nef with linker

* represents RT methionine$_{592}$ mutation to lysine

In another aspect the present invention provides a fusion protein of HIV antigens comprising at least four HIV antigens or immunogenic fragments, wherein the four antigens or fragments are or are derived from Nef, Pol and Gag. Preferably Gag is present as two separate components which are separated by at least one other antigen in the fusion. Preferably the Nef is full length Nef. Preferably the Pol is p66 or p51RT. Preferably the Gag is p17 and p24 Gag. Other preferred features and properties of the antigen components of the fusion in this aspect of the invention are as described herein.

Preferred embodiments of this aspect of the invention are the four component fusions as already listed above:

1. p24-RT-Nef-p17
2. p24-RT*-Nef-p17
3. p24-p51RT-Nef-p17
4. p24-p51RT*-Nef-p17

The immunogenic polypeptides of the present invention may have linker sequences present in between the sequences corresponding to particular antigens such as Gag, RT and Nef. Such linker sequences may be, for example, up to 20 amino acids in length. In a particular example they may be from 1 to 10 amino acids, or from 1 to 6 amino acids, for example 4-6 amino acids.

Further description of such suitable HIV antigens can be found in WO03/025003.

HIV antigens of the present invention may be derived from any HIV clade, for example clade A, clade B or clade C. For example the HIV antigens may be derived from clade A or B, especially B.

In one specific embodiment of the invention, a first immunogenic polypeptide is a polypeptide comprising Gag and/or Pol and/or Nef or a fragment or derivative of any of them (eg p24-RT-Nef-p17). In one specific embodiment of the invention a second immunogenic polypeptide is a polypeptide comprising Gap and/or Pol and/or Nef or a fragment or derivative of any of them (eg Gag-RT-Nef or Gag-RT-integrase-Nef).

Thus in one specific embodiment, a polypeptide comprising Gap and/or Pol and/or Nef or a fragment or derivative of any of them (eg p24-RT-Nef-p17) is a first immunogenic polypeptide and a polypeptide comprising Gap and/or Pol and/or Nef or a fragment or derivative of any of them (eg Gag-RT-Nef or Gag-RT-integrase-Nef) is a second immunogenic polypeptide.

In another specific embodiment of the invention, a first immunogenic polypeptide is Env or a fragment or derivative thereof eg gp120, gp140 or gp160 (especially gp120). In one specific embodiment of the invention a second immunogenic polypeptide is a polypeptide comprising Gag and/or Pol and/or Nef or a fragment or derivative of any of them (eg p24-RT-Nef-p17).

Thus in one specific embodiment, Env or a fragment or derivative thereof eg gp120, gp140 or gp160 (especially gp120) is a first immunogenic polypeptide and a polypeptide comprising Gag and/or Pol and/or Nef or a fragment or derivative of any of them (eg p24-RT-Nef-p17) is a second immunogenic polypeptide.

In another specific embodiment of the invention, a first immunogenic polypeptide is a polypeptide comprising Gag and/or Pol and/or Nef or a fragment or derivative of any of them (eg p24-RT-Nef-p17). In one specific embodiment of the invention a second immunogenic polypeptide is Env or a fragment or derivative thereof eg gp120, gp140 or gp160 (especially gp120).

Thus in one specific embodiment, a polypeptide comprising Gag and/or Pol and/or Nef or a fragment or derivative of any of them (eg p24-RT-Nef-p17) is a first immunogenic polypeptide and Env or a fragment or derivative thereof eg gp120, gp140 or gp160 (especially gp120) is a second immunogenic polypeptide.

Immunogenic Derivatives and Immunogenic Fragments of Antigens

The aforementioned antigens may be employed in the form of immunogenic derivatives or immunogenic fragments thereof rather than the whole antigen.

As used herein the term "immunogenic derivative" in relation to an antigen of native origin refers to an antigen that have been modified in a limited way relative to its native counterparts. For example it may include a point mutation which may change the properties of the protein eg by improving expression in prokaryotic systems or by removing undesirable activity, eg enzymatic activity. Immunogenic derivatives will however be sufficiently similar to the native antigens such that they retain their antigenic properties and remain capable of raising an immune response against the native antigen. Whether or not a given derivative raises such an immune response may be measured by a suitably immunological assay such as an ELISA (for antibody responses) or flow cytometry using suitable staining for cellular markers (for cellular responses).

Immunogenic fragments are fragments which encode at least one epitope, for example a CTL epitope, typically a peptide of at least 8 amino acids. Fragments of at least 8, for example 8-10 amino acids or up to 20, 50, 60, 70, 100, 150 or 200 amino acids in length are considered to fall within the scope of the invention as long as the polypeptide demonstrates antigenicity, that is to say that the major epitopes (eg CTL epitopes) are retained by the polypeptide.

Adenovirus

Adenoviral vectors of the present invention comprise one or more heterologous polynucleotides (DNA) which encode one or more immunogenic polypeptides.

Adenoviral vectors of use in the present invention may be derived from a range of mammalian hosts.

Adenoviruses (herein referred to as "Ad" or "Adv") have a characteristic morphology with an icosohedral capsid consisting of three major proteins, hexon (II), penton base (III) and a knobbed fibre (IV), along with a number of other minor proteins, VI, VIII, IX, IIIa and IVa2 (Russell W. C. 2000, Gen Viriol, 81:2573-2604). The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Over 100 distinct serotypes of adenovirus have been isolated which infect various mammalian species, 51 of which are of human origin. Thus one or more of the adenoviral vectors may be derived from a human adenovirus. Examples of such human-derived adenoviruses are Ad1, Ad2, Ad4, Ad5, Ad6, Ad11, Ad 24, Ad34, Ad35, particularly Ad5, Ad11 and Ad35. The human serotypes have been categorised into six subgenera (A-F) based on a number of biological, chemical, immunological and structural criteria.

Although Ad5-based vectors have been used extensively in a number of gene therapy trials, there may be limitations on the use of Ad5 and other group C adenoviral vectors due to preexisting immunity in the general population due to natural infection. Ad5 and other group C members tend to be among the most seroprevalent serotypes. Immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

One such area of alternative serotypes are those derived from non human primates, especially chimpanzee adenoviruses. See U.S. Pat. No. 6,083,716 which describes the genome of two chimpanzee adenoviruses.

It has been shown that chimpanzee ("Pan" or "C") adenoviral vectors induce strong immune responses to transgene products as efficiently as human adenoviral vectors (Fitzgerald et al. 2003, J. Immunol. 170:1416).

Non human primate adenoviruses can be isolated from the mesenteric lymph nodes of chimpanzees. Chimpanzee adenoviruses are sufficiently similar to human adenovirus subtype C to allow replication of E1 deleted virus in HEK 293 cells. Yet chimpanzee adenoviruses are phylogenetically distinct from the more common human serotypes (Ad2 and Ad5). Pan 6 is less closely related to and is serologically distinct from Pans 5, 7 and 9.

Thus one or more of the adenoviral vectors may be derived from a non-human primate adenovirus eg a chimpanzee adenovirus such as one selected from serotypes Pan5, Pan6, Pan7 and Pan9.

Adenoviral vectors may also be derived from more than one adenovirus serotype, and each serotype may be from the same or different source. For example they may be derived from more than one human serotype and/or more than one non-human primate serotype. Methods for constructing chimeric adenoviral vectors are disclosed in WO2005/001103.

There are certain size restrictions associated with inserting heterologous DNA into adenoviruses. Human adenoviruses have the ability to package up to 105% of the wild type genome length (Bett et al 1993, J Virol 67 (10), 5911-21). The lower packaging limit for human adenoviruses has been shown to be 75% of the wild type genome length (Parks et al 1995, J Virol 71(4), 3293-8).

One example of adenoviruses of use in the present invention are adenoviruses which are distinct from prevalent naturally occurring serotypes in the human population such as Ad2 and Ad5. This avoids the induction of potent immune responses against the vector which limits the efficacy of subsequent administrations of the same serotype by blocking vector uptake through neutralizing antibody and influencing toxicity.

Thus, the adenovirus may be an adenovirus which is not a prevalent naturally occurring human virus serotype. Adenoviruses isolated from animals have immunologically distinct capsid, hexon, penton and fibre components but are phylogenetically closely related. Specifically, the virus may be a non-human adenovirus, such as a simian adenovirus and in particular a chimpanzee adenovirus such as Pan 5, 6, 7 or 9. Examples of such strains are described in WO03/000283 and are available from the American Type Culture Collection, 10801 University Boulevard, Manassas, Va. 20110-2209, and other sources. Desirable chimpanzee adenovirus strains are Pan 5 [ATCC VR-591], Pan 6 [ATCC VR-592], and Pan 7 [ATCC VR-593].

Use of chimpanzee adenoviruses is thought to be advantageous over use of human adenovirus serotypes because of the lack of pre-existing immunity, in particular the lack of cross-neutralising antibodies, to adenoviruses in the target population. Cross-reaction of the chimpanzee adenoviruses with pre-existing neutralizing antibody responses is only present in 2% of the target population compared with 35% in the case of certain candidate human adenovirus vectors. The chimpanzee adenoviruses are distinct from the more common human subtypes Ad2 and Ad5, but are more closely related to human Ad4 of subgroup E, which is not a prevalent subtype. Pan 6 is less closely related to Pan 5, 7 and 9.

The adenovirus of the invention may be replication defective. This means that it has a reduced ability to replicate in non-complementing cells, compared to the wild type virus. This may be brought about by mutating the virus e.g. by deleting a gene involved in replication, for example deletion of the E1a, E1b, E3 or E4 gene.

The adenoviral vectors in accordance with the present invention may be derived from replication defective adenovirus comprising a functional E1 deletion. Thus the adenoviral vectors according to the invention may be replication defective due to the absence of the ability to express adenoviral E1a and E1b, i.e., are functionally deleted in E1a and E1b. The recombinant adenoviruses may also bear functional deletions in other genes [see WO 03/000283] for example, deletions in E3 or E4 genes. The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., Human Gene Therapy 15:519-530, 2004.

Recombinant adenoviruses may also be constructed having a functional deletion of the E4 gene, although it may be desirable to retain the E4 ORF6 function. Adenovirus vectors according to the invention may also contain a deletion in the delayed early gene E2a. Deletions may also be made in any of the late genes L1 through to L5 of the adenovirus genome. Similarly deletions in the intermediate genes IX and IVa may be useful.

Other deletions may be made in the other structural or non-structural adenovirus genes. The above deletions may be used individually, i.e. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result.

The adenoviral vectors can be produced on any suitable cell line in which the virus is capable of replication. In particular, complementing cell lines which provide the factors missing from the viral vector that result in its impaired replication characteristics (such as E1 and/or E4) can be used. Without limitation, such a cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources, such as PER.C6© cells, as represented by the cells deposited under ECACC no. 96022940 at the European Collection of Animal Cell Cultures (ECACC) at the Centre for Applied Microbiology and Research (CAMR, UK) or Her 96 cells (Crucell).

The polynucleotide sequences which encode immunogenic polypeptides may be codon optimised for mammalian cells. Such codon-optimisation is described in detail in WO05/025614. Codon optimization for certain HIV sequences is further described in WO 03/025003.

In one embodiment of the present invention the polynucleotide constructs comprise an N-terminal leader sequence. The signal sequence, transmembrane domain and cytoplasmic domain are individually all optionally present or deleted. In one embodiment of the present invention all these regions are present but modified.

A promoter for use in the adenoviral vector according to the invention may be the promoter from HCMV IE gene, for example wherein the 5' untranslated region of the HCMV IE gene comprising exon 1 is included and intron A is completely or partially excluded as described in WO 02/36792.

When several antigens are fused into a fusion protein, such protein would be encoded by a polynucleotide under the control of a single promoter.

In an alternative embodiment of the invention, several antigens may be expressed separately through individual promoters, each of said promoters may be the same or different. In yet another embodiment of the invention some of the antigens may form a fusion, linked to a first promoter and other antigen(s) may be linked to a second promoter, which may be the same or different from the first promoter.

Thus, the adenoviral vector may comprise one or more expression cassettes each of which encode one antigen under the control of one promoter. Alternatively or additionally it may comprise one or more expression cassettes each of which encode more than one antigen under the control of one promoter, which antigens are thereby expressed as a fusion. Each expression cassette may be present in more than one locus in the adenoviral vector.

The polynucleotide or polynucleotides encoding immunogenic polypeptides to be expressed may be inserted into any of the adenovirus deleted regions, for example into the E1 deleted region.

Although two or more polynucleotides encoding immunogenic polypeptides may be linked as a fusion, the resulting protein may be expressed as a fusion protein, or it may be expressed as separate protein products, or it may be expressed as a fusion protein and then subsequently broken down into smaller subunits.

Adjuvant

Adjuvants are described in general in Vaccine Design—the Subunit and Adjuvant Approach eg Powell and Newman, Plenum Press, New York, 1995.

Suitable adjuvants include an aluminium salt such as aluminium hydroxide or aluminium phosphate, but may also be a salt of calcium, iron or zinc, or may be an insoluble suspension of acylated tyrosine, or acylated sugars, cationically or anionically derivatised polysaccharides, or polyphosphazenes.

In the formulation of the invention it is preferred that the adjuvant composition preferentially induces a Th1 response. However it will be understood that other responses, including other humoral responses, are not excluded.

It is known that certain vaccine adjuvants are particularly suited to the stimulation of either Th1 or Th2-type cytokine responses. Traditionally the best indicators of the Th1:Th2 balance of the immune response after a vaccination or infection includes direct measurement of the production of Th1 or Th2 cytokines by T lymphocytes in vitro after restimulation with antigen, and/or the measurement of the IgG1:IgG2a ratio of antigen specific antibody responses.

Thus, a Th1-type adjuvant is one which stimulates isolated T-cell populations to produce high levels of Th1-type cytokines in vivo (as measured in the serum) or ex vivo (cytokines that are measured when the cells are re-stimulated with antigen in vitro), and induces antigen specific immunoglobulin responses associated with Th1-type isotype.

Preferred Th1-type immunostimulants which may be formulated to produce adjuvants suitable for use in the present invention include and are not restricted to the following:

The Toll like receptor (TLR) 4 ligands, especially an agonist such as a lipid A derivative particularly monophosphoryl lipid A or more particularly 3 Deacylated monophoshoryl lipid A (3 D-MPL).

3 D-MPL is sold under the trademark MPL® by GlaxoSmithKline and primarily promotes CD4+ T cell responses characterized by the production of IFN-g (Th1 cells i.e. CD4 T helper cells with a type-1 phenotype). It can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3 D-MPL is used. Small particle 3 D-MPL has a particle size such that it may be sterile-filtered through a 0.22 m filter. Such preparations are described in International Patent Application No. WO94/21292. Synthetic derivatives of lipid A are known and thought to be TLR 4 agonists including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol, 1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

Saponins are also preferred Th1 immunostimulants in accordance with the invention. Saponins are well known adjuvants and are taught in: Lacaille-Dubois, M and Wagner H. (1996. A review of the biological and pharmacological activities of saponins. Phytomedicine vol 2 pp 363-386). For example, Quil A (derived from the bark of the South American tree *Quillaja Saponaria Molina*), and fractions thereof, are described in U.S. Pat. No. 5,057,540 and "Saponins as vaccine adjuvants", Kensil, C. R., *Crit Rev Ther Drug Carrier Syst,* 1996, 12 (1-2):1-55; and EP 0 362 279 B1. The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. One such system is known as an Iscom and may contain one or more saponins.

The adjuvant of the present invention may in particular comprises a Toll like receptor (TLR) 4 ligand, especially 3D-MPL, in combination with a saponin.

Other suitable adjuvants include TLR 9 ligands (agonists). Thus another preferred immunostimulant is an immunostimulatory oligonucleotide containing unmethylated CpG dinucleotides ("CpG"). CpG is an abbreviation for cytosine-guanosine dinucleotide motifs present in DNA. CpG is known in the art as being an adjuvant when administered by both systemic and mucosal routes (WO 96/02555, EP 468520, Davis et al., *J. Immunol,* 1998, 160(2):870-876; McCluskie and Davis, *J. Immunol,* 1998, 161(9):4463-6). Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, Nature 374, p546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the CG motif is not methylated, but other unmethylated CpG sequences are known to be immunostimulatory and may be used in the present invention.

In certain combinations of the six nucleotides a palindromic sequence is present. Several of these motifs, either as repeats of one motif or a combination of different motifs, can be present in the same oligonucleotide. The presence of one or more of these immunostimulatory sequences containing oligonucleotides can activate various immune subsets, including natural killer cells (which produce interferon γ and have cytolytic activity) and macrophages (Wooldrige et al Vol 89 (no. 8), 1977). Other unmethylated CpG containing sequences not having this consensus sequence have also now been shown to be immunomodulatory.

CpG when formulated into vaccines, is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al. supra; Brazolot-Millan et al., *Proc. Natl. Acad. Sci*., USA, 1998, 95(26), 15553-8).

Other TLR9 agonists of potential interest include immunostimulatory CpR motif containing oligonucleotides and YpG motif containing oligonucleotides (Idera).

Such immunostimulants as described above may be formulated together with carriers, such as for example liposomes, oil in water emulsions, and or metallic salts, including aluminium salts (such as aluminium hydroxide). For example, 3D-MPL may be formulated with aluminium hydroxide (EP 0 689 454) or oil in water emulsions (WO 95/17210); QS21 may be advantageously formulated with cholesterol containing liposomes (WO 96/33739), oil in water emulsions (WO 95/17210) or alum (WO 98/15287); CpG may be formulated with alum (Davis et al. supra; Brazolot-Millan supra) or with other cationic carriers.

Combinations of immunostimulants are also preferred, in particular a combination of a monophosphoryl lipid A and a saponin derivative (WO 94/00153; WO 95/17210; WO 96/33739; WO 98/56414; WO 99/12565; WO 99/11241), more particularly the combination of QS21 and 3D-MPL as disclosed in WO 94/00153. Alternatively, a combination of CpG plus a saponin such as QS21 also forms a potent adjuvant for use in the present invention. Alternatively the saponin may be formulated in a liposome or in an Iscom and combined with an immunostimulatory oligonucleotide.

Thus, suitable adjuvant systems include, for example, a combination of monophosphoryl lipid A, preferably 3D-MPL, together with an aluminium salt (eg as described in WO00/23105).

An enhanced system involves the combination of a monophosphoryl lipid A and a saponin derivative particularly the combination of QS21 and 3D-MPL as disclosed in WO 94/00153, or a less reactogenic composition where the QS21 is quenched in cholesterol containing liposomes (DQ) as disclosed in WO 96/33739. This combination may additionally comprise an immunostimulatory oligonucleotide.

Thus an example adjuvant comprises QS21 and/or MPL and/or CpG.

A particularly potent adjuvant formulation involving QS21, 3D-MPL & tocopherol in an oil in water emulsion is described in WO 95/17210 and is another preferred formulation for use in the invention.

Another preferred formulation comprises a CpG oligonucleotide alone or together with an aluminium salt.

In a further aspect of the present invention there is provided a method of manufacture of a vaccine formulation as herein described, wherein the method comprises admixing one or more first immunogenic polypeptides according to the invention with a suitable adjuvant.

Particularly preferred adjuvants for use in the formulations according to the invention are as follows:

i) 3D-MPL+QS21 in a liposome (see eg Adjuvant B below)
ii) Alum+3D-MPL
iii) Alum+QS21 in a liposome+3D-MPL
iv) Alum+CpG
v) 3D-MPL+QS21+oil in water emulsion
vi) CpG
vii) 3D-MPL+QS21 (eg in a liposome)+CpG
viii) QS21+CpG.

Preferably, the adjuvant is presented in the form of a liposome, ISCOM or an oil-in-water emulsion. In one example embodiment of the invention the adjuvant comprises an oil-in-water emulsion. In another example embodiment of the invention the adjuvant comprises liposomes.

Suitably the adjuvant component does not contain any virus. Thus suitably, compositions for use according to the invention do not contain any virus other than the one or more more adenoviral vectors comprising one or more heterologous polynucleotides encoding one or more second immunogenic polypeptides derived from a pathogen.

Compositions, Dosage and Administration

In methods of the invention, the immunogenic polypeptide(s), the adenoviral vector(s) and the adjuvant are administered concomitantly.

Typically the adjuvant will be co-formulated with an immunogenic polypeptide. Suitably the adjuvant will also be co-formulated with any other immunogenic polypeptide to be administered.

Thus in one embodiment of the invention there is provided a method of raising an immune response which comprises administering (i) one or more first immunogenic polypeptides co-formulated with an adjuvant; and (ii) one or more adenoviral vectors comprising one or more heterologous polynucleotides encoding one or more second immunogenic polypeptides; wherein one or more first immunogenic polypeptides and adjuvant, and one or more adenoviral vectors are administered concomitantly.

By "co-formulated" is meant that the first immunogenic polypeptide and the adjuvant are contained within the same composition eg a pharmaceutical composition.

Typically the adenoviral vector is contained in a composition eg a pharmaceutical composition.

Alternatively, the one or more first immunogenic polypeptides, the one or more adenoviral vectors and an adjuvant are co-formulated.

Thus, there are provided compositions according to the invention which comprise one or more immunogenic polypeptides, one or more adenoviral vectors, and an adjuvant.

Compositions and methods according to the invention may involve use of more than one immunogenic polypeptide and/or more than one adenoviral vector. Use of multiple antigens is especially advantageous in raising protective immune responses to certain pathogens, such as HIV, *M. tuberculosis* and *Plasmodium* sp. Compositions according to the invention may comprise more than one adjuvant.

Compositions and methods employed according to the invention may typically comprise a carrier eg an aqueous buffered carrier. Protective components such as sugars may be included.

Compositions should be administered in sufficient amounts to transduce the target cells and to provide sufficient levels of gene transfer and expression and to permit pathogen-specific immune responses to develop thereby to provide a prophylactic or therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, direct delivery to the liver, inhalation, intranasal, intravenous, intramuscular, intratracheal, subcutaneous, intradermal, epidermal, rectal, oral and other parenteral routes of administration. Routes of administration may be combined, if desired, or adjusted depending upon the gene product or the condition. The route of administration primarily will depend on the nature of the condition being treated. Most suitably the route is intramuscular, intradermal or epidermal.

Preferred tissues to target are muscle, skin and mucous membranes. Skin and mucous membranes are the physiological sites where most infectious antigens are normally encountered.

When the first immunogenic polypeptide, adjuvant and adenoviral vector are not co-formulated, the different formulations (eg polypeptide/adjuvant and adenoviral vector formulations) may be administered by the same route of administration or by different routes of administration.

Dosages of compositions in the methods will depend primarily on factors such as the condition being treated, the age, weight and health of the subject, and may thus vary among subjects. For example, a therapeutically effective adult human or veterinary dosage is generally in the range of from about 100 µL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles of virus together with around 1-1000 ug, or about 2-100 ug eg around 4-40 ug immunogenic polypeptide. Dosages will range depending upon the size of the animal and the route of administration. For example, a suitable human or veterinary dosage (for about an 80 kg animal) for intramuscular injection is in the range of about $1\times10^9$ to about $5\times10^{12}$ virus particles and 4-40 ug protein per mL, for a single site. One of skill in the art may adjust these doses, depending on the route of administration, and the therapeutic or vaccinal application for which the composition is employed.

The amount of adjuvant will depend on the nature of the adjuvant and the immunogenic polypeptide, the condition being treated and the age, weight and health of the subject. Typically for human administration an amount of adjuvant of 1-100 ug eg 10-50 ug per dose may be suitable.

Suitably an adequate immune response is achieved by a single concomitant administration of the composition or compositions of the invention in methods of the invention. However if the immune response is further enhanced by administration of a further dose of first immunogenic polypeptide, adjuvant and adenoviral vector on a second or subsequent occasion (for example after a month or two months) then such a protocol is embraced by the invention.

We have found that good pathogen-specific CD4+ and/or CD8+ T-cell responses may typically be raised after a single concomitant administration of the composition or compositions of the invention in methods of the invention. However we have found that good pathogen-specific antibody responses may require a second or further concomitant administration of the composition or compositions of the invention.

The components of the invention may be combined or formulated with any suitable pharmaceutical excipient such as water, buffers and the like.

EXAMPLES

Adjuvant Preparations

1) The Preparation of Oil in Water Emulsion Followed the Protocol as Set Forth in WO 95/17210.

The emulsion contains: 42.72 mg/ml squalene, 47.44 mg/ml tocopherol, 19.4 mg/ml Tween 80. The resulting oil droplets have a size of approximately 180 nm.

Tween 80 was dissolved in phosphate buffered saline (PBS) to give a 2% solution in the PBS. To provide 100 ml two fold concentrate, emulsion 5 g of DL alpha tocopherol and 5 ml of squalene were vortexed until mixed thoroughly. 90 ml of PBS/Tween solution was added and mixed thoroughly. The resulting emulsion was then passed through a syringe and finally microfluidised by using an M110S microfluidics machine. The resulting oil droplets have a size of approximately 180 nm.

2) Preparation of Oil in Water Emulsion with QS21 and MPL

Sterile bulk emulsion was added to PBS to reach a final concentration of 500 µl of emulsion per ml (v/v). 3 D-MPL was then added. QS21 was then added. Between each addition of component, the intermediate product was stirred for 5 minutes. Fifteen minutes later, the pH was checked and adjusted if necessary to 6.8+/−0.1 with NaOH or HCl. The final concentration of 3D-MPL and QS21 was 100 µg per ml for each.

3) Preparation of Liposomal MPL

A mixture of lipid (such as phosphatidylcholine either from egg-yolk or synthetic) and cholesterol and 3 D-MPL in organic solvent, was dried down under vacuum (or alternatively under a stream of inert gas). An aqueous solution (such as phosphate buffered saline) was then added, and the vessel agitated until all the lipid was in suspension. This suspension was then microfluidised until the liposome size was reduced to about 100 nm, and then sterile filtered through a 0.2 µm filter. Extrusion or sonication could replace this step. Typically the cholesterol:phosphatidylcholine ratio was 1:4 (w/w), and the aqueous solution was added to give a final cholesterol concentration of 10 mg/ml.

The final concentration of MPL is 2 mg/ml.

The liposomes have a size of approximately 100 nm and are referred to as SUV (for small unilamelar vesicles). The liposomes by themselves are stable over time and have no fusogenic capacity.

4) Preparation of Adjuvant B ("Adj B")

Sterile bulk of SUV was added to PBS. PBS composition was $Na_2HPO_4$: 9 mM; $KH_2PO_4$: 48 mM; NaCl: 100 mM pH 6.1. QS21 in aqueous solution was added to the SUV. The final concentration of 3D-MPL and QS21 was 100 μg per ml for each. This mixture is referred as Adjuvant B. Between each addition of component, the intermediate product was stirred for 5 minutes. The pH was checked and adjusted if necessary to 6.1+/−0.1 with NaOH or HCl.

Preparation of p24-RT-Nef-P17 Protein ("F4")

F4 was prepared as described in WO2006/013106 Example 1, codon-optimised method.

Preparation of Chimp Adenovirus Pan7 Containing Gab-RT-Nef Transgene ("Pan7GRN")

Construction of Gag, RT, Nef Plasmid.

Plasmid p73i-Tgrn

The full sequence of the Tgrn plasmid insert is given in SEQ ID No 1 and the plasmid construction shown graphically in FIG. 1. This contains p17 p24 (codon optimised) Gag, p66 RT (codon optimised and inactivated) and truncated Nef.

The plasmid P73i-Tgrn was prepared as described in WO03/025003 Examples 1-13.

Construction of the E1/E3 Deleted Pan 7 Adenovirus

The E1/E3 deleted Pan 7 Adenovirus was prepared as described in WO2006/120034 Example 1.

Other serotypes of vectors can be constructed in a similar way. A full description of the construction of E1, E3 and E4 deletions in this and other Pan Adenovirus serotypes is given in WO03/0046124. Further information is also available in Human Gene Therapy 15:519-530.

Insertion of Gag, RT, Nef Sequence into Adenovirus

Using plasmid P73i-Tgrn, the GRN expression cassette was inserted into E1/E3 deleted Pan 7 adenovirus to produce C7-GRNc as described in WO2006/120034 Example 3. C7-GRNc is the Pan7GRN adenovirus component used in the examples set out herein.

Example 1

Immunogenicity Study in Mice Immunised with Adenovirus Component (Pan7GRN) and Protein Component (F4/Adjuvant B) Separately or with Both Adenovirus and Protein Components Co-Formulated Together The mouse strain used was CB6F1 and 3 mice were used per timepoint. For immunisation with F4/adjuvant B (P), 1/10 of the human dose was injected i.e. 9 ug of F4 protein in 50 uL of adjuvant B. For immunisation with Pan7GRN (A), $10\times10^8$ virus particles in 50 uL of saline (0.9% NaCl water for injection solution) was used. The Pan7GRN chimp adenovirus carries the genes coding for Gag (G), RT (R) and Nef (N).

The vaccination schedule was as follows:

| Group | Day 0 | Day 21 | Day 42 | Day 63 |
|---|---|---|---|---|
| 1 | — | — | F4/adj B | F4/adj B |
| 2 | | | Pan7GRN | Pan7GRN |
| 3 | F4/adj B | F4/adj B | Pan7GRN | Pan7GRN |
| 4 | Pan7GRN | Pan7GRN | F4/adj B | F4/adj B |
| 5 | — | — | — | F4/adj B/ Pan7GRN |
| 6 | — | — | F4/adj B/ Pan7GRN | F4/adj B/ Pan7GRN |
| 7 | — | — | adj B | adj B |
| 8 | — | — | — | — |

Thus it can be seen that in groups 1 and 2, the mice were immunized with 2 injections of protein (PP) or adenovirus (AA), respectively. Mice from groups 3 and 4, received a conventional prime-boost schedule: protein then adenovirus (PPAA) or the other way round (AAPP) whereas in groups 5 and 6, the mice received one or two injections of a combination (combo) of protein and adenovirus together according to the invention. Mice from group 7 only received adjuvant control whereas mice from group 6 were naive.

Figure 4:
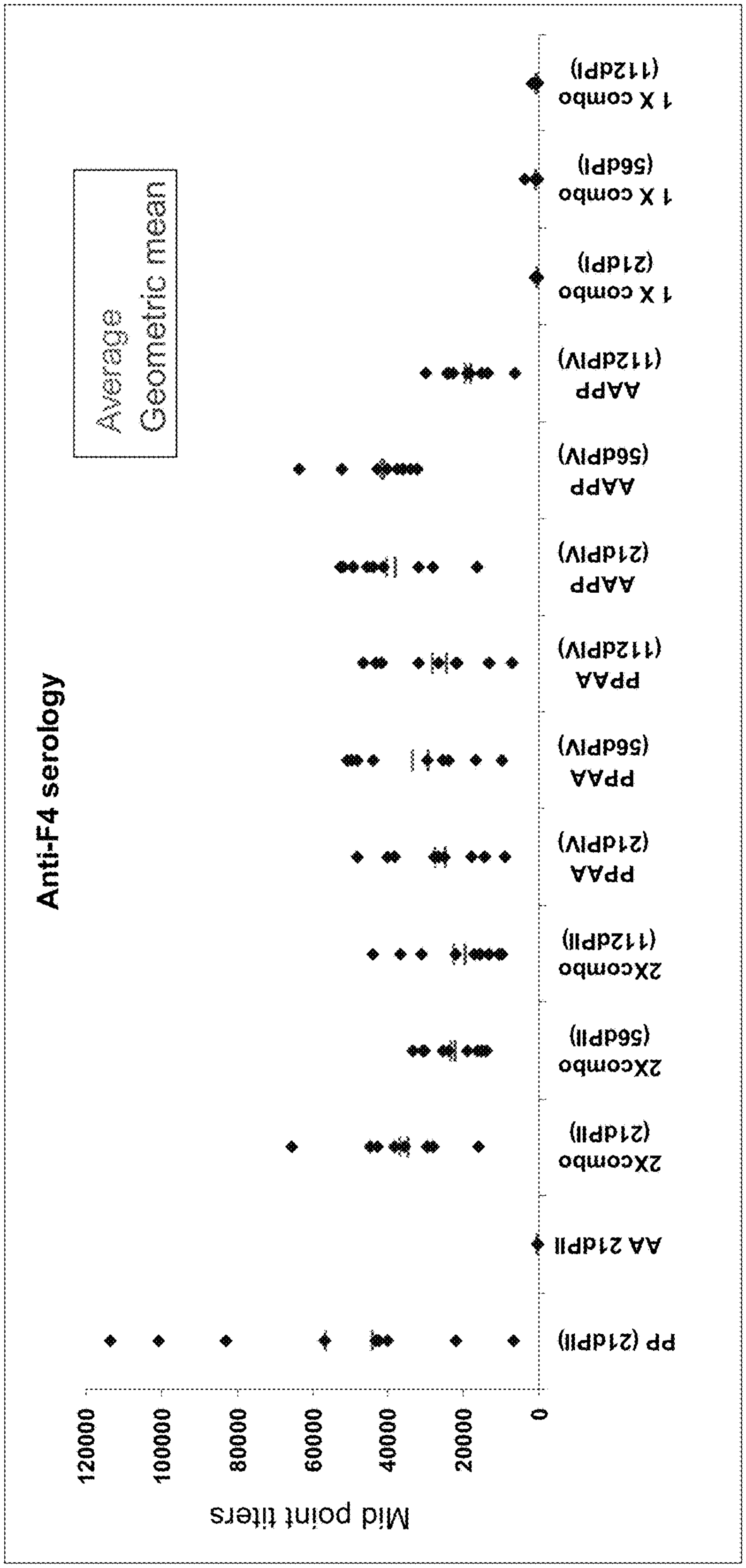
Figure 5:
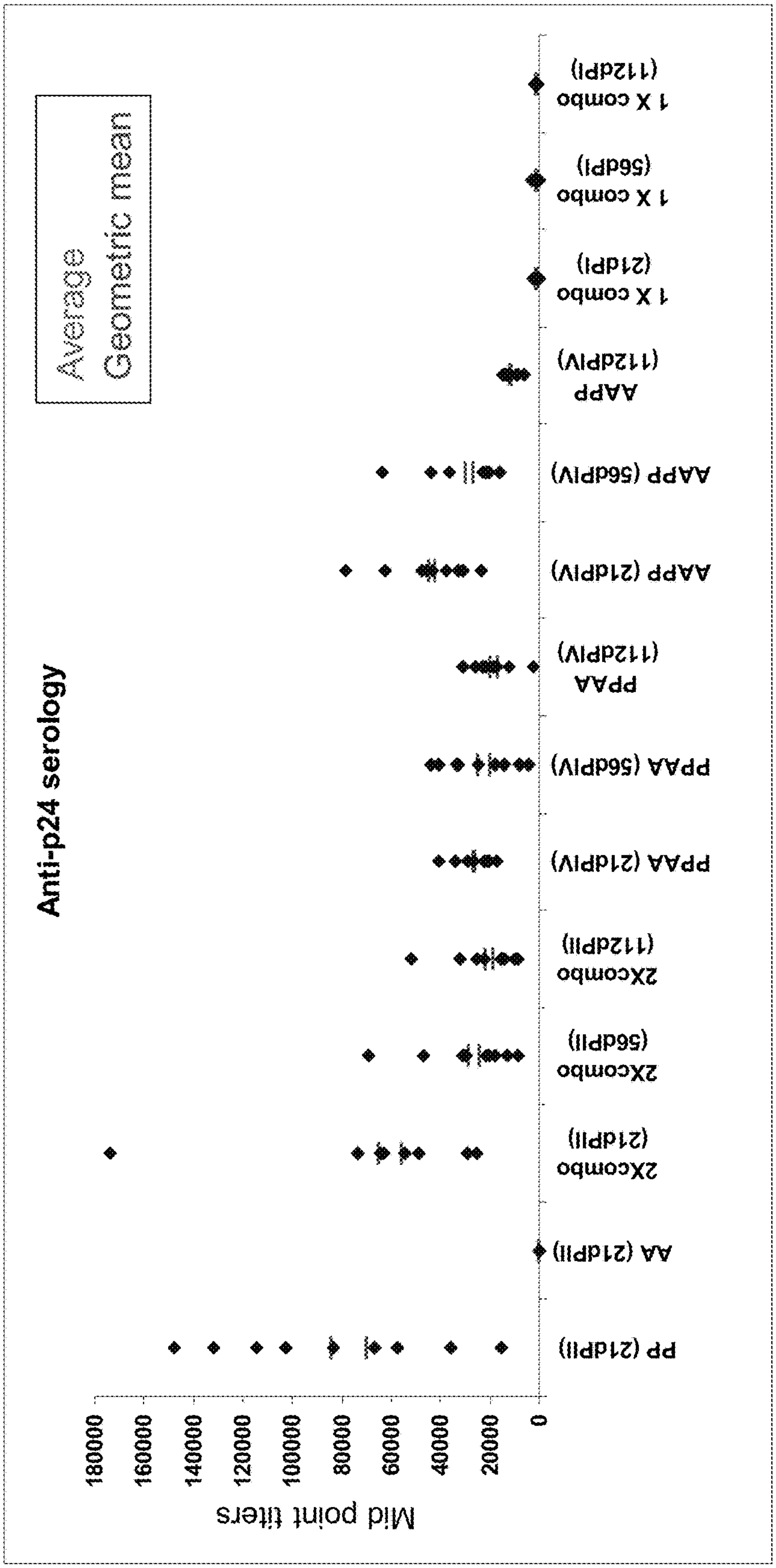
Figure 6:
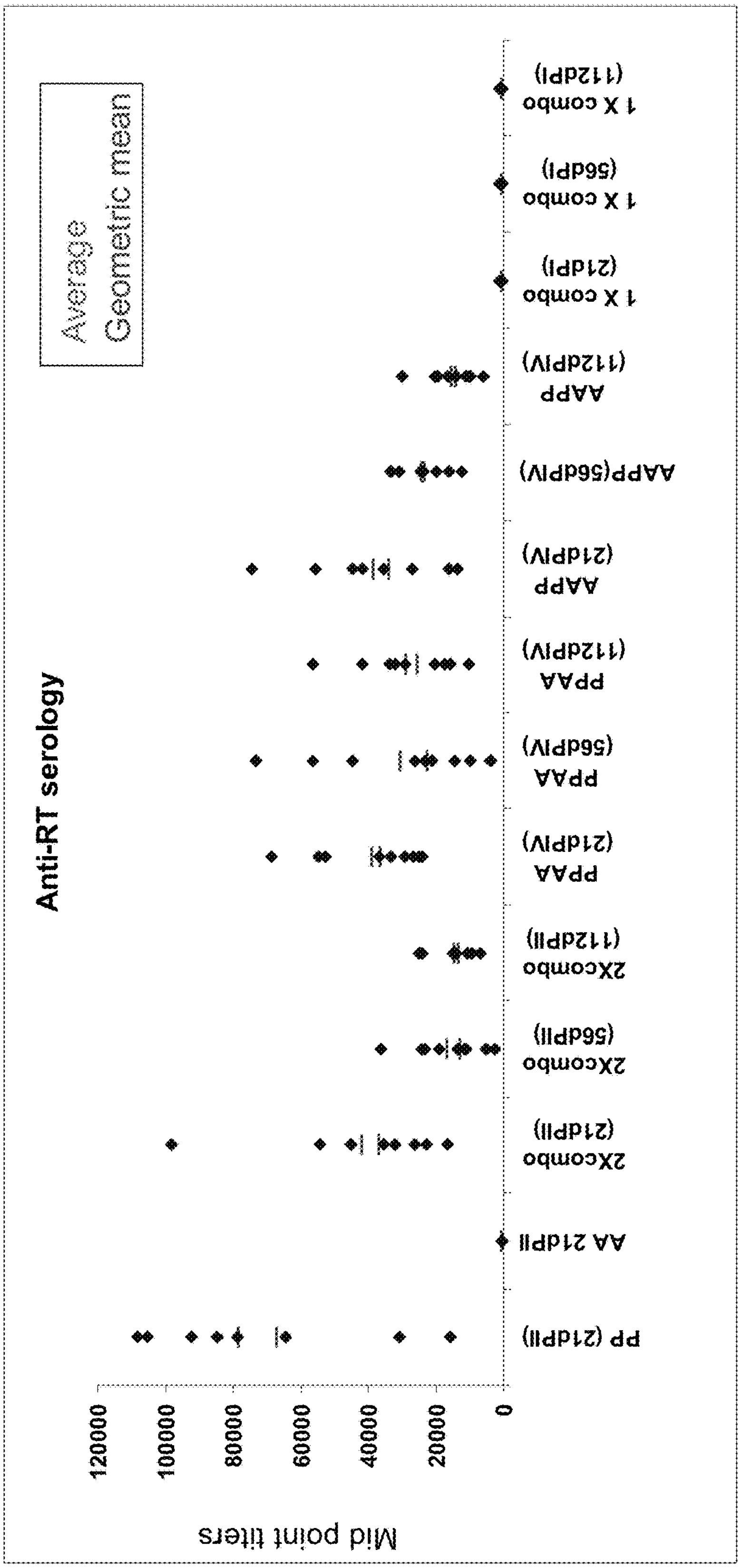
Figure 7:
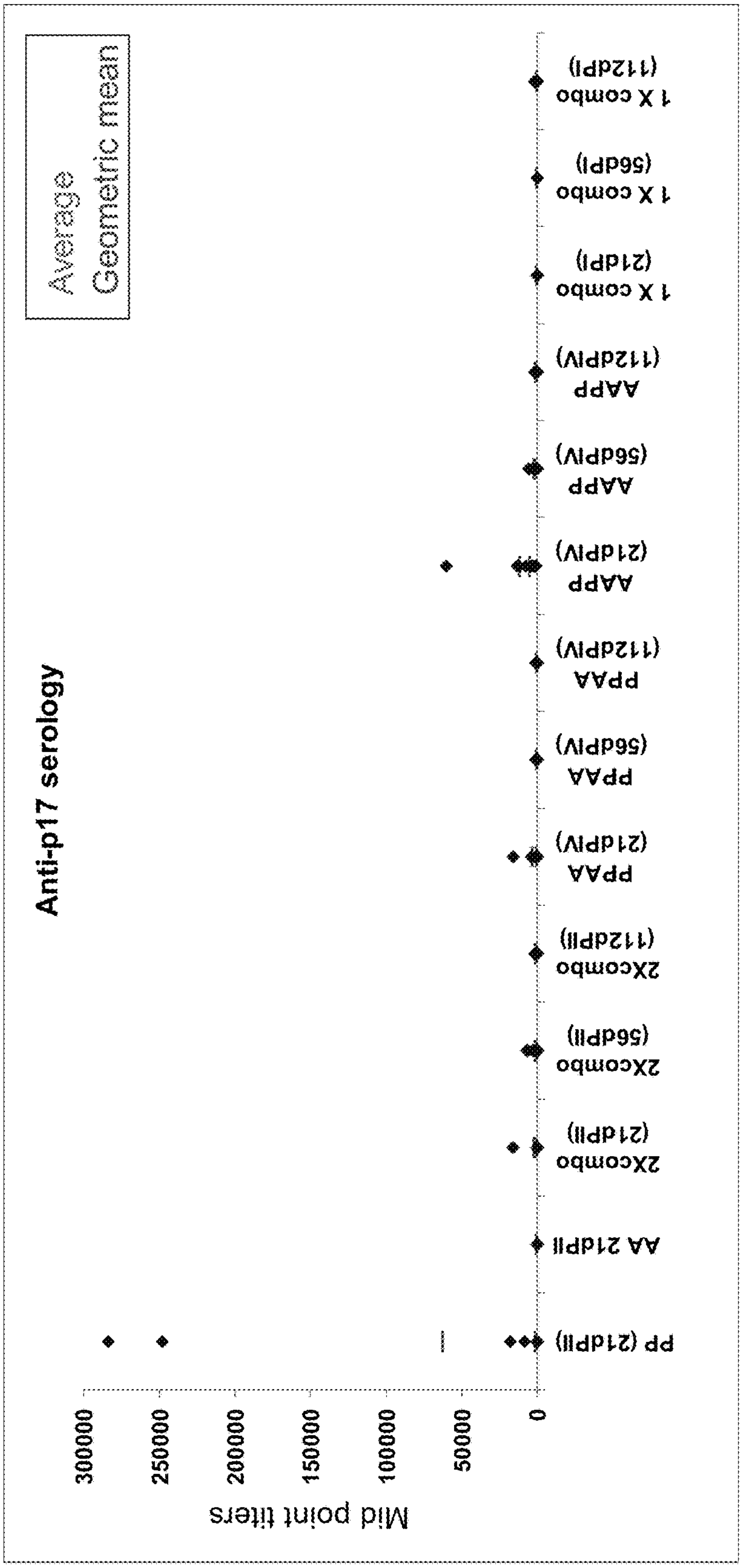

The following read-outs were performed:

Antibody responses (ELISA performed on the sera from each individual animals from each group):

antibody response against F4 (FIG. 4)

antibody response against F4 components p24, RT, Nef and p17 (FIGS. 5-8)

Cellular Responses (FIGS. 2A-3B):

measured by flow cytometry following surface and intracellular cytokine staining after overnight restimulation of spleen cells with pools of peptides of p24, RT, Nef or p17. The spleen cells of 3 mice per timepoint and per group were pooled for the analysis.

For groups 1 and 2, samples were taken for measurement 21 days after the corresponding final immunisation. For the remaining groups, measurements were taken 21 days, 56 days and 112 days after the corresponding final immunisation.

Results:

The results are shown in FIGS. 2A-8.

The X axis labels correspond as follows:

PP—Group 1 animals following second immunisation

AA—Group 2 animals following second immunisation

PPAA—Group 3 animals following fourth immunisation

AAPP—Group 4 animals following fourth immunisation

Combo—Group 5 animals following immunisation

Combo×2—Group 6 animals following second immunisation

The measurement timepoints (21, 56 or 112 days post last immunisation) are indicated in parentheses.

Cellular Responses (FIGS. 2A-3B):

At the timepoints analysed, the data show that CD4+ T-cell responses were observed mainly against p24, RT and Nef.

Figure 2A:
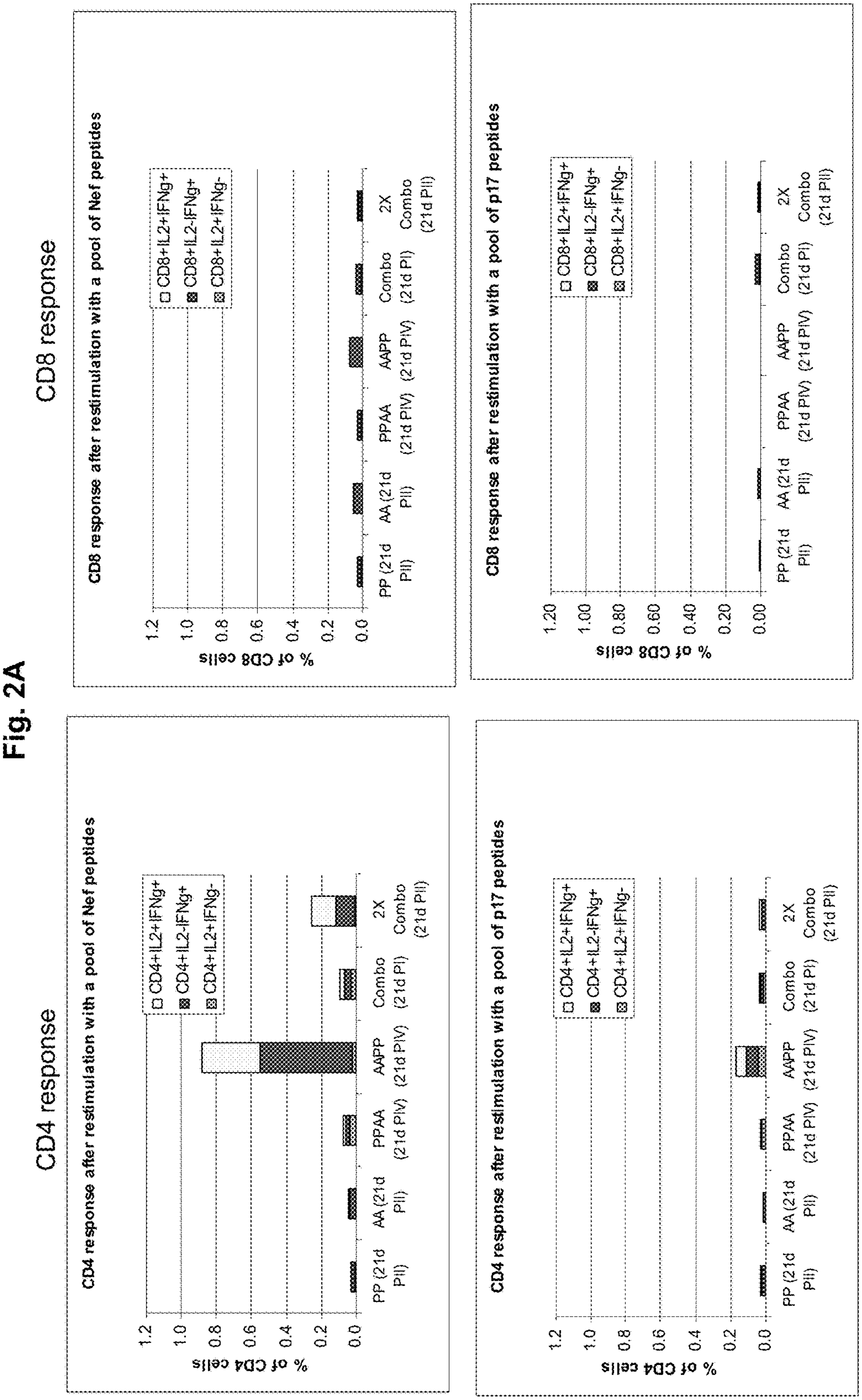
Figure 2B:
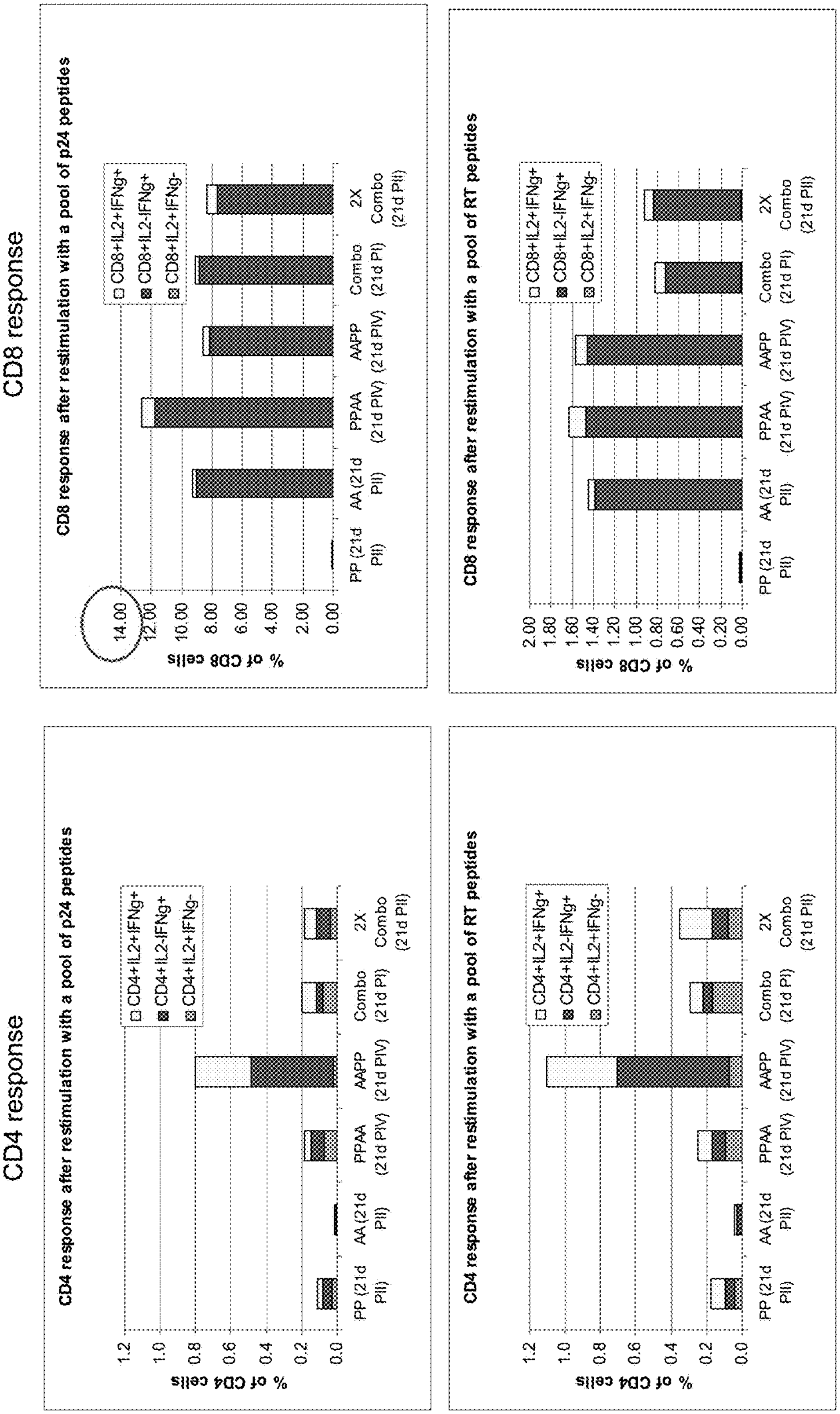

As shown in FIGS. 2A and 2B (left panels), 21 days post last immunisation, the highest CD4+ T-cell responses are observed with two immunisations of adenovirus followed by two immunisations of protein/adjuvant (Group 4 animals). One injection of the combination of adenovirus/protein/adjuvant induces higher CD4+ T-cell levels than two injections of protein/adjuvant following restimulation with p24, RT or Nef peptides.

For restimulation by RT and Nef, two immunisations with the combination of adenovirus/protein/adjuvant induces a CD4+ T-cell response slightly higher than with one immunisation with the combination, whereas the responses with one or two immunisations were identical for p24.

At the timepoints analysed, the CD8+ T-cell responses are mainly observed against the p24 and RT peptides, and no significant numbers of CD8+ T-cells specific for Nef or p17 were detected.

As shown in FIGS. 2A and 2B (right panels), 21 days post last immunisation CD8+ T-cell responses were similar after one or two immunisations with the combination of adenovirus/protein/adjuvant. The CD8 response against p24 observed in groups immunised either (i) twice with adenovirus or (ii) twice with adenovirus followed by twice with protein or (iii) once or twice with the combination of adenovirus/protein/adjuvant were comparable to each other and slightly lower than the one from the group immunised twice with protein followed by twice with adenovirus. The CD8 response against RT observed in groups immunised once or twice with the combination of adenovirus/protein/adjuvant were comparable and slightly lower to the one from the groups immunised either (i) twice with adenovirus or (ii) twice with adenovirus followed by twice with protein or (iii) twice with protein followed by twice with adenovirus.

Figure 3A:
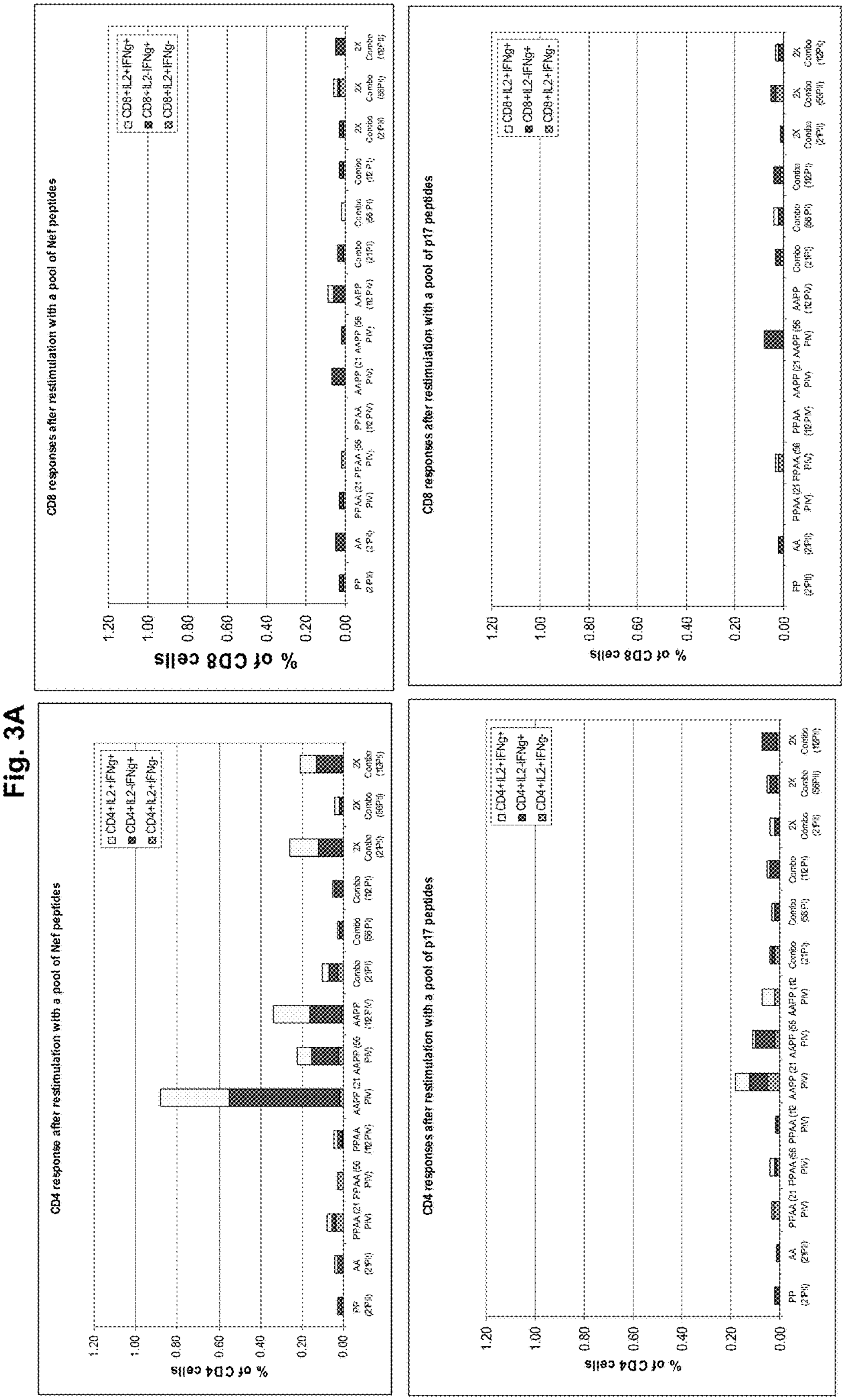
Figure 3B:
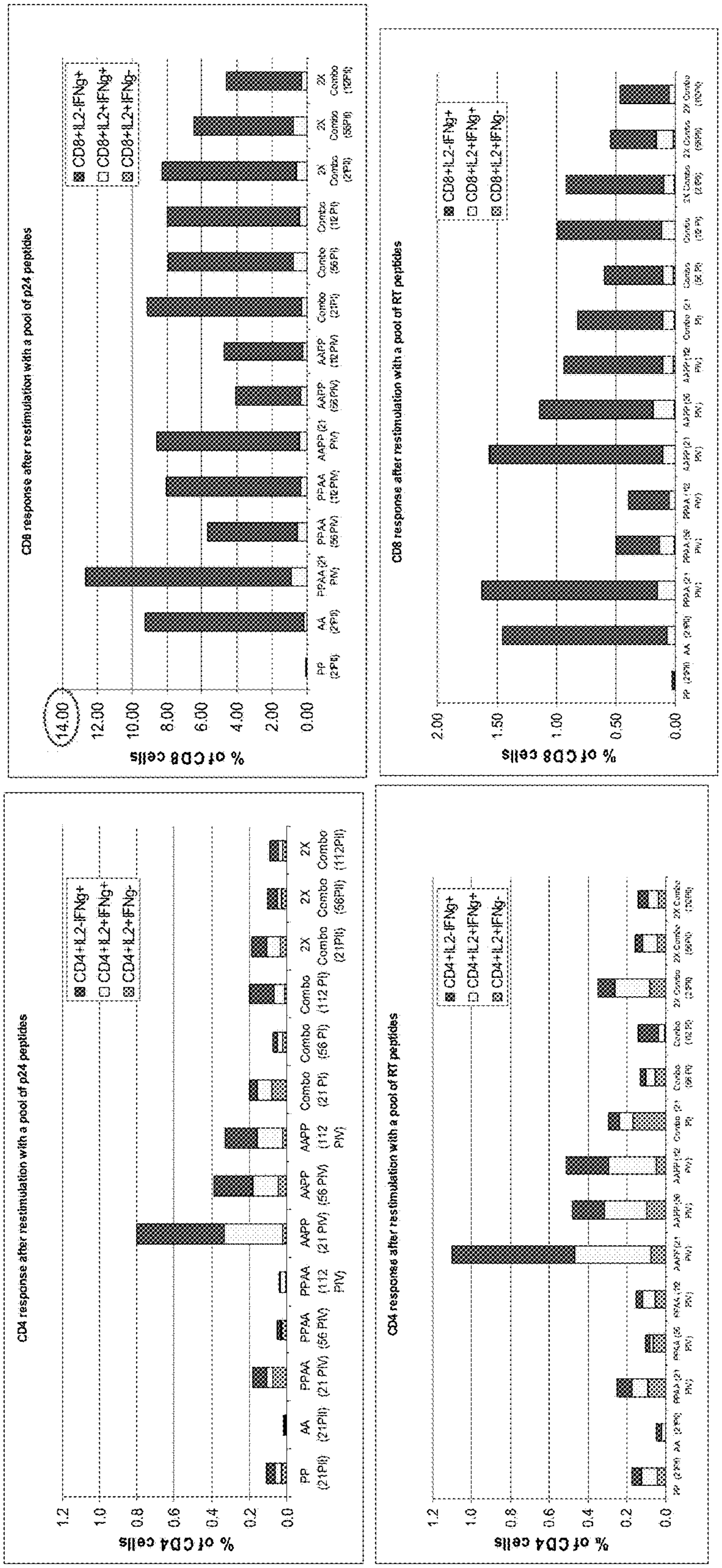

The CD4 and CD8 T cell responses were also analysed at later timepoints (56 and 112 days post last immunisation), when persistence of the responses can be determined (FIGS. 3A and 3B). The CD4 responses (FIGS. 3A and 3B, left panels) are mainly observed against p24, RT and Nef. At these timepoints, the highest CD4 responses are observed in the animals immunised twice with adenovirus followed by twice with protein. The CD4 response in mice immunised once or twice with the combination of adenovirus/protein/adjuvant were comparable to each other and generally higher than the response observed in groups immunised twice with protein followed by twice with adenovirus.

At the later timepoints, the CD8 response against p24 is the highest in the group immunised once with the combination of adenovirus/protein/adjuvant (FIG. 3B, right panel). It is comparable to the one from animals immunised twice with protein followed by twice with adenovirus and slightly higher than the one from the animals immunised either (i) twice with the combination of adenovirus/protein/adjuvant or (ii) twice with adenovirus followed by twice with protein. The latter two are comparable between each other. The CD8 response against RT is the highest and similar in groups immunised (i) twice with the combination of adenovirus/protein/adjuvant or (ii) twice with adenovirus followed by twice with protein. The CD8 response against RT from groups immunised (i) twice with the combination of adenovirus/protein/adjuvant or (ii) twice with protein followed by twice with adenovirus was slightly lower but comparable between each other (FIGS. 3A-3B). As shown in FIG. 3A (right panel), no significant numbers of CD8+ T-cells specific for Nef or p17 were detected.

Figure 8:
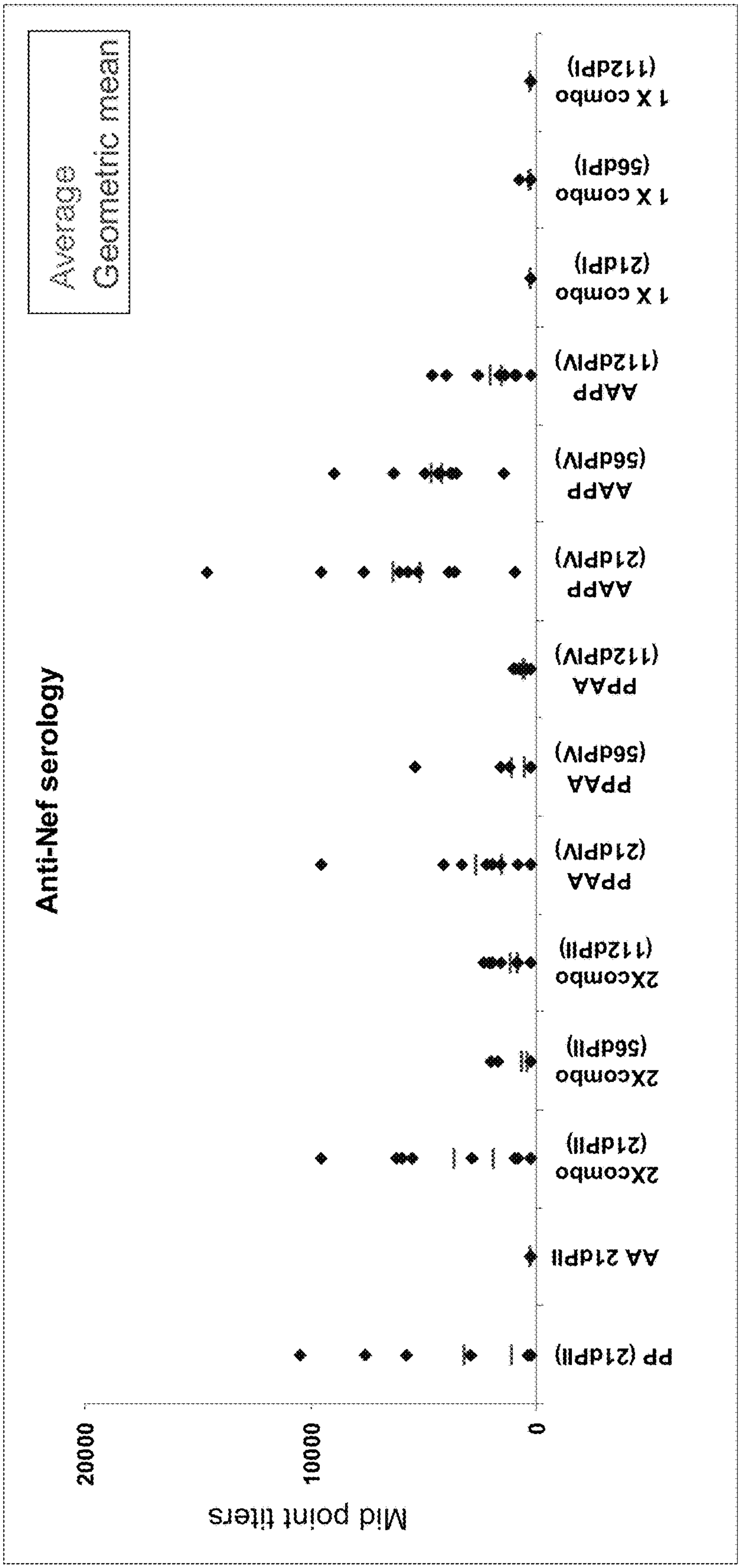

Antibody Responses:

As shown in FIGS. 4 to 8, the antibody responses detected are mainly directed against p24 (FIG. 5), RT (FIG. 6) and Nef (FIG. 8). The anti-F4 (FIG. 4) response generally mimics the response observed against each of the p24, RT or Nef components and can be characterized as follows:

- Low to no antibody response is detected in groups immunised (i) twice with adenovirus or (ii) once with the combination of adenovirus/protein/adjuvant;
- The highest antibody responses usually detected in group immunised twice with the protein at 21 days post immunisation. However, it is also in this group that the highest variability between individuals is observed. In addition, for the anti-Nef serology, the group immunised twice with adenovirus followed by twice with protein appears to display the highest response, when compared to the other groups;
- The response observed in groups immunised (i)) twice with the combination of adenovirus/protein/adjuvant or (ii) twice with protein followed by twice with adenovirus or (iii) twice with adenovirus followed by twice with protein are comparable, peak at 21 days post last immunisation and then slightly decrease over time.

Antibody responses against p17 (FIG. 7) were very low to undetectable in all groups.

Conclusion:

Globally, the highest antigen-specific cell-mediated immune response is observed in the AAPP treatment group after 4 immunisations. However, when comparing groups after 2 immunisations (i.e. AA, PP and 2×combo groups), the induction of both antigen-specific CD4 and CD8 T cell responses is only observed in the group immunised twice with the protein/adenovirus/adjuvant combination. In addition, similar levels of CD4 and CD8 T cell responses can be reached after a single injection of the protein/adenovirus/adjuvant combination. Moreover, in terms of persistence, the antigen-specific T cell responses observed 112 days after the $2^{nd}$ immunisation with the protein/adenovirus/adjuvant combination are comparable to the ones observed 112 days after the $4^{th}$ immunisations in the AAPP treatment group. Finally, it appears that 2 immunisations with the protein/adenovirus/adjuvant combination are needed to obtain an antibody response comparable to the one obtained in the group immunised twice with the adjuvanted protein, group that provided the highest antibody responses in general.

Example 2

Immunogenicity Study in Mice Immunised with Pan7GRN Adenovirus and F4 Protein/Adjuvant B Co-Formulated Together The mouse strain used was CB6F1 with 9 mice per group. Mice were immunized once with a co-formulation of the F4 protein (1/10 of the human dose was injected i.e. 9 ug) together with $10\times10^8$ virus particles of Pan7GRN, in 50 uL of adjuvant B or a dilution of the latter (½, ¼ or 1/10). The CD4 and CD8 cellular responses against a pool of either Nef, p17, p24 or RT peptides were determined 21 days post immunization (3 pools of 3 spleens for each group).

The following read-out was performed:

Cellular Responses (FIG. 9):

measured by flow cytometry following surface and intracellular cytokine staining after overnight restimulation of spleen cells with pools of peptides of p24, RT, Nef or p17. The spleen cells were pooled (3 pools of 3 spleens per group) for the analysis.

Figure 9:
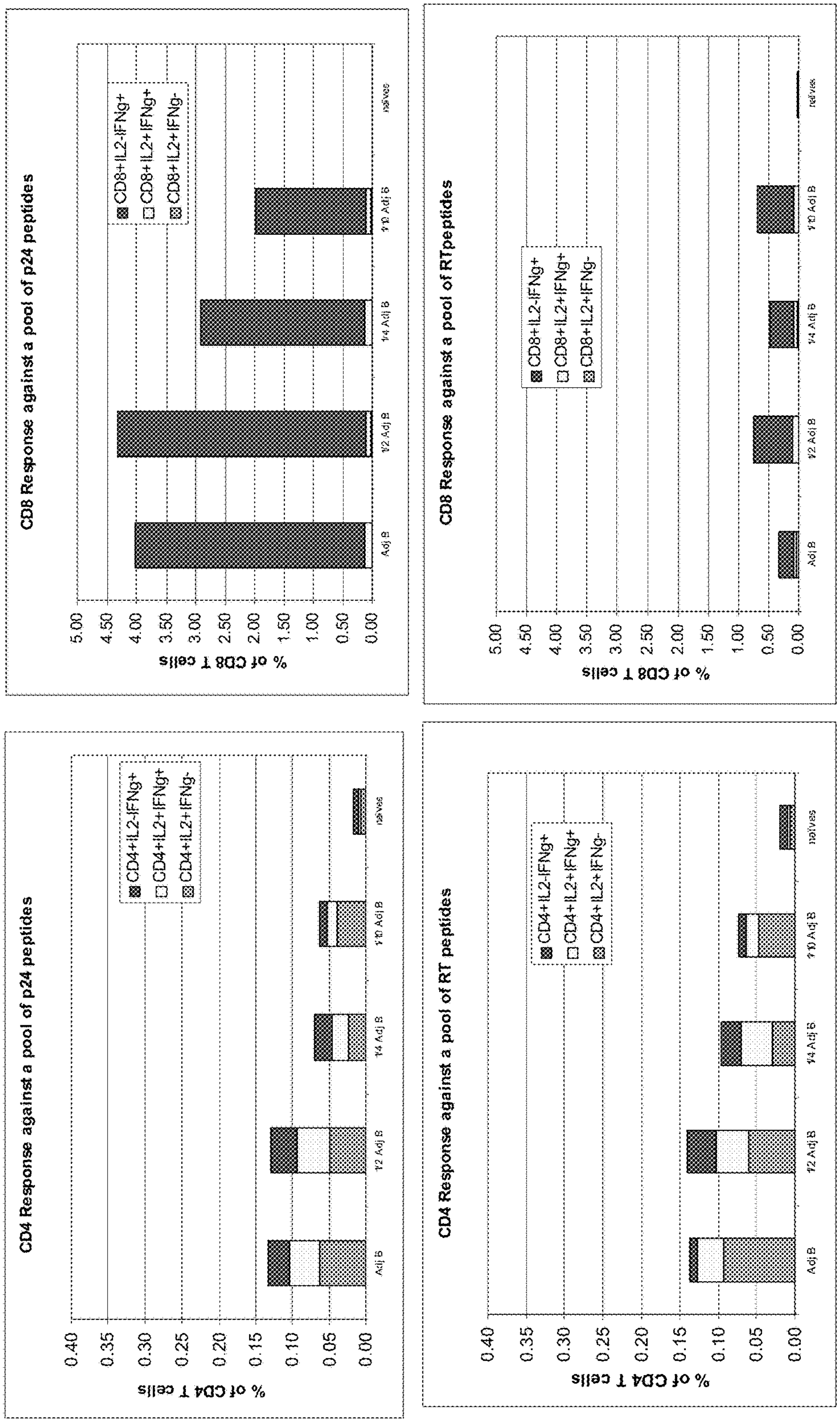
FIG. 9 shows the results of experiments discussed in Example 2, specifically: CD4+ T-cell responses in response to restimulation by pools of peptides derived from p24 and RT following various immunization protocols.

Results:

The results shown in FIG. 9 represent the cellular responses observed after restimulation with a pool of p24 or RT peptides.

The X axis labels correspond as follows:

Adj B—Mice immunised with 9 μgF4/$10^8$vpPan7GRN/non-diluted adjuvant B

½ Adj B—Mice immunised with 9 μgF4/$10^8$vpPan7GRN/adjuvant B diluted ½

¼ Adj B—Mice immunised with 9 μgF4/$10^8$vpPan7GRN/adjuvant B diluted ¼

1/10 Adj B—Mice immunised with 9 μgF4/$10^8$vpPan7GRN/adjuvant B diluted 1/10

Naïve—Naïve mice (no immunisation)

The results indicate that CD4 (FIG. 9, left panel) and CD8 (FIG. 9, right panel) responses are mainly observed against p24 and RT, with the CD8 T cell response specific to RT being lower than the one specific to p24. In addition, the results indicate that the CD4 responses against p24 and RT at 21 days post-immunisations in the groups immunised with the non-diluted adjuvant B or a ½ dilution of it are similar. These CD4 responses tend to decrease when the adjuvant is diluted ¼. When the adjuvant B is diluted at 1/10, the CD4 responses observed are similar to the ones from groups immunised with the ¼ dilution of the adjuvant B. The anti-CD8 responses against p24 are comparable whether the adjuvant is diluted ½ or not. However, the response decreases when the adjuvant B is diluted ¼ and even more so if it is diluted 1/10. In contrast, such trends are not seen for the anti-RT CD8 responses where there is not a real dose range effect of the dose of adjuvant used.

Conclusion:

CD4+ cells and CD8+ cells against F4 components were induced by a single administration of a composition containing an immunogenic polypeptide, an adenoviral vector containing a heterologous polynucleotide encoding an immunogenic polypeptide and an adjuvant, even when the latter was diluted. The impact of adjuvant dilution differed depending on the antigen-specific CD4 or CD8 responses of interest. In particular the highest responses observed were against p24 and the anti-p24 CD4 and CD8 T cell responses show a dose range effect correlating with the dose of adjuvant used in the combination vaccine. While the same effect can be observed for the anti-RT CD4 T cell response, the dose range effect of the dose of adjuvant used in the combo is less clear for the anti-RT CD8 T cell response. Finally, if we consider the global antigen-specific CD4 and CD8 T cell responses and sum the responses against the 4 antigens, a dose range can be observed.

Example 3

Immunogenicity Study in New Zealand White Rabbits Immunised with Pan7GRN or F4/Adjuvant B Sequentially or with Both Adenovirus and Protein Components Co-Formulated Together For immunisation with F4/adjuvant B, the human dose was injected i.e. 90 ug of F4 protein in 500 uL of adjuvant B. For immunisation with Pan7GRN, $10\times10^{10}$ or $10\times10^{12}$ virus particles in 500 uL of saline were used. For the immunization with both adenovirus and protein components co-formulated together, 90 μg of F4 protein, $10\times10^{11}$ virus particles of Pan7 GRN in 500 uL of adjuvant B were used.

The vaccination schedule was as follows:

| Group | Day 0 | Day 14 | Day 126 |
|---|---|---|---|
| 1 | F4/adj B | F4/adj B | F4/adj B |
| 2 | Pan7GRN 10^10 | | Pan7GRN 10^10 |
| 3 | Pan7GRN 10^12 | | Pan7GRN 10^12 |
| 4 | F4/adj B/ Pan7GRN 10^11 | F4/adj B/ Pan7GRN 10^11 | F4/adj B/ Pan7GRN 10^11 |

There were 3 rabbits per group except for group 1 which included only 2 rabbits.

The following read-outs were performed:

Antibody responses (ELISA performed on the sera from each individual animals from each group):

antibody response against F4 antibody response against F4 components p24, RT, Nef and p17

Lymphoproliferative Responses:

The lymphoproliferation was determined by the uptake of tritiated thymidine by peripheral blood mononuclear cells (isolated from whole blood after a density gradient) restimulated in vitro with pools of Nef, p17, p24 and/or RT peptides for 88 hours in the presence of tritiated thymidine for the last 16 hours of the incubation.

Figure 10:
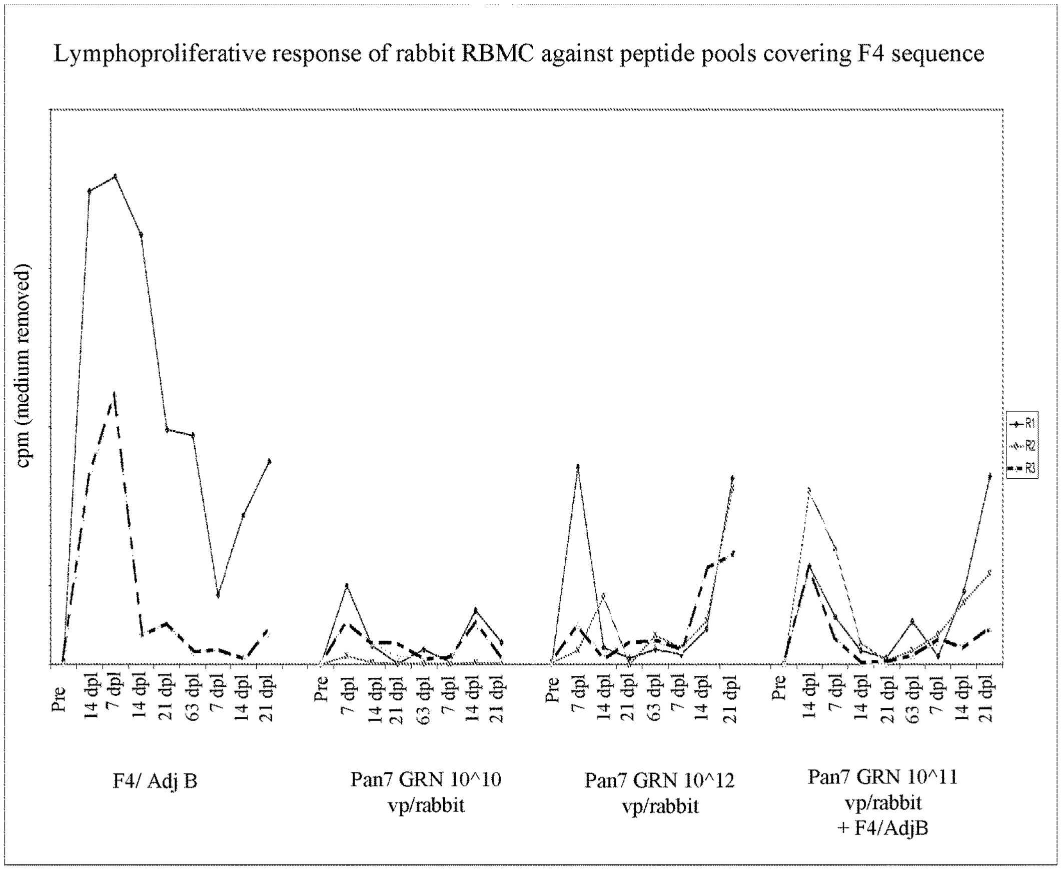

Results:

Lymphoproliferative Response:

As shown in FIG. 10, the highest lymphoproliferative responses are observed in the group immunised twice with protein. The lymphoproliferative response from animals immunised twice with the combination of adenovirus/protein/adjuvant was observed in all rabbits from the group. It actually peaked after one injection and could be further recalled (at similar levels than after the $1^{st}$ injection) following a third injection of the combination of adenovirus/protein/adjuvant, suggesting that the first two injections did not induce a neutralizing response that would inhibit any response to a further similar injection. In its intensity, the proliferative response observed in rabbits immunised with the combination of adenovirus/protein/adjuvant was comparable to the one observed in animals immunised once or twice with $10^{12}$ viral particles of adenovirus and appeared higher than the one from animals immunised once or twice with $10^{10}$ viral particles of adenovirus. Altogether, this suggests that using the combination of adenovirus/protein/adjuvant could decrease the dose of adenovirus to be used. Finally, after a third injection of the combination of adenovirus/protein/adjuvant, the response observed in group 4 was similar to the one from animals immunised 3 times with the protein (group 1).

Figure 11:
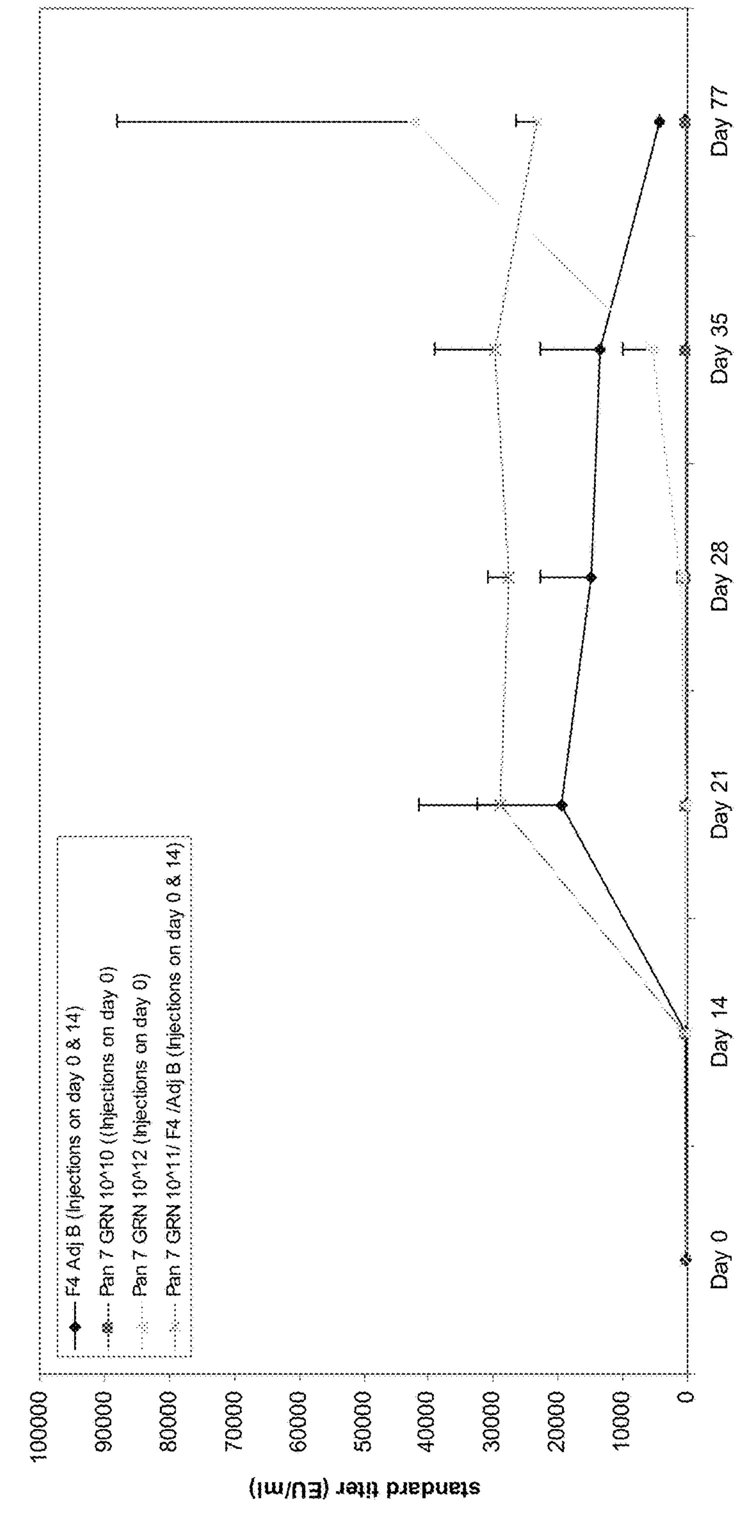
Figure 12A:
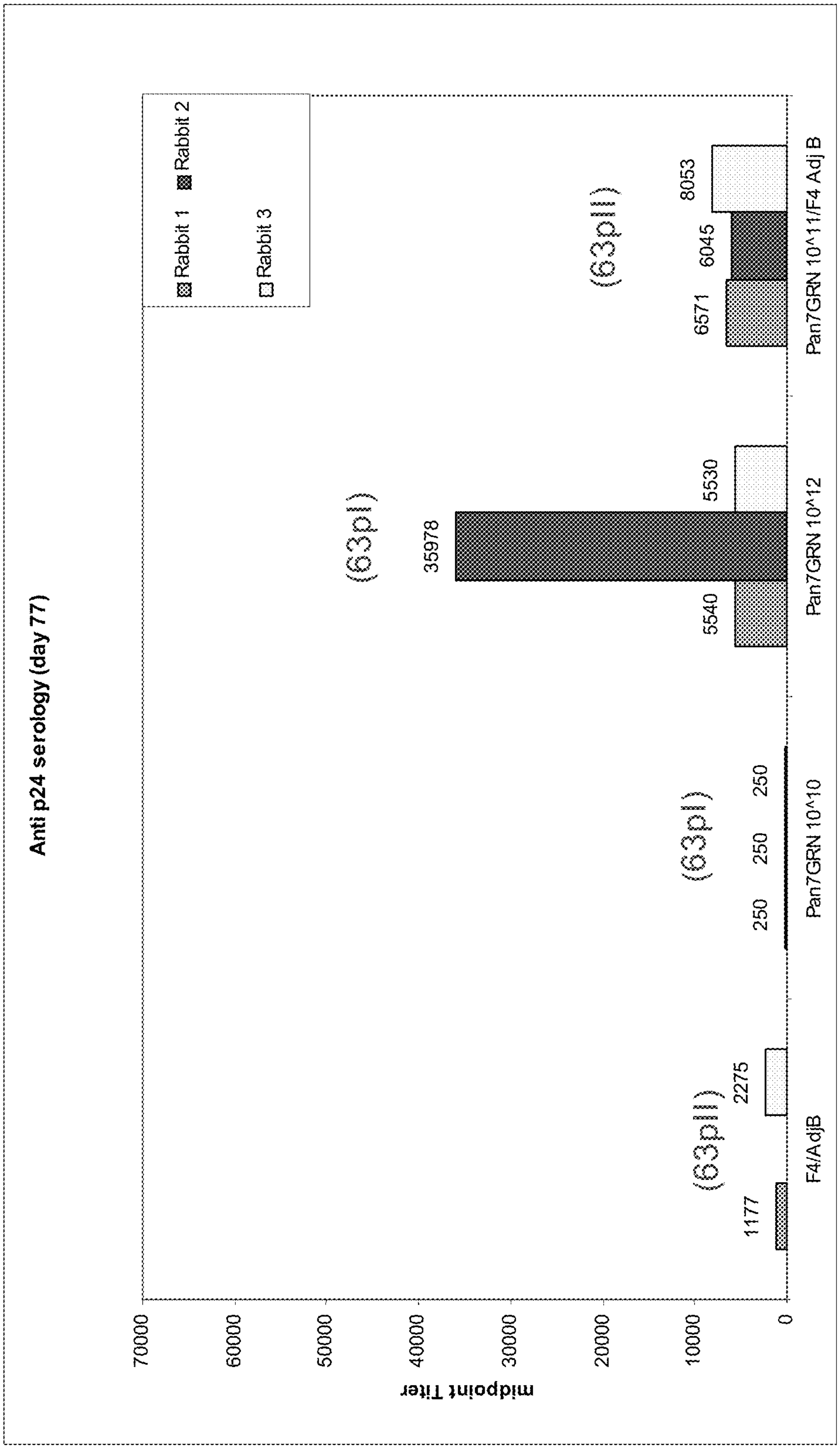
FIGS. 12A and 12B show antibody responses (on day 77) against F4 components p24 and RT respectively.
Figure 12B:
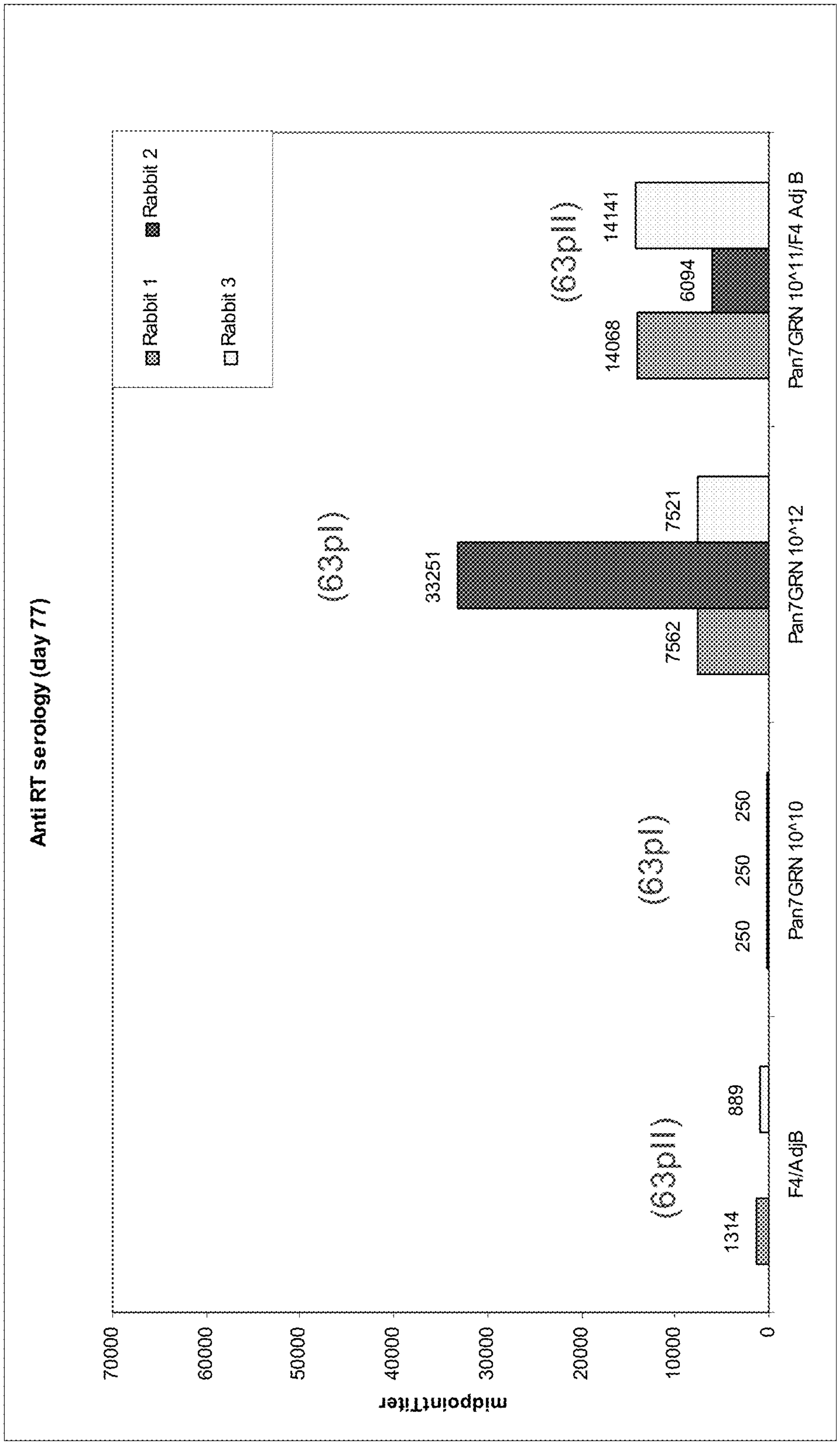

Serology:

As shown in FIG. 11, the kinetic of the anti-F4 antibody response observed in the animals immunised twice with the combination of adenovirus/protein/adjuvant is similar to the one from animals immunised twice with the protein: it is already detected at 7 days post-2nd injection and then decrease over time. However, in terms of intensity, the anti-F4 response of animals immunised twice with the combination of adenovirus/protein/adjuvant remains higher at later timepoints (21 and 63 days post-2nd immunisation) when compared to the anti-F4 response from animals immunised twice with the protein. No anti-F4 antibody response is observed in rabbits immunised once with $10^{10}$ viral particles of adenovirus. In rabbits immunised once with $10^{12}$ viral particles of adenovirus, an anti-F4 response is only detected at 21 and 63 days post-immunisation. In that group, the high variability of the response observed at the 63 day post-immunisation timepoint (d77) results from a single animal (out of the 3) displaying higher titers against the different F4 components, especially p24 and RT as shown in FIGS. 12A and 12B respectively. The anti-F4 antibody response is mainly composed of antibodies targeting p24 and RT and to a much lesser extent Nef and p17.

Conclusion:

Lymphoproliferative and antibody responses could be induced in rabbits after two injections of a composition containing an immunogenic polypeptide, an adenoviral vector containing a heterologous polynucleotide encoding an immunogenic polypeptide and an adjuvant. In addition, we have evidence that a lymphoproliferative response can be recalled after a third injection of such composition. Finally, the best antibody response (in intensity and persistence) is observed with the adenovirus/protein/adjuvant combination.

Example 4

Immunogenicity of F4 (Codon Optimized)/Adjuvant B and C7-GRN when Administrated as a Combination in CB6F1 Mice.

Experimental Design

CB6F1 mice were immunized twice (days 0 and 21) with different combinations listed below. F4co/adjuvant B was used at 9 μg F4co/animal in 50p1 Adjuvant B (1/10 human dose) and the C7-GRN virus at $10^8$ viral particles/animal. F4co in Example 4 is F4 prepared as described in WO2006/013106 Example 1, codon-optimised method.

Combinations

C7-GRN

C7-GRN/adjuvant B

C7-GRN/F4co

C7-GRN/F4co/adjuvant B
F4co
F4co/adjuvant B
adjuvant B
C7 empty
C7empty/adjuvant B
C7empty/F4co
C7empty/F4co/adjuvant B Schedule of Immunizations and Immune Response Analysis Immunisations were carried out at day 0 and day 21. Intracellular cytokine staining (ICS) was carried out at 21 days, 28 days (7 days post immunisation 2), 42 days (21 days post immunisation 2), and 77 days (56 days post immunisation 2).

Results

HIV-Specific CD4 T Cell Responses

Figure 13:
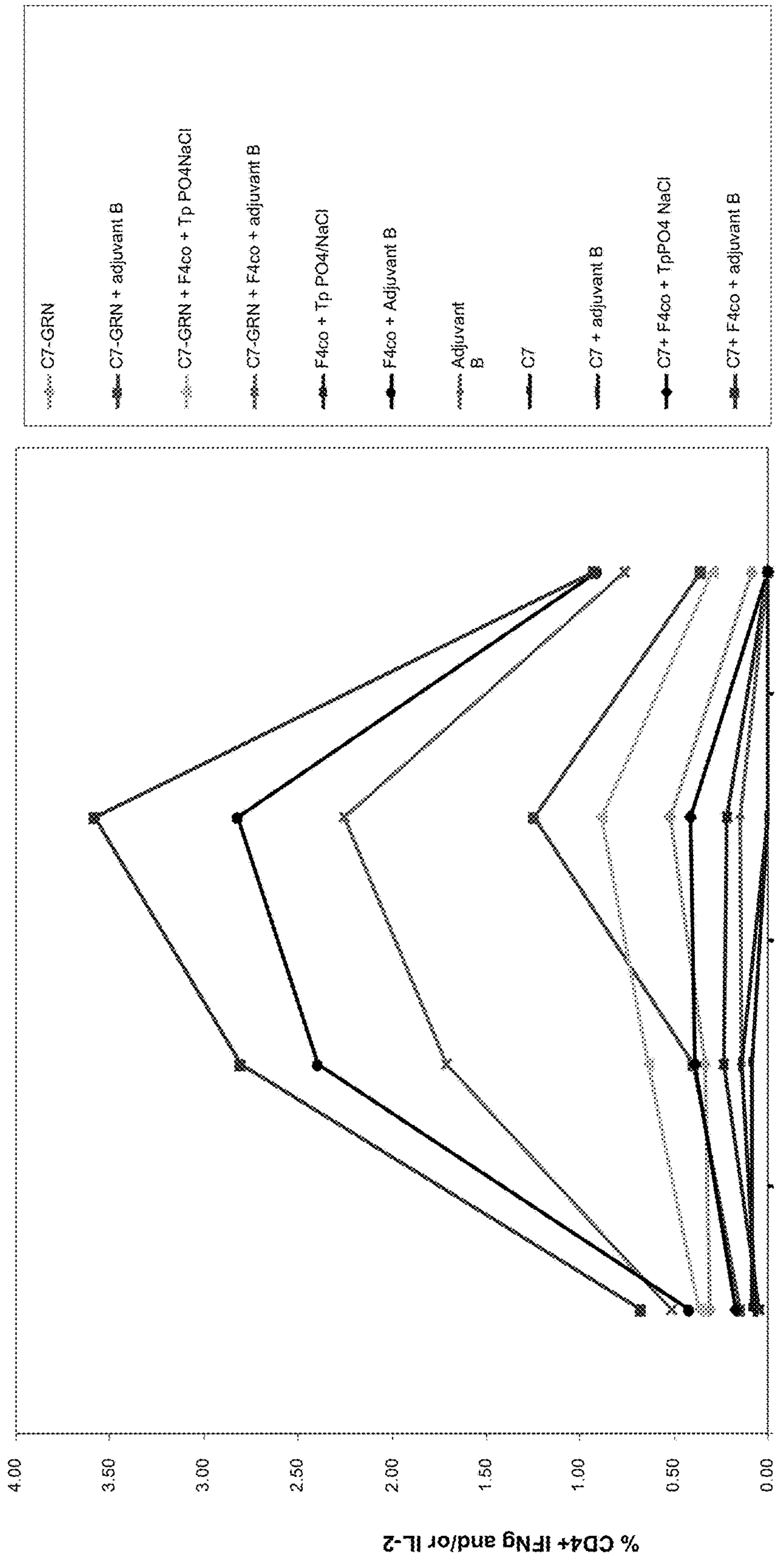
FIG. 13 shows the quantification of HIV-1-specific CD4 T cells.

The results are shown in the following figures:

FIG. 13. Quantification of HIV-1-specific CD4 T cells. The % of CD3 CD4 T cells secreting IFN-γ and/or IL-2 is represented for each protocol of immunization at four time-points. Peripheral blood lymphocytes (PBLs) were stimulated ex vivo (2 hours before addition of the Brefeldin then overnight) with a pool of peptides covering F4 sequence and the cytokine production was measured by ICS. Each value is the geometric mean of 5 pools of 3 mice.

Figure 14:
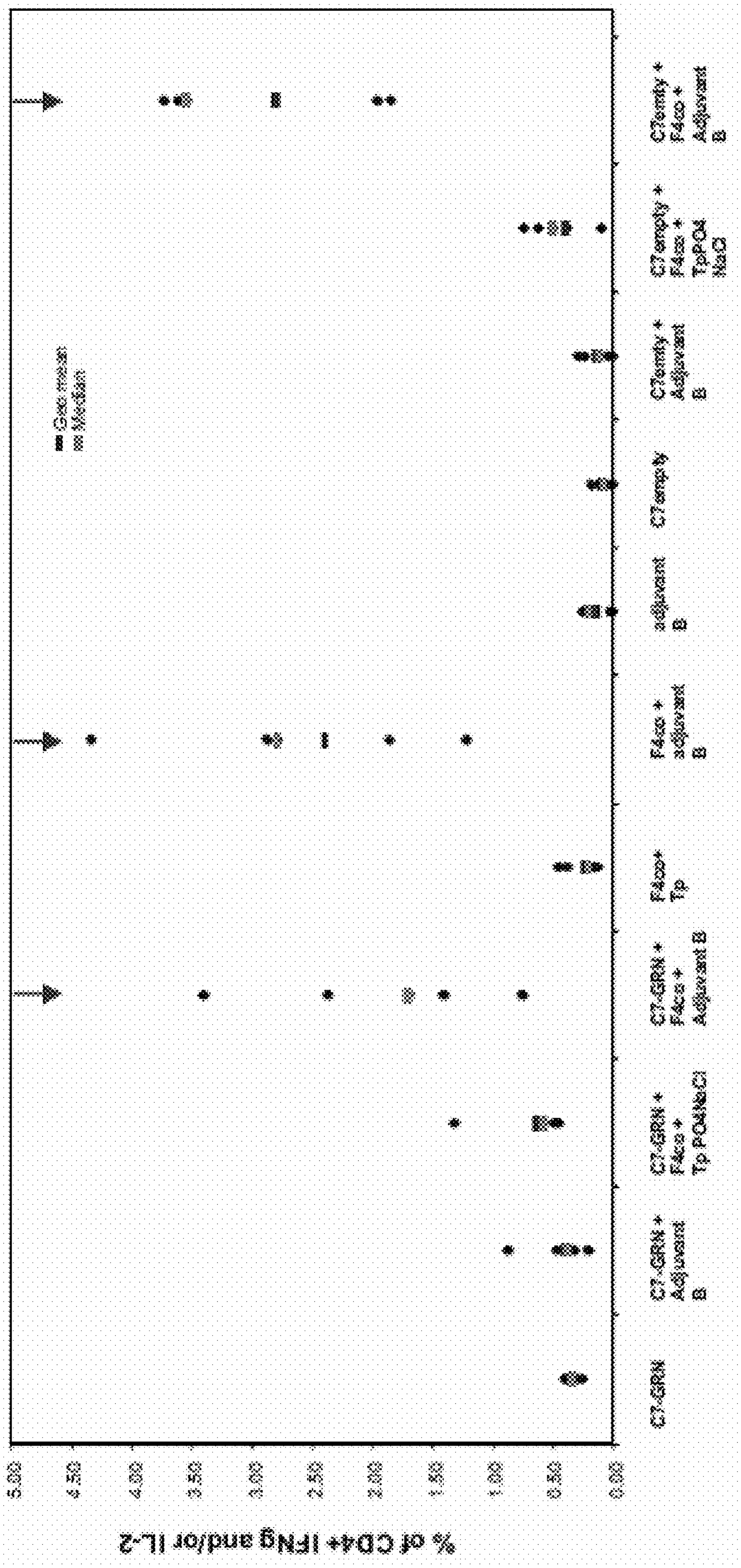
FIG. 14 shows distribution of the frequency of F4-specific CD4 T cells 7 days after two immunizations.

FIG. 14. Distribution of the frequency of F4-specific CD4 T cells 7 days after two immunizations. The frequency of F4-specific circulating CD4 T cells at 7 days after two immunizations is represented for each protocol. Each dot represents the value obtained for one pool of 3 mice.

Figure 15A:
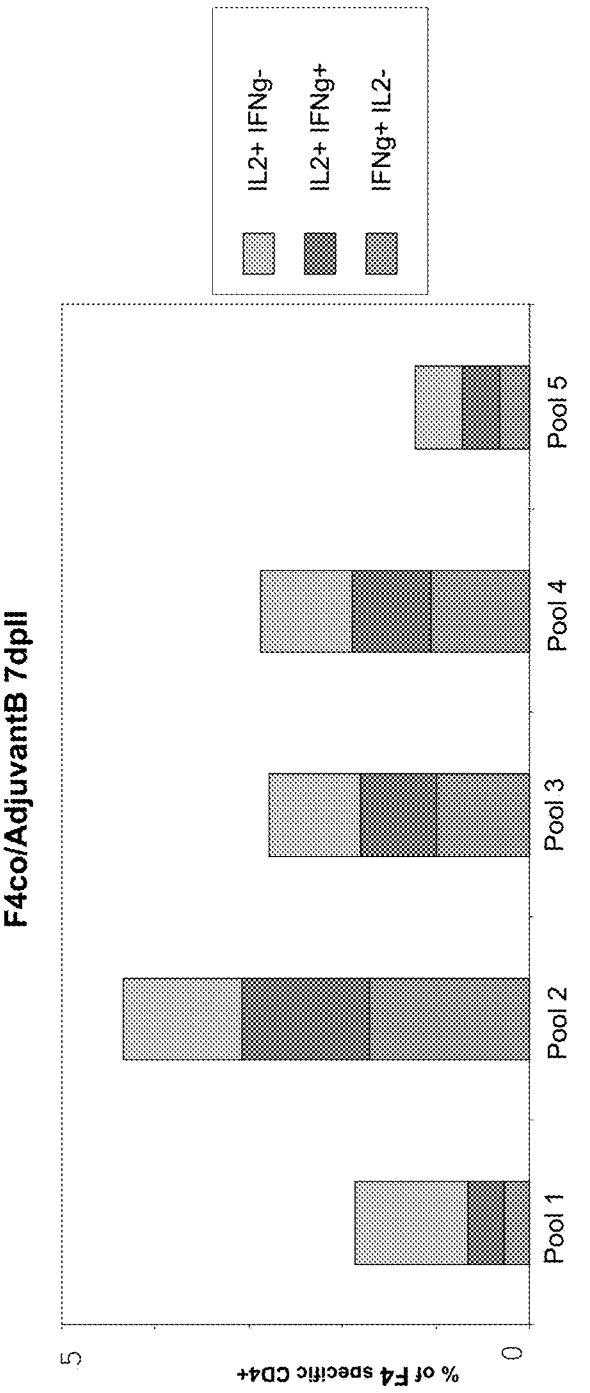
FIGS. 15A-15C show cytokine production of F4-specific CD4 T cells 7 days after two immunizations.
Figure 15B:
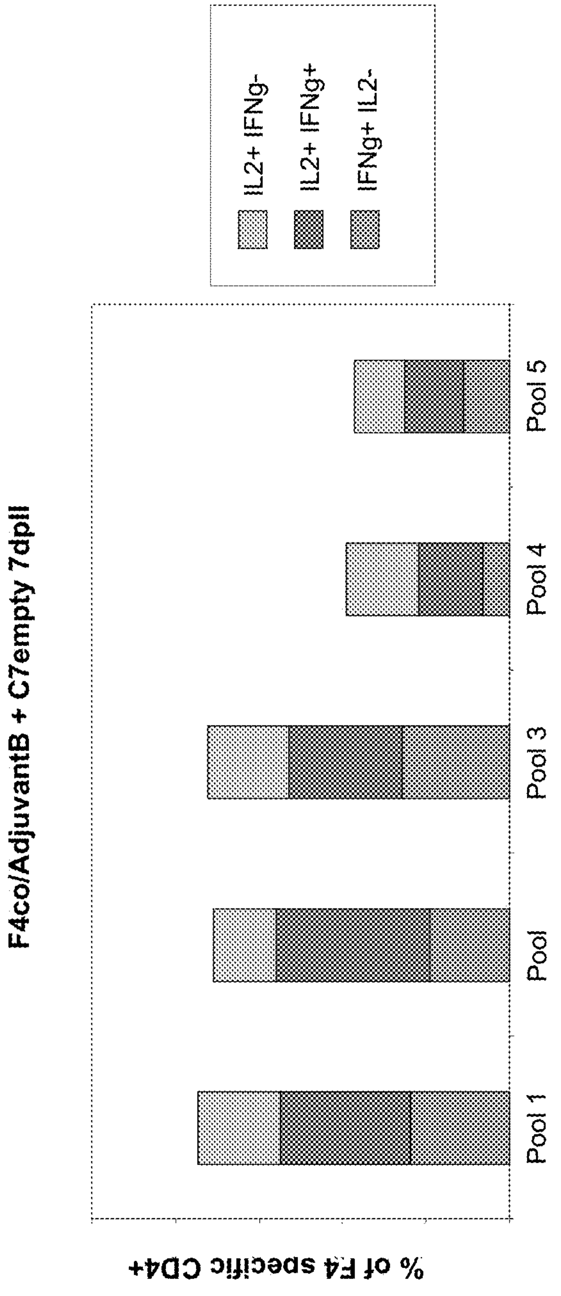
Figure 15C:
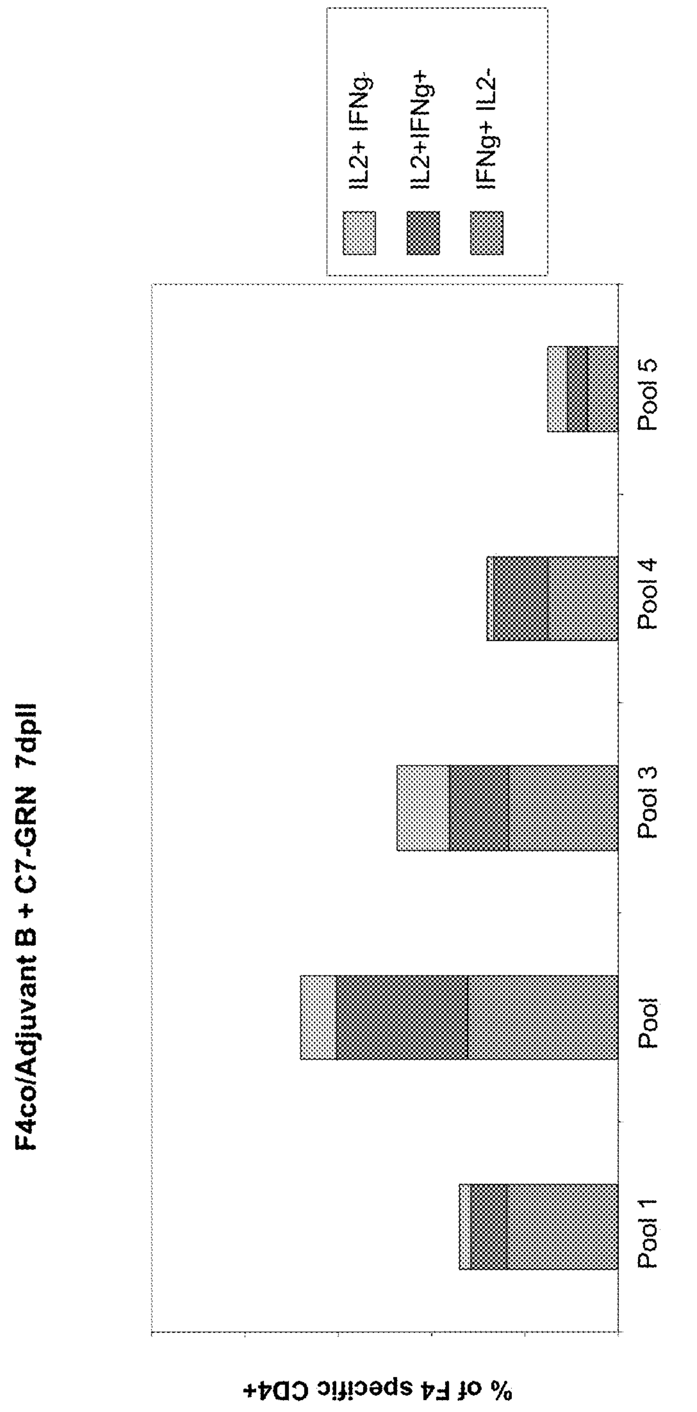

FIG. 15. Cytokine production of F4-specific CD4 T cells 7 days after two immunizations. The % of F4-specific CD4 T cells secreting IL-2 and/or IFN-γ is represented for 5 pools of 3 mice. Results for the immunization with F4co/adjuvant B (A), F4co/adjuvant B/C7 empty (B) and F4co/adjuvant B/C7-GRN (C) are presented.

The frequency of F4-specific circulating CD4 T cells reaches 2.82% 21 days after two immunizations with the F4co/adjuvant B combination and declines to 0.91% 56 days post-immunization (FIG. 13). Two doses of the C7-GRN virus alone result in 0.52% of F4-specific circulating CD4 T cells 21 days post last immunization and the presence of the adjuvant adjuvant B does not alter this response.

The presence of the empty vector C7 or the recombinant C7-GRN virus in addition of the F4co/adjuvant B mix does not increase nor interfere with the frequency of F4-specific CD4 T cell response (3.58% and 2.82% respectively, 21 days post-last immunization). Even if no statistical analysis has been performed, the population distribution suggests that the intensity of the F4-specific CD4 T cell responses is not different between the three protocols F4co/adjuvant B, F4co/adjuvant B/C7 empty and F4co/adjuvant B/C7-GRN (FIG. 14).

As expected, administration of the F4co without adjuvant B does not induce significant F4-specific CD4 T cells.

The profile of cytokine production shows that after immunization with F4co/adjuvant B, the F4-specific CD4 T cells secrete both IFN-γ and IL-2. Addition of C7empty or C7-GRN in the immunization protocol does not alter this profile.

As a result, these data suggest that the greatest F4-specific CD4 T cell response is obtained after immunization with the F4co/adjuvant B combination and that the presence of the C7-GRN virus does not improve nor alter this response.

Antigen-Specific CD8 T Cell Responses

The results are shown in the following figures

Figure 16:
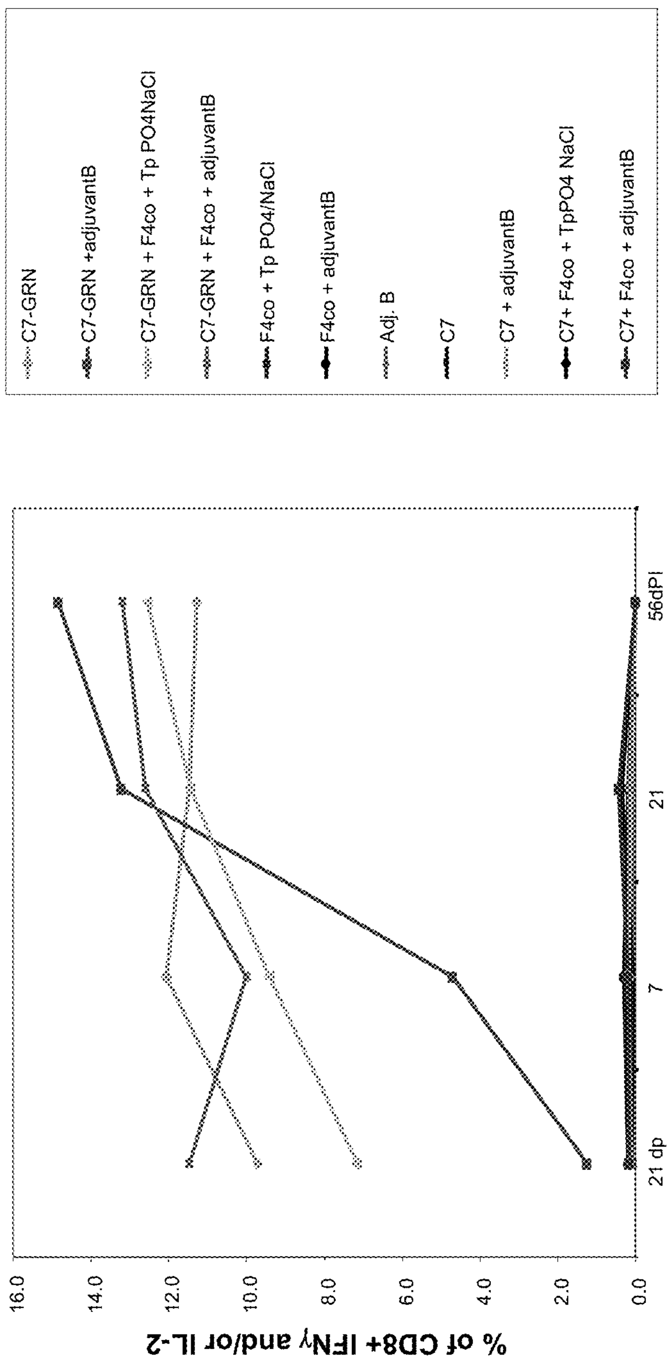
FIG. 16 shows quantification of HIV-1-specific CD8 T cells.

FIG. 16. Quantification of HIV-1-specific CD8 T cells. The % of CD3 CD8 T cells secreting IFN-γ and/or IL-2 is represented for each protocol of immunization at four time-points. Peripheral blood lymphocytes (PBLs) were stimulated ex vivo (2 hours before addition of Brefeldin then overnight) with a pool of peptides covering F4 and the cytokine production was measured by ICS. Each value is the geometric mean of 5 pools of 3 mice.

Figure 17A:
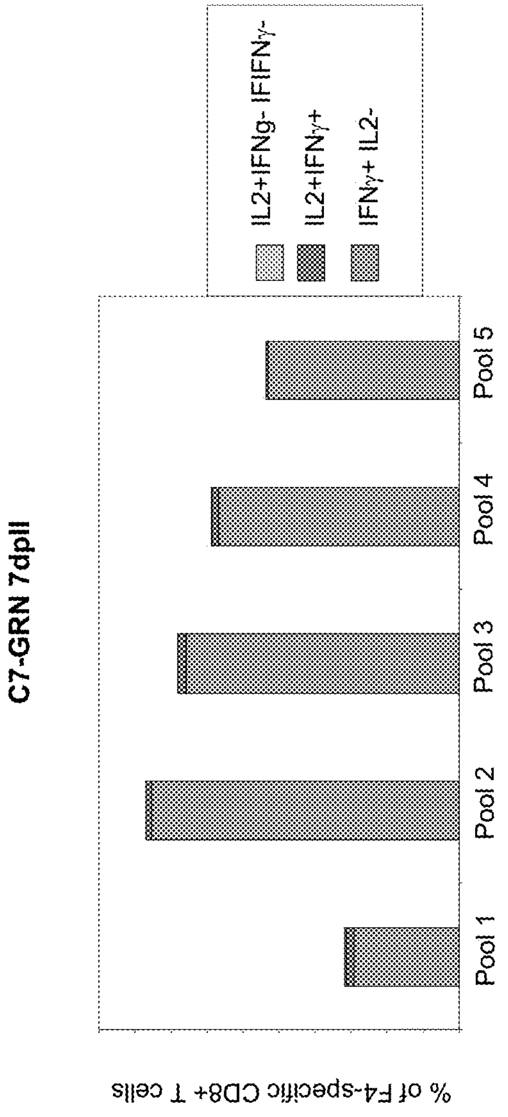
FIGS. 17A-17C show cytokine production of F4-specific CD8 T cells 7 days after two immunizations.
Figure 17B:
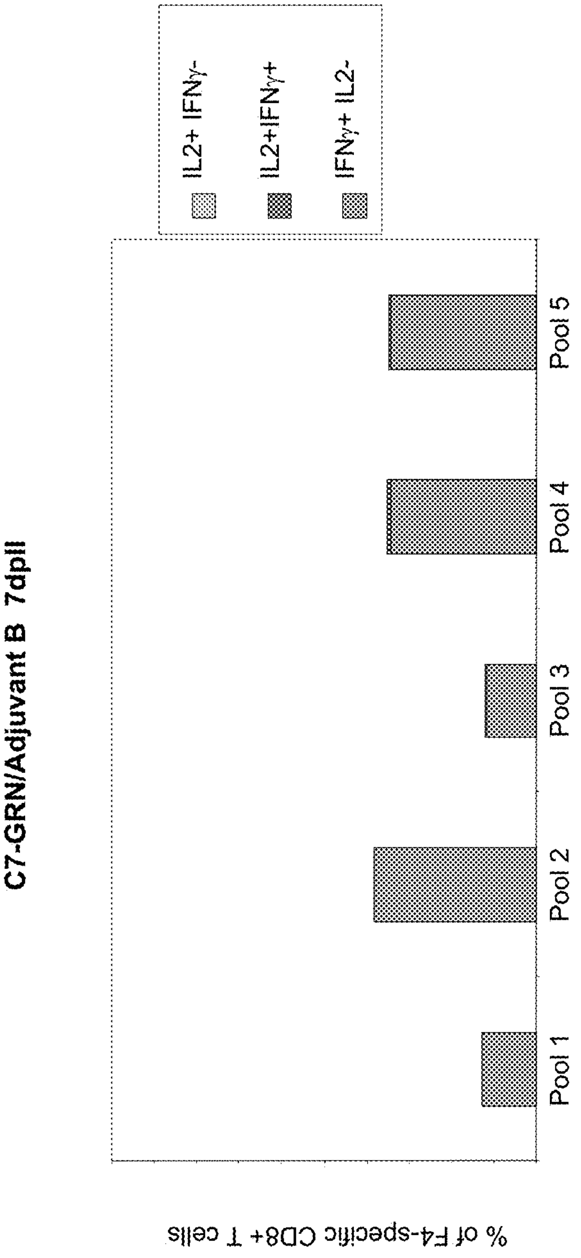
Figure 17C:
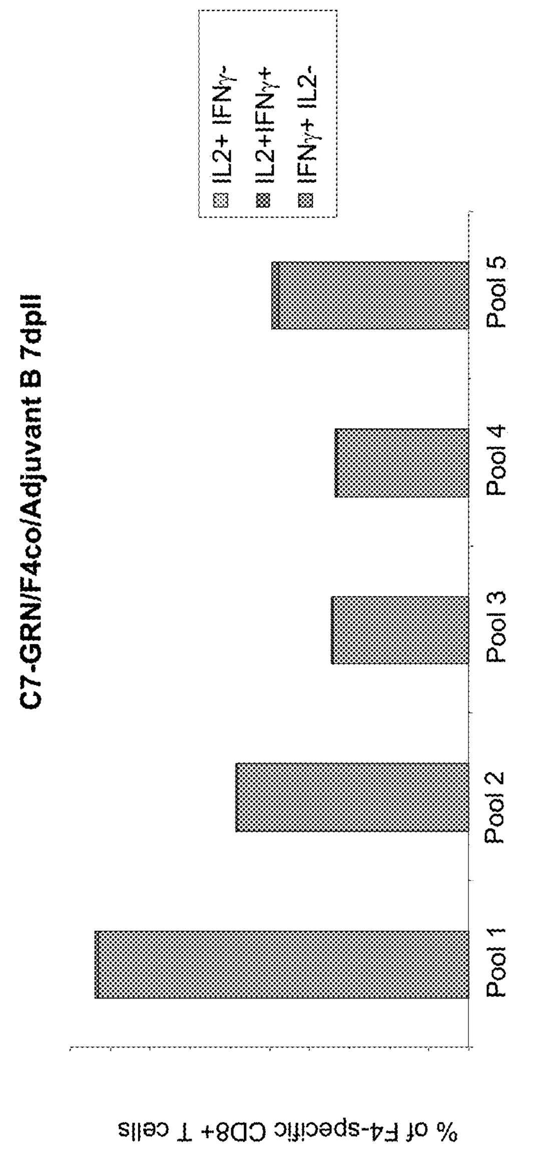

FIGS. 17A-17C Cytokine production of F4-specific CD8 T cells 7 days after two immunizations. The % of F4-specific CD8 T cells secreting IL-2 and/or IFN-γ is represented for 5 pools of 3 mice. Results for the immunization with C7-GRN (A), C7-GRN/adjuvant B (B) and C7-GRN+F4co/adjuvant B (C) are presented.

After one injection, the recombinant vector C7-GRN induces a high frequency of F4-specific circulating CD8 T cells (9.70% of total CD8 T cells, 21 days post-immunization) (FIG. 4). A second injection does not boost the F4-specific CD8 T cell response. The F4co/adjuvant B combination induces low to undetectable F4-specific CD8 T cells and adding this combination to the C7-GRN does not improve or impair the F4-specific CD8 T cell response.

The F4-specific CD8 T cell response is delayed when the adjuvant B is added to the C7-GRN, but reaches the same level as with the C7-GRN alone or the C7-GRN/F4co/adjuvant B combination at 21 days post-second immunization.

The F4-specific CD8 T cells mainly secrete IFN-γ whether the C7-GRN vector is injected alone or in combination with F4co/adjuvant B (FIGS. 17A-17C).

Interestingly, the F4-specific CD8 T cell response persists up to 56 days post-last immunization without declining, suggesting that the C7 vector elicits high and persistent CD8 T cells.

Conclusions

The F4co/adjuvant B vaccine induces a high frequency of poly-functional HIV-specific CD4 T cells but no HIV-specific CD8 T cells in CB6F1 mice. In the same animal model, the recombinant adenovirus C7 expressing Gag, RT and Nef (Ad C7-GRN) induces a high antigen-specific CD8 T cell response and low to undetectable antigen-specific CD4 T cells. A combination of F4/adjuvant B and Ad C7-GRN elicits both antigen-specific CD4 and CD8 T cells at the same time. A combination of three components, F4co, adjuvant B and C7-GRN elicits the highest levels of both antigen specific CD4 and CD8 T cells at the same time. Combining F4/adjuvant B and Ad C7-GRN has an additive effect concerning the intensity of both arms of the cellular immune response. The effect of the antigen-specific CD4 T cell response on the functionality of antigen-specific CD8 T cell response remains to be determined in this model.

Example 5

Immunogenicity of the Chimp adenovirus C7 Expressing CS2 Construct of CSP Protein from *Plasmodium falciparum* (C7-CS2) when Administered Alone Experimental Design:

CB6F1 mice were immunized once intramuscularly with a dose range ($10^{10}$, $10^9$ & $10^8$ viral particles) of the C7 chimp adenovirus expressing the CSP malaria antigen and the CSP-specific (C-term and N-term) CD4 and CD8 T cell responses were determined 21, 28 and 35 days post-injection by ICS (Intra-cellular Cytokine Staining).

CSP-Specific CD4 T Cell Responses

Figure 18:
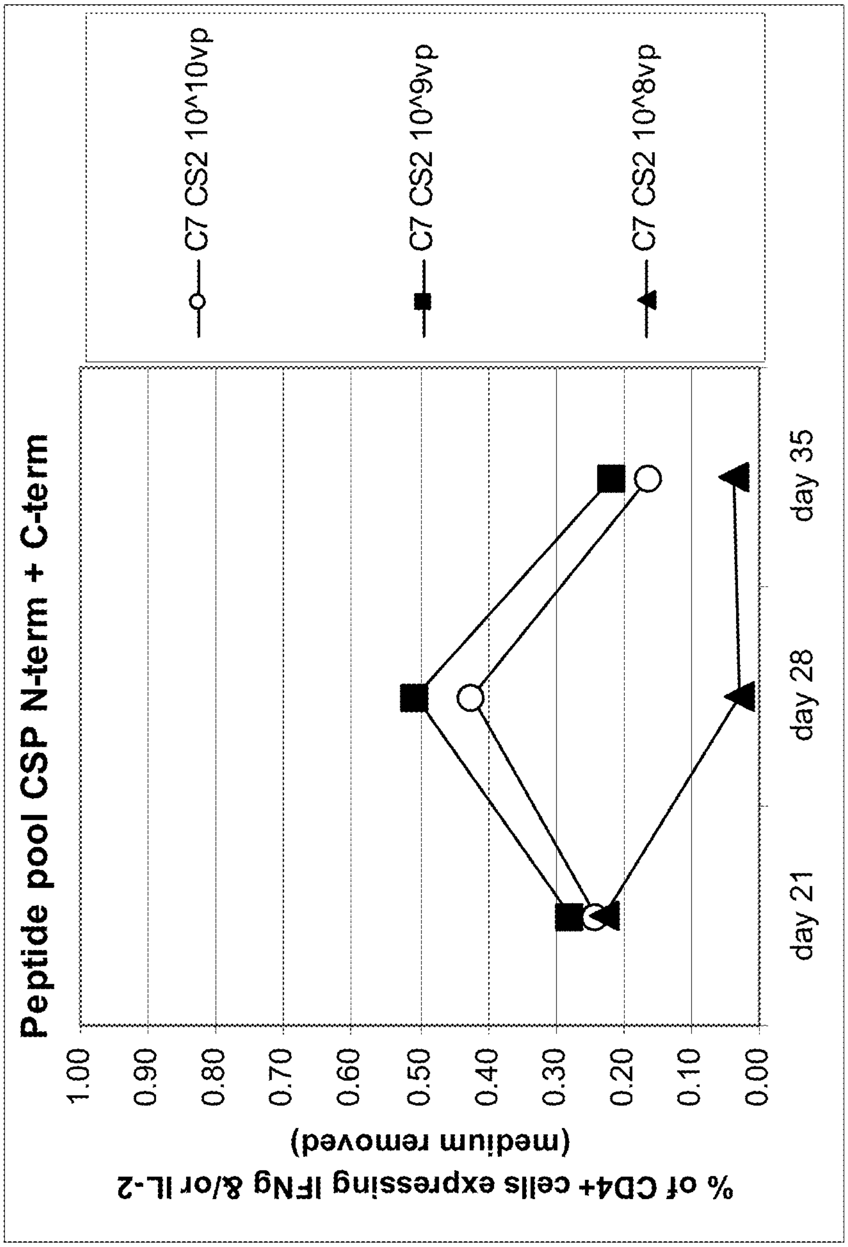
FIG. 18 shows quantification of CSP-specific CD4 T cells.

The results are shown in the following figures:

FIG. 18. Quantification of CSP-specific CD4 T cells. The % of CD4 T cells secreting IFN-γ and/or IL-2 is represented for each protocol of immunization at three time-points. Peripheral blood lymphocytes (PBLs) were stimulated ex vivo (2 hours before addition of the Brefeldin then overnight) with a pool of peptides covering CSP N-term or CSP C-term sequences and the cytokine production was measured by ICS. The responses to the C-term and N-term peptide pools were added up and each value is the average of 5 pools of 4 mice.

Figure 19:
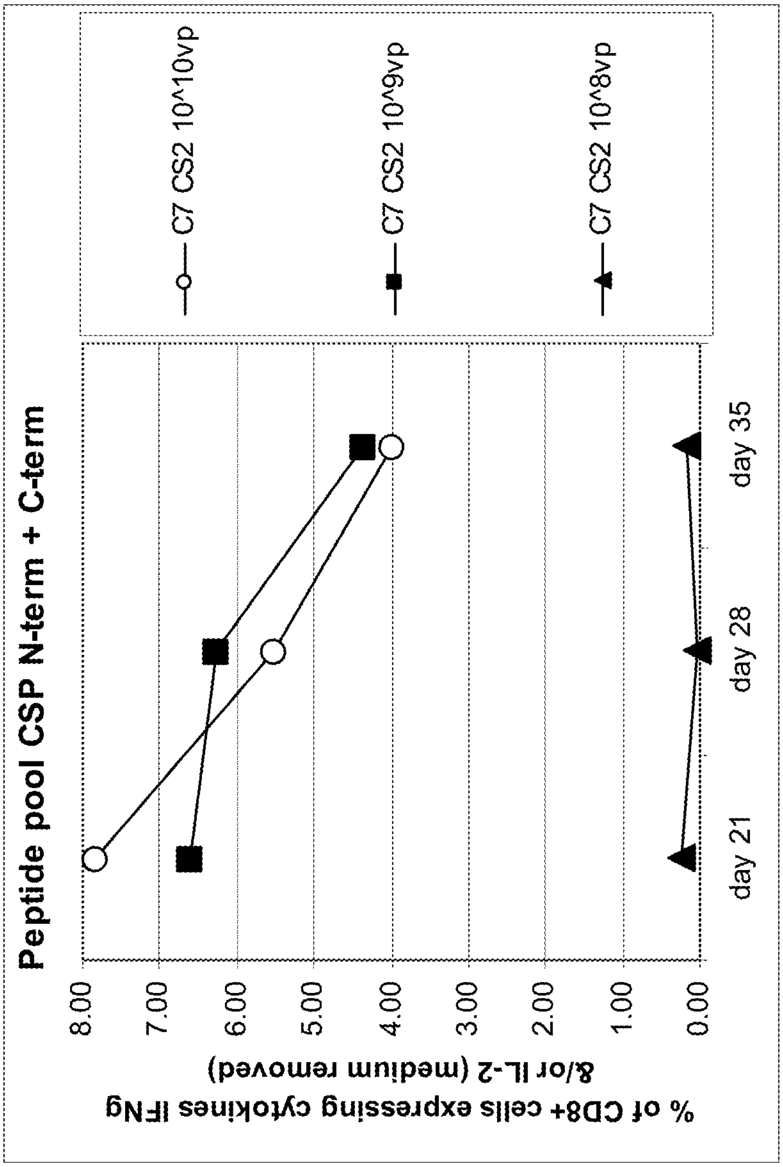
FIG. 19 shows quantification of CSP-specific CD8 T cells.

FIG. 19. Quantification of CSP-specific CD8 T cells. The % of CD8 T cells secreting IFN-γ and/or IL-2 is represented for each protocol of immunization at three time-points. Peripheral blood lymphocytes (PBLs) were stimulated ex vivo (2 hours before addition of the Brefeldin then overnight) with a pool of peptides covering CSP N-term or CSP C-term sequences and the cytokine production was measured by ICS. The responses to the C-term and N-term peptide pools were added up and each value is the average of 5 pools of 4 mice.

These results indicate that both $10^{10}$ and $10^9$ doses of C7-CS2 elicit similar levels of CSP-specific CD4 T cell responses (peak 0.5%) and similar levels of CSP-specific CD8 T cell responses (peak 8%). The dose of $10^{10}$ of C7-CS2 was chosen in subsequent experiments where the immunogenicity of C7-CS2 in combination with RTS,S was tested (see below).

Example 6

Immunogenicity of C7-CS2 and RTS,S when Administered as a Combination in CB6F1 Mice Experimental Design:

CB6F1 mice were immunized three times intramuscularly (day 0, 14 & 28) with either a combination of the malaria vaccine candidate RTS,S (5 μg) in 50 μl of Adjuvant B (referred as P-P-P in the figures below) or a combination of RTS,S (5 μg) and C7-CS2 ($10^{10}$ viral particles) in 50 μl of Adjuvant B (referred as C-C-C in the figures below). The CSP-specific (C-term and N-term) CD4 and CD8 T cell responses were determined at the following time-points:

- 7 days post 2 immunizations
- 7, 21, 35 and 49 days post 3 immunizations CSP-specific T cell responses were determined by ICS (Intra-cellular Cytokine Staining).

The CSP-specific antibody responses in the sera from immunized animals were also determined by ELISA at 14 and 42 days post-$3^{rd}$ immunization.

CSP-Specific CD4 T Cell Responses

Figure 20:
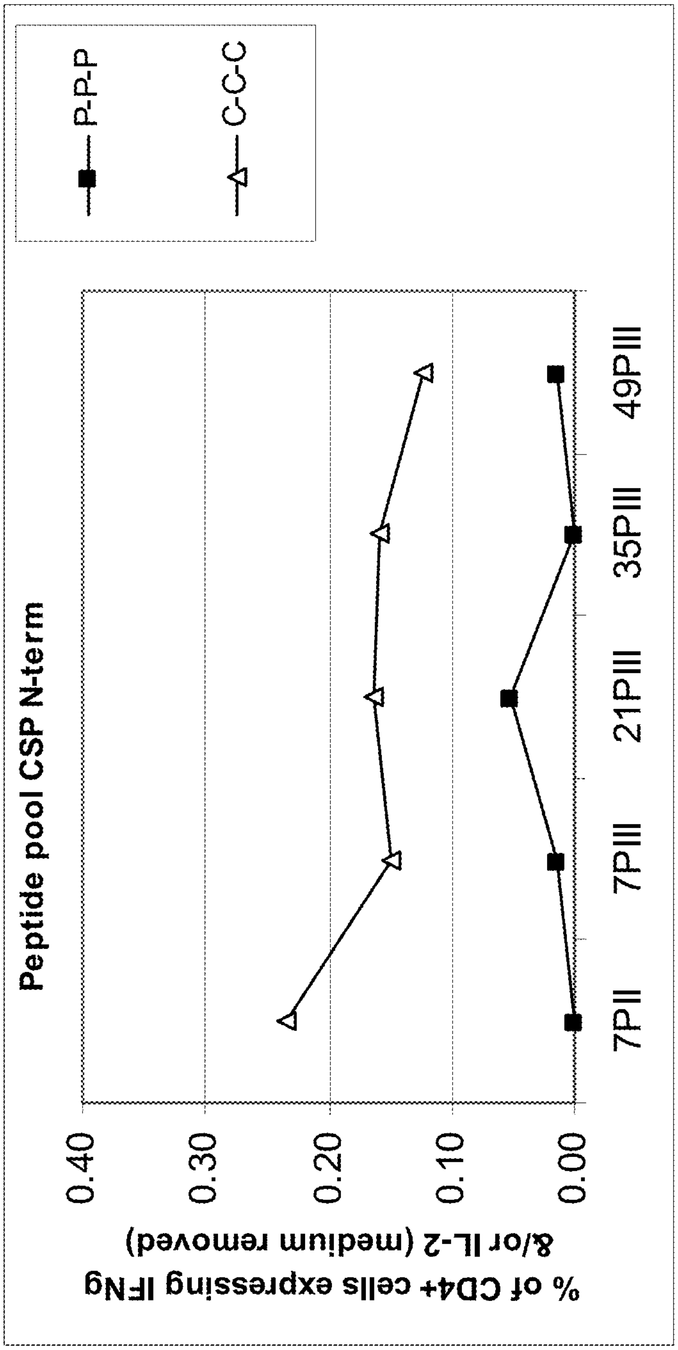
FIG. 20 shows quantification of CSP(N-term)-specific CD4 T cells.

The results are shown in the following figures:

FIG. 20. Quantification of CSP(N-term)-specific CD4 T cells. The % of CD4 T cells secreting IFN-γ and/or IL-2 is represented for each protocol of immunization at five time-points. Peripheral blood lymphocytes (PBLs) were stimulated ex vivo (2 hours before addition of the Brefeldin then overnight) with a pool of peptides covering the CSP N-term sequence and the cytokine production (IFN-γ and/or IL-2) was measured by ICS. Each value is the average of 4 pools of 7 mice.

Figure 21:
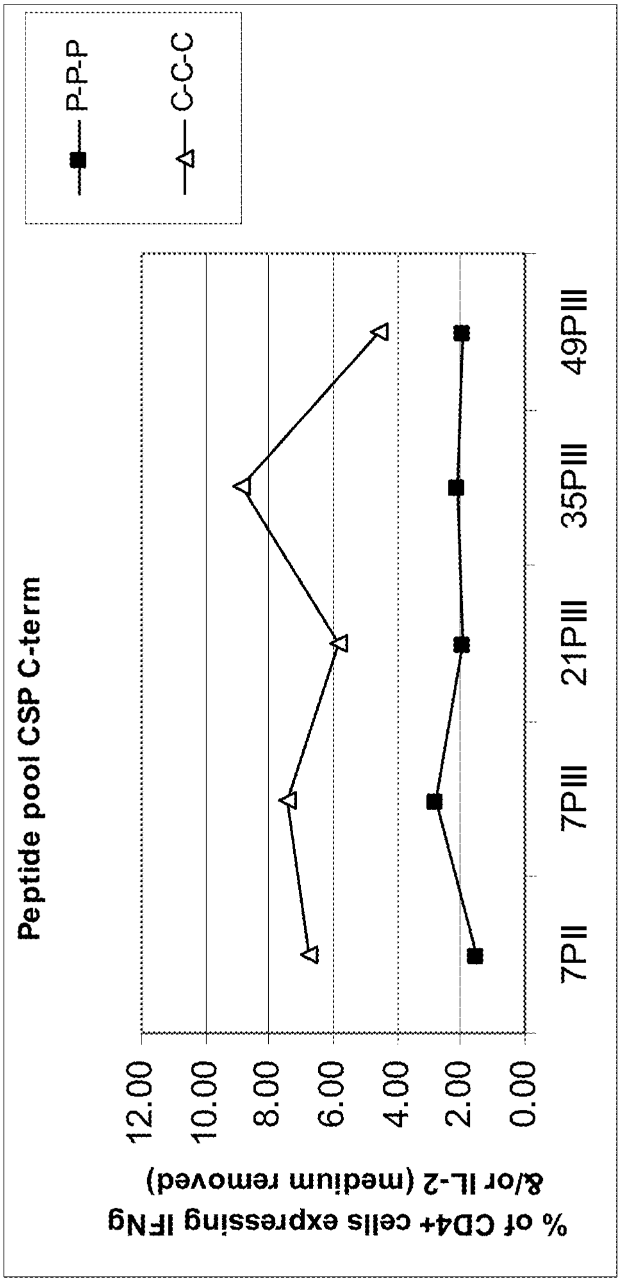
FIG. 21 shows quantification of CSP(C-term)-specific CD4 T cells.

FIG. 21. Quantification of CSP(C-term)-specific CD4 T cells. The % of CD4 T cells secreting IFN-γ and/or IL-2 is represented for each protocol of immunization at five time-points. Peripheral blood lymphocytes (PBLs) were stimulated ex vivo (2 hours before addition of the Brefeldin then overnight) with a pool of peptides covering the CSP C-term sequence and the cytokine production (IFN-γ and/or IL-2) was measured by ICS. Each value is the average of 4 pools of 7 mice.

These results indicate that mice immunized with 3 injections of the combination [RTS,S+C7-CS2 $10^{10}$+Adjuvant B] display higher antigen-specific CD4 T cell responses (both against the C-term and N-term part of CSP) than the mice immunized with 3 injections of RTS,S+Adjuvant B.

CSP-Specific CD8 T Cell Responses

Figure 22:
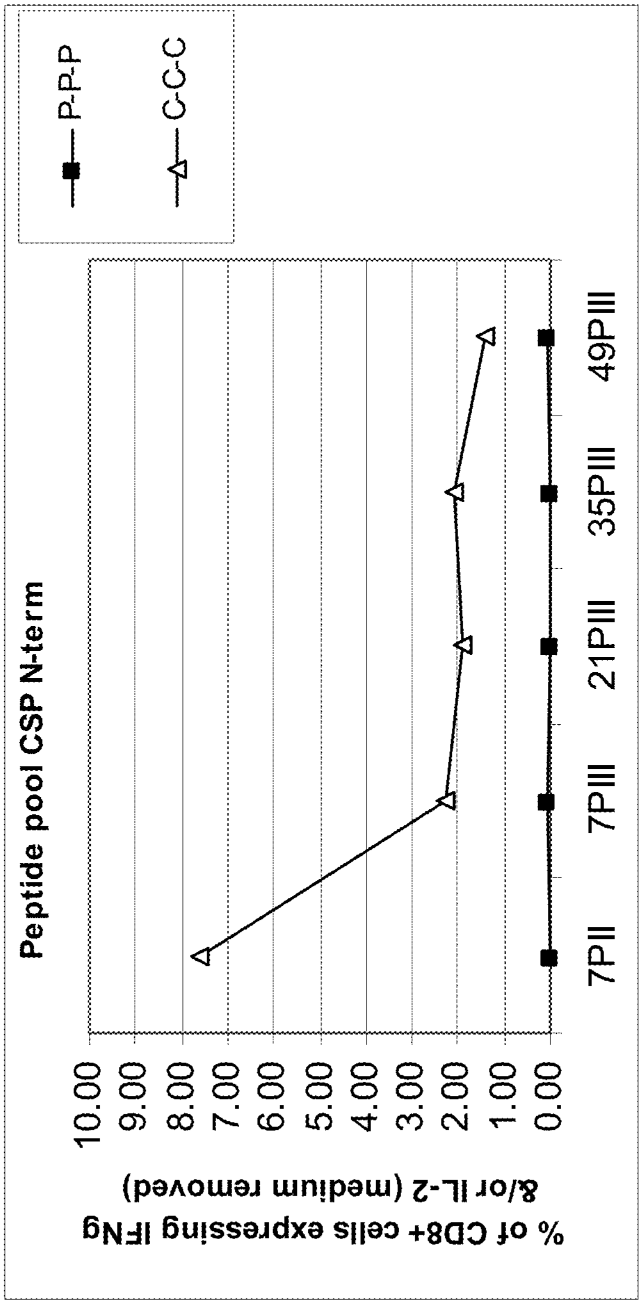
FIG. 22 shows quantification of CSP(N-term)-specific CD8 T cells.

The results are shown in the following figures:

FIG. 22. Quantification of CSP(N-term)-specific CD8 T cells. The % of CD8 T cells secreting IFN-γ and/or IL-2 is represented for each protocol of immunization at five time-points. Peripheral blood lymphocytes (PBLs) were stimulated ex vivo (2 hours before addition of the Brefeldin then overnight) with a pool of peptides covering the CSP N-term sequence and the cytokine production (IFN-γ and/or IL-2) was measured by ICS. Each value is the average of 4 pools of 7 mice.

Figure 23:
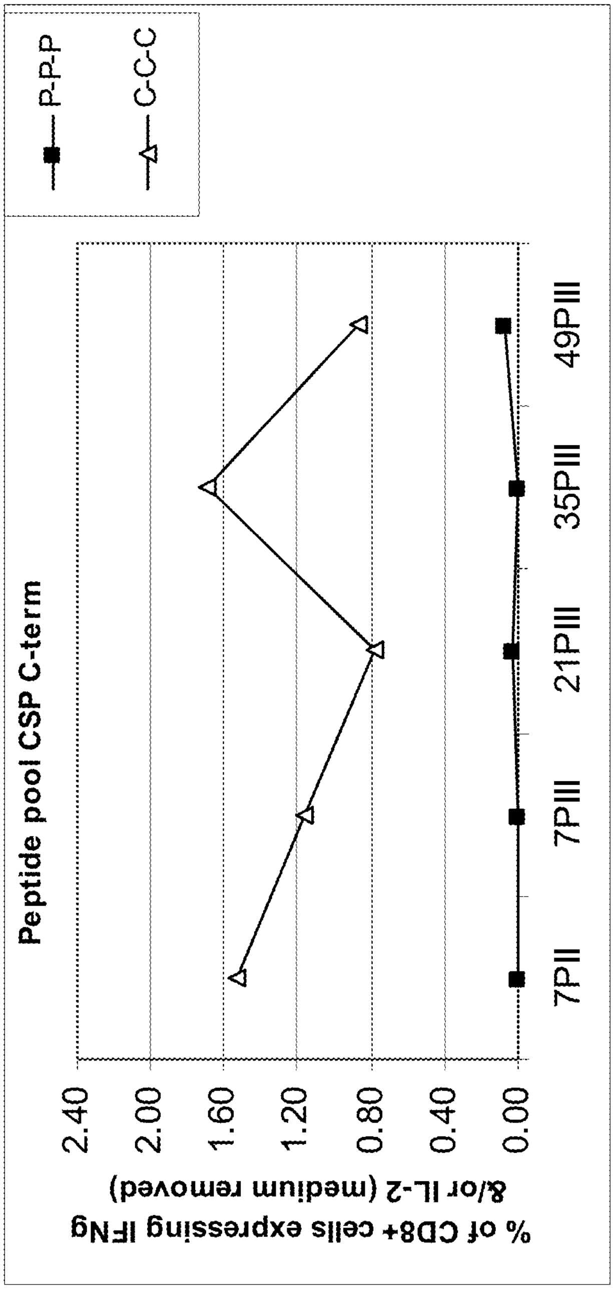
FIG. 23 shows quantification of CSP(C-term)-specific CD8 T cells.

FIG. 23. Quantification of CSP(C-term)-specific CD8 T cells. The % of CD8 T cells secreting IFN-γ and/or IL-2 is represented for each protocol of immunization at five time-points. Peripheral blood lymphocytes (PBLs) were stimulated ex vivo (2 hours before addition of the Brefeldin then overnight) with a pool of peptides covering the CSP C-term sequence and the cytokine production (IFNg and/or IL-2) was measured by ICS. Each value is the average of 4 pools of 7 mice.

These results indicate that mice immunized with 3 injections of the combination [RTS,S+C7-CS2 $10^{10}$+Adjuvant B] display higher antigen-specific CD8 T cell responses (both against the C-term and N-term part of CSP) than the mice immunized with 3 injections of RTS,S+Adjuvant B.

CSP-Specific Antibody Responses

Figure 24:
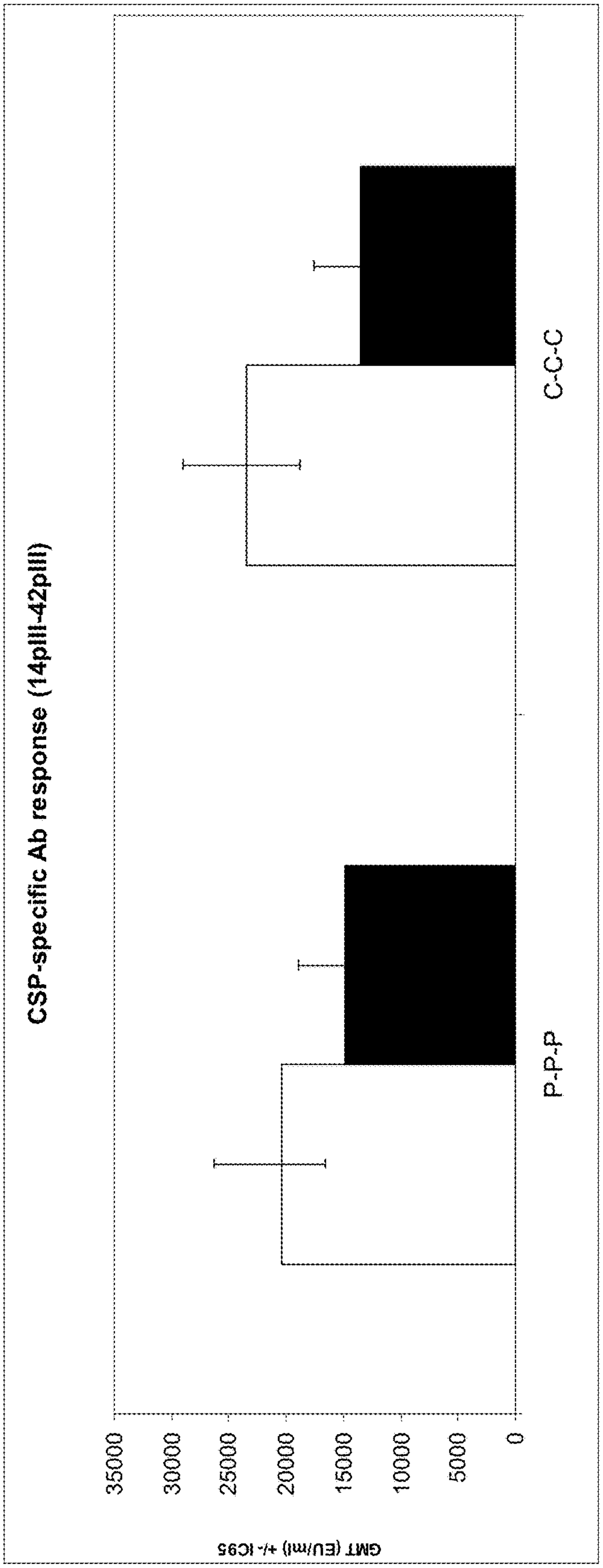
FIG. 24 shows quantification of CSP-specific antibody titers.

The results are shown in the following figure:

FIG. 24. Quantification of CSP-specific antibody titers. The sera from the mice were collected at 14 and 42 days post $3^{rd}$ immunization. The anti-CSP antibody titers were measured in each of these individual sera by ELISA. The data shown is the geometric mean antibody titers±95% confidence interval.

These results indicate that mice immunized with 3 injections of the combination [RTS,S+C7-CS2 $10^{10}$+Adjuvant B] display similar CSP-specific antibody titers than the mice immunized with 3 injections of RTS,S+Adjuvant B.

Conclusions

The RTS,S/adjuvant B vaccine induces a high frequency of CSP C-term-specific CD4 T cells but no CSP N-term specific CD4 T cells. In addition, the RTS,S/adjuvant B vaccine induces low to undetectable CSP C& N-term specific CD8 T cells. In the same animal model, the recombinant adenovirus C7 expressing CSP induces high CSP(C-term and N-term)-specific CD8 T cell responses and lower CSP(C-term and N-term)-specific CD4 T cell responses. A combination of RTS,S/adjuvant B and Ad C7-CS2 elicits high levels of both CSP(C-term and N-term)-specific CD4 and CD8 T cells at the same time. Combining RTS,S/adjuvant B and Ad C7-CS2 has an additive effect concerning the intensity of both arms of the T cell response. Finally, the combination of RTS,S/adjuvant B and Ad C7-CS2 elicits high levels of CSP-specific antibody responses that are comparable to the ones induced by RTS,S/adjuvant B.

SEQUENCE

SEQ ID No 1:
1 atgggtgccc gagcttcggt actgtctggt ggagagctgg acagatggga
51 gaaaattagg ctgcgcccgg gaggcaaaaa gaaatacaag ctcaagcata
101 tcgtgtgggc ctcgagggag cttgaacggt ttgccgtgaa cccaggcctg
151 ctggaaacat ctgagggatg tcgccagatc ctggggcaat tgcagccatc
201 cctccagacc gggagtgaag agctgaggtc cttgtataac acagtggcta
251 ccctctactg cgtacaccag aggatcgaga ttaaggatac caaggaggcc
301 ttggacaaaa ttgaggagga gcaaaacaag agcaagaaga aggcccagca
351 ggcagctgct gacactgggc atagcaacca ggtatcacag aactatccta
401 ttgtccaaaa cattcagggc cagatggttc atcaggccat cagcccccgg
451 acgctcaatg cctgggtgaa ggttgtcgaa gagaaggcct tttctcctga
501 ggttatcccc atgttctccg ctttgagtga gggggccact cctcaggacc
551 tcaatacaat gcttaatacc gtgggcggcc atcaggccgc catgcaaatg
601 ttgaaggaga ctatcaacga ggaggcagcc gagtgggaca gagtgcatcc
651 cgtccacgct ggcccaatcg cgcccggaca gatgcgggag cctcgcggct
701 ctgacattgc cggcaccacc tctacactgc aagagcaaat cggatggatg
751 accaacaatc ctcccatccc agttggagaa atctataaac ggtggatcat
801 cctgggcctg aacaagatcg tgcgcatgta ctctccgaca tccatccttg
851 acattagaca gggacccaaa gagcctttta gggattacgt cgaccggttt
901 tataagaccc tgcgagcaga gcaggcctct caggaggtca aaaactggat
951 gacggagaca ctcctggtac agaacgctaa ccccgactgc aaaacaatct
1001 tgaaggcact aggcccggct gccaccctgg aagagatgat gaccgcctgt
1051 cagggagtag gcggacccgg acacaaagcc agagtgttga tgggccccat
1101 cagtcccatc gagaccgtgc cggtgaagct gaaacccggg atggacggcc
1151 ccaaggtcaa gcagtggcca ctcaccgagg agaagatcaa ggccctggtg
1201 gagatctgca ccgagatgga gaaagagggc aagatcagca agatcgggcc
1251 ggagaaccca tacaacaccc ccgtgtttgc catcaagaag aaggacagca
1301 ccaagtggcg caagctggtg gatttccggg agctgaataa gcggacccag
1351 gatttctggg aggtccagct gggcatcccc catccggccg gcctgaagaa
1401 gaagaagagc gtgaccgtgc tggacgtggg cgacgcttac ttcagcgtcc
1451 ctctggacga ggactttaga aagtacaccg cctttaccat cccatctatc
1501 aacaacgaga cccctggcat cagatatcag tacaacgtcc tcccccaggg
1551 ctggaagggc tctcccgcca ttttccagag ctccatgacc aagatcctgg
1601 agccgtttcg gaagcagaac cccgatatcg tcatctacca gtacatggac
1651 gacctgtacg tgggctctga cctggaaatc gggcagcatc gcacgaagat
1701 tgaggagctg aggcagcatc tgctgagatg ggggcctgacc actccggaca
1751 agaagcatca gaaggagccg ccattcctga agatgggcta cgagctccat
1801 cccgacaagt ggaccgtgca gcctatcgtc ctccccgaga aggacagctg
1851 gaccgtgaac gacatccaga agctggtggg caagctcaac tgggctagcc
1901 agatctatcc cgggatcaag gtgcgccagc tctgcaagct gctgcgcggc
1951 accaaggccc tgaccgaggt gattcccctc acggaggaag ccgagctcga
2001 gctggctgag aaccgggaga tcctgaagga gcccgtgcac ggcgtgtact
2051 atgacccctc caaggacctg atcgccgaaa tccagaagca gggccagggg
2101 cagtggacat accagattta ccaggagcct ttcaagaacc tcaagaccgg
2151 caagtacgcc cgcatgaggg gcgcccacac caacgatgtc aagcagctga
2201 ccgaggccgt ccagaagatc acgaccgagt ccatcgtgat ctgggggaag
2251 acacccaagt tcaagctgcc tatccagaag gagacctggg agacgtggtg
2301 gaccgaatat tggcaggcca cctggattcc cgagtgggag ttcgtgaata
2351 cacctcctct ggtgaagctg tggtaccagc tcgagaagga gcccatcgtg
2401 ggcgcggaga cattctacgt ggacggcgcg gccaaccgcg aaacaaagct
2451 cgggaaggcc gggtacgtca ccaaccgggg ccgccagaag gtcgtcaccc
2501 tgaccgacac caccaaccag aagacggagc tgcaggccat ctatctcgct
2551 ctccaggact ccggcctgga ggtgaacatc gtgacggaca gccagtacgc
2601 gctgggcatt attcaggccc agccggacca gtccgagagc gaactggtga
2651 accagattat cgagcagctg atcaagaaag agaaggtcta cctcgcctgg
2701 gtcccggccc ataagggcat tggcggcaac gagcaggtcg acaagctggt
2751 gagtgcgggg attagaaagg tgctgatggt gggttttcca gtcacacctc
2801 aggtaccttt aagaccaatg acttacaagg cagctgtaga tcttagccac
2851 tttttaaaag aaaagggggg actggaaggg ctaattcact cccaaagaag
2901 acaagatatc cttgatctgt ggatctacca cacacaaggc tacttccctg
2951 attggcagaa ctacacacca gggccagggg tcagatatcc actgaccttt
3001 ggatggtgct acaagctagt accagttgag ccagataagg tagaagaggc
3051 caataaagga gagaacacca gcttgttaca ccctgtgagc ctgcatggga
3101 tggatgaccc ggagagagaa gtgttagagt ggaggtttga cagccgccta
3151 gcatttcatc acgtggcccg agagctgcat ccggagtact tcaagaactg
3201 ctga SEQ ID No 2:
1 MGARASVLSG GELDRWEKIR LRPGGKKKYK LKHIVWASRE LERFAVNPGL
51 LETSEGCRQI LGQLQPSLQT GSEELRSLYN TVATLYCVHQ RIEIKDTKEA
101 LDKIEEEQNK SKKKAQQAAA DTGHSNQVSQ NYPIVQNIQG QMVHQAISPR
151 TLNAWVKVVE EKAFSPEVIP MFSALSEGAT PQDLNTMLNT VGGHQAAMQM
201 LKETINEEAA EWDRVHPVHA GPIAPGQMRE PRGSDIAGTT STLQEQIGWM
251 TNNPPIPVGE IYKRWIILGL NKIVRMYSPT SILDIRQGPK EPFRDYVDRF
301 YKTLRAEQAS QEVKNWMTET LLVQNANPDC KTILKALGPA ATLEEMMTAC
351 QGVGGPGHKA RVLMGPISPI ETVPVKLKPG MDGPKVKQWP LTEEKIKALV
401 EICTEMEKEG KISKIGPENP YNTPVFAIKK KDSTKWRKLV DFRELNKRTQ
451 DFWEVQLGIP HPAGLKKKKS VTVLDVGDAY FSVPLDEDFR KYTAFTIPSI
501 NNETPGIRYQ YNVLPQGWKG SPAIFQSSMT KILEPFRKQN PDIVIYQYMD -continued

SEQUENCE

551 DLYVGSDLEI GQHRTKIEEL RQHLLRWGLT TPDKKHQKEP PFLKMGYELH
601 PDKWTVQPIV LPEKDSWTVN DIQKLVGKLN WASQIYPGIK VRQLCKLLRG
651 TKALTEVIPL TEEAELELAE NREILKEPVH GVYYDPSKDL IAEIQKQGQG
701 QWTYQIYQEP FKNLKTGKYA RMRGAHTNDV KQLTEAVQKI TTESIVIWGK
751 TPKFKLPIQK ETWETWWTEY WQATWIPEWE FVNTPPLVKL WYQLEKEPIV
801 GAETFYVDGA ANRETKLGKA GYVTNRGRQK VVTLTDTTNQ KTELQAIYLA
851 LQDSGLEVNI VTDSQYALGI IQAQPDQSES ELVNQIIEQL IKKEKVYLAW
901 VPAHKGIGGN EQVDKLVSAG IRKVLMVGFP VTPQVPLRPM TYKAAVDLSH
951 FLKEKGGLEG LIHSQRRQDI LDLWIYHTQG YFPDWQNYTP GPGVRYPLTF
1001 GWCYKLVPVE PDKVEEANKG ENTSLLHPVS LHGMDDPERE VLEWRFDSRL
1051 AFHHVARELH PEYFKNC

SEQ ID No 3:
1 atggccgcca gagccagcat cctgagcggg ggcaagctgg acgcctggga
51 gaagatcaga ctgaggcctg gcggcaagaa gaagtaccgg ctgaagcacc
101 tggtgtgggc cagcagagag ctggatcgct tcgccctgaa tcctagcctg
151 ctggagacca ccgagggctg ccagcagatc atgaaccagc tgcagcccgc
201 cgtgaaaacc ggcaccgagg agatcaagag cctgttcaac accgtggcca
251 ccctgtactg cgtgcaccag cggatcgacg tgaaggatac caaggaggcc
301 ctggacaaga tcgaggagat ccagaacaag agcaagcaga aaacccagca
351 ggccgctgcc gacaccggcg acagcagcaa agtgagccag aactacccca
401 tcatccagaa tgcccagggc cagatgatcc accagaacct gagccccaga
451 accctgaatg cctgggtgaa agtgatcgag gaaaaggcct tcagccccga
501 agtgatccct atgttcagcg ccctgagcga gggcgccacc ccccaggacc
551 tgaacgtgat gctgaacatt gtgggcggac accaggccgc catgcagatg
601 ctgaaggaca ccatcaatga ggaggccgcc gagtgggaca gactgcaccc
651 cgtgcaggcc ggacccatcc cccctggcca gatcagagag cccagaggca
701 gcgacatcgc cggcaccacc tccacccctc aagaacagct gcagtggatg
751 accggcaacc ctcccatccc tgtgggcaac atctacaagc ggtggatcat
801 cctgggcctg aacaagattg tgcggatgta cagccccgtg tccatcctgg
851 atatcaagca gggccccaag gagcccttca gagactacgt ggaccggttc
901 ttcaaggccc tgagagccga gcaggccacc caggacgtga agggctggat
951 gaccgagacc ctgctggtgc agaacgccaa ccccgactgc aagagcatcc
1001 tgaaggccct gggcagcggc gccacactgg aggagatgat gaccgcctgc
1051 cagggagtgg gcggacccgg ccacaaggcc agagtgctgg ccgaggccat
1101 gagccaggcc cagcagacca acatcatgat gcagcggggc aacttcagag
1151 gccagaagcg gatcaagtgc ttcaactgcg gcaaggaggg ccacctggcc
1201 agaaactgca gagcccccag gaagaagggc tgctggaagt gtggcaagga
1251 agggcaccag atgaaggact gcaccgagag gcaggccaat ttcctgggca
1301 agatttggcc tagcagcaag ggcagacccg gcaatttccc ccagagcaga
1351 cccgagccca ccgcccctcc cgccgagctg ttcggcatgg gcgagggcat
1401 cgccagcctg cccaagcagg agcagaagga cagagagcag gtgccccccc
1451 tggtgtccct gaagtccctg ttcggcaacg atcctctgag ccagggatcc
1501 cccatcagcc ccatcgagac cgtgcccgtg accctgaagc ccggcatgga
1551 tggccccaaa gtgaaacagt ggcccctgac cgaggagaag attaaggccc
1601 tgaccgaaat ctgtaccgag atggagaagg agggcaagat cagcaagatc
1651 ggcccccgaga acccctacaa cacccccatc ttcgccatca agaagaagga
1701 cagcaccaag tggcggaaac tggtggactt ccgggagctg aacaagagga
1751 cccaggactt ctgggaagtg cagctgggca tcccccaccc tgccggcctg
1801 aagaagaaga agtccgtgac agtgctggat gtgggcgacg cctacttcag
1851 cgtgcccctg gacgagaact tcaggaagta caccgccttc accatcccca
1901 gcaccaacaa cgagaccccc ggagtgagat accagtacaa cgtgctgcct
1951 cagggctgga agggcagccc cgccatcttc cagagcagca tgaccaagat
2001 cctggagccc ttccggagca agaaccccga gatcatcatc taccagtaca
2051 tggccgccct gtatgtgggc agcgatctgg agatcggcca gcacaggacc
2101 aagatcgaag agctgagggc ccacctgctg agctggggct tcaccacccc
2151 cgataagaag caccagaagg agccccctttt cctgtggatg ggctacgagc
2201 tgcaccccga taagtggacc gtgcagccca tcatgctgcc cgataaggag
2251 agctggaccg tgaacgacat ccagaaactg gtgggcaagc tgaattgggc
2301 cagccaaatc tacgccggca ttaaagtgaa gcagctgtgc aggctgctga
2351 gaggcgccaa agccctgaca gacatcgtga cactgacaga ggaggccgag
2401 ctggagctgg ccgagaacag ggagatcctg aaggaccccg tgcacggcgt
2451 gtactacgac cccagcaagg acctggtggc cgagattcag aagcagggcc
2501 aggaccagtg gacctaccaa atctaccagg agcctttcaa gaacctgaaa
2551 accgggaagt acgccaggaa gagaagcgcc cacaccaacg atgtgaggca
2601 gctggccgaa gtggtgcaga aagtggctat ggagagcatc gtgatctggg
2651 gcaagacccc caagttcaag ctgcccatcc agaaggagac ctgggaaacc
2701 tggtggatgg actactggca ggccacctgg attcctgagt gggagttcgt
2751 gaacaccccc cctctggtga agctgtggta tcagctggag aaggacccca
2801 tcctgggcgc cgagaccttc tacgtggacg gagccgccaa tagagagacc
2851 aagctgggca aggccggcta cgtgaccgac agaggcagac agaaagtggt
2901 gtctctgacc gagacaacca accagaaaac cgagctgcac gccatcctgc
2951 tggccctgca ggacagcggc agcgaagtga acatcgtgac cgactcccag
3001 tacgccctgg gcatcattca ggcccagccc gatagaagcg agagcgagct
3051 ggtgaaccag atcatcgaga agctgatcgg caaggacaaa atctacctga
3101 gctgggtgcc cgcccacaag ggcatcggcg gcaacgagca ggtggacaag
3151 ctggtgtcca gcggcatccg gaaagtgctg tttctggacg gcatcgacaa -continued

SEQUENCE

```
3201   ggcccaggag gaccacgaga gataccacag caactggcgg acaatggcca
3251   gcgacttcaa cctgcctccc atcgtggcca aggagatcgt ggccagctgc
3301   gataagtgtc agctgaaggg cgaggccatg cacggccagg tggactgcag
3351   ccctggcatc tggcagctgg cctgcaccca cctggagggc aaagtgattc
3401   tggtggccgt gcacgtggcc agcggctaca tcgaggccga agtgattccc
3451   gccgagaccg gccaggagac cgcctacttc ctgctgaagc tggccggcag
3501   atggcccgtg aaagtggtgc acaccgccaa cggcagcaac ttcacctctg
3551   ccgccgtgaa ggccgcctgt tggtgggcca atatccagca ggagttcggc
3601   atcccctaca accctcagag ccagggcgtg gtggccagca tgaacaagga
3651   gctgaagaag atcatcggcc aggtgaggga ccaggccgag cacctgaaaa
3701   cagccgtgca gatggccgtg ttcatccaca acttcaagcg gaagggcggc
3751   attggcggct acagcgccgg agagcggatc atcgacatca tcgccaccga
3801   tatccagacc aaggaactgc agaagcagat caccaagatt cagaacttca
3851   gagtgtacta ccgggacagc agggaccccca tctggaaggg ccctgccaag
3901   ctgctgtgga agggcgaagg cgccgtggtg atccaggaca acagcgacat
3951   caaagtggtg ccccggagga aggccaagat tctgcgggac tacggcaaac
4001   agatggccgg cgatgactgc gtggccggca ggcaggatga ggacagatct
4051   atgggcggca agtggtccaa gggcagcatt gtgggctggc ccgagatccg
4101   ggagagaatg agaagagccc ctgccgccgc tcctggagtg ggcgccgtgt
4151   ctcaggatct ggataagcac ggcgccatca ccagcagcaa catcaacaac
4201   cccagctgtg tgtggctgga ggcccaggaa gaggaggaag tgggcttccc
4251   tgtgagaccc caggtgcccc tgagacccat gacctacaag ggcgccttcg
4301   acctgagcca cttcctgaag gagaagggcg gcctggacgg cctgatctac
4351   agccggaagc ggcaggagat cctggatctg tgggtgtacc acacccaggg
4401   ctacttcccc gactggcaga attacacccc tggccctgga gtgcggtatc
4451   ccctgacctt cggctggtgc ttcaagctgg tgcctatgga gcccgacgaa
4501   gtggagaagg ccacagaggg cgagaacaac agcctgctgc accctatctg
4551   ccagcacggc atggacgatg aggagcggga agtgctgatc tggaagttcg
4601   acagcaggct ggccctgaag cacagagccc aggaactgca cccagagttc
4651   tacaaggact gctga
```

SEQ ID No 4:

```
   1   MAARASILSG GKLDAWEKIR LRPGGKKKYR LKHLVWASRE LDRFALNPSL
  51   LETTEGCQQI MNQLQPAVKT GTEEIKSLFN TVATLYCVHQ RIDVKDTKEA
 101   LDKIEEIQNK SKQKTQQAAA DTGDSSKVSQ NYPIIQNAQG QMIHQNLSPR
 151   TLNAWVKVIE EKAFSPEVIP MFSALSEGAT PQDLNVMLNI VGGHQAAMQM
 201   LKDTINEEAA EWDRLHPVQA GPIPPGQIRE PRGSDIAGTT STPQEQLQWM
 251   TGNPPIPVGN IYKRWIILGL NKIVRMYSPV SILDIKQGPK EPFRDYVDRF
 301   FKALRAEQAT QDVKGWMTET LLVQNANPDC KSILKALGSG ATLEEMMTAC
 351   QGVGGPGHKA RVLAEAMSQA QQTNIMMQRG NFRGQKRIKC FNCGKEGHLA
 401   RNCRAPRKKG CWKCGKEGHQ MKDCTERQAN FLGKIWPSSK GRPGNFPQSR
 451   PEPTAPPAEL FGMGEGIASL PKQEQKDREQ VPPLVSLKSL FGNDPLSQGS
 501   PISPIETVPV TLKPGMDGPK VKQWPLTEEK IKALTEICTE MEKEGKISKI
 551   GPENPYNTPI FAIKKKDSTK WRKLVDFREL NKRTQDFWEV QLGIPHPAGL
 601   KKKKSVTVLD VGDAYFSVPL DENFRKYTAF TIPSTNNETP GVRYQYNVLP
 651   QGWKGSPAIF QSSMTKILEP FRSKNPEIII YQYMAALYVG SDLEIGQHRT
 701   KIEELRAHLL SWGFTTPDKK HQKEPPFLWM GYELHPDKWT VQPIMLPDKE
 751   SWTVNDIQKL VGKLNWASQI YAGIKVKQLC RLLRGAKALT DIVTLTEEAE
 801   LELAENREIL KDPVHGVYYD PSKDLVAEIQ KQGQDQWTYQ IYQEPFKNLK
 851   TGKYARKRSA HTNDVRQLAE VVQKVAMESI VIWGKTPKFK LPIQKETWET
 901   WWMDYWQATW IPEWEFVNTP PLVKLWYQLE KDPILGAETF YVDGAANRET
 951   KLGKAGYVTD RGRQKVVSLT ETTNQKTELH AILLALQDSG SEVNIVTDSQ
1001   YALGIIQAQP DRSESELVNQ IIEKLIGKDK IYLSWVPAHK GIGGNEQVDK
1051   LVSSGIRKVL FLDGIDKAQE DHERYHSNWR TMASDFNLPP IVAKEIVASC
1101   DKCQLKGEAM HGQVDCSPGI WQLACTHLEG KVILVAVHVA SGYIEAEVIP
1151   AETGQETAYF LLKLAGRWPV KVVHTANGSN FTSAAVKAAC WWANIQQEFG
1201   IPYNPQSQGV VASMNKELKK IIGQVRDQAE HLKTAVQMAV FIHNFKRKGG
1251   IGGYSAGERI IDIIATDIQT KELQKQITKI QNFRVYYRDS RDPIWKGPAK
1301   LLWKGEGAVV IQDNSDIKVV PRRKAKILRD YGKQMAGDDC VAGRQDEDRS
1351   MGGKWSKGSI VGWPEIRERM RRAPAAAPGV GAVSQDLDKH GAITSSNINN
1401   PSCVWLEAQE EEVGFPVRP QVPLRPMTYK GAFDLSHFLK EKGGLDGLIY
1451   SRKRQEILDL WVYHTQGYFP DWQNYTPGPG VRYPLTFGWC FKLVPMEPDE
1501   VEKATEGENN SLLHPICQHG MDDEEREVLI WKFDSRLALK HRAQELHPEF
1551   YKDC
```

SEQ ID No 5:

```
   1   atgagggtga tggagatcca gcggaactgc cagcacctgc tgagatgggg
  51   catcatgatc ctgggcatga ttatcatctg cagcaccgcc gacaacctgt
 101   gggtgaccgt gtactacggc gtgcctgtgt ggagagatgc cgagaccacc
 151   ctgttctgcg ccagcgacgc caaggcctac agcaccgaga agcacaatgt
 201   gtgggccacc cacgcctgcg tgcctaccga tcccaaccct caggagatcc
 251   ccctggacaa cgtgaccgag gagttcaaca tgtggaagaa caacatggtg
 301   gaccagatgc acgaggacat catcagcctg tgggaccaga gcctgaagcc
 351   ctgcgtgcag ctgacccccc tgtgcgtgac cctgaactgc agcaacgcca
 401   gagtgaacgc caccttcaac tccaccgagg acagggaggg catgaagaac
 451   tgcagcttca acatgaccac cgagctgcgg gataagaagc agcaggtgta
```

-continued

| SEQUENCE |
| --- |

```
 501   cagcctgttc taccggctgg acatcgagaa gatcaacagc agcaacaaca
 551   acagcgagta ccggctggtg aactgcaata ccagcgccat cacccaggcc
 601   tgccctaagg tgaccttcga gcccatcccc atccactact gcgcccctgc
 651   cggcttcgcc atcctgaagt gcaacgacac cgagttcaat ggcaccggcc
 701   cctgcaagaa tgtgagcacc gtgcagtgca cccacggcat caagcccgtg
 751   gtgtccaccc agctgctgct gaacggcagc ctggccgaga gagaagtgcg
 801   gatcaggagc gagaacatcg ccaacaacgc caagaacatc atcgtgcagt
 851   tcgccagccc cgtgaagatc aactgcatcc ggcccaacaa caatacccgg
 901   aagagctaca gaatcggccc tggccagacc ttctacgcca ccgacattgt
 951   gggcgacatc agacaggccc actgcaacgt gtccaggacc gactggaaca
1001   acaccctgag actggtggcc aaccagctgc ggaagtactt cagcaacaag
1051   accatcatct tcaccaacag cagcggcgga gacctggaga tcaccaccca
1101   cagcttcaat tgtggcggcg agttcttcta ctgcaacacc tccggcctgt
1151   tcaatagcac ctggaccacc aacaacatgc aggagtccaa cgacaccagc
1201   aacggcacca tcaccctgcc ctgccggatc aagcagatca tccggatgtg
1251   gcagcgcgtg ggccaggcca tgtacgcccc tcccatcgag ggcgtgattc
1301   gctgcgagag caacatcacc ggcctgatcc tgaccagaga tggcggcaac
1351   aacaattccg ccaacgagac cttcagacct ggcggcggag atatccggga
1401   caactggcgg agcgagctgt acaagtacaa ggtggtgaag atcgagcccc
1451   tgggcgtggc ccccaccaga gccaagagaa gagtggtgga gcgggagaag
1501   agagccgtgg gcatcggcgc cgtgtttctg ggcttcctgg gagccgccgg
1551   atctacaatg ggagccgcca gcatcaccct gaccgtgcag gccagacagc
1601   tgctgagcgg catcgtgcag cagcagagca atctgctgag agccatcgag
1651   gcccagcagc agctgctgaa gctgacagtg tggggcatca agcagctgca
1701   ggccagggtg ctggccgtgg agagatacct gagggaccag cagctcctgg
1751   gcatctgggg ctgcagcggc aagctgatct gcaccaccaa cgtgccctgg
1801   aatagcagct ggagcaacaa gagctacgac gacatctggc agaacatgac
1851   ctggctgcag tgggacaagg agatcagcaa ctacaccgac atcatctaca
1901   gcctgatcga ggagagccag aaccagcagg agaagaacga gcaggatctg
1951   ctggccctgg acaagtgggc caacctgtgg aactggttcg acatcagcaa
2001   gtggctgtgg tacatcagat cttga
```

SEQ ID No 6:

```
  1    MRVMEIQRNC QHLLRWGIMI LGMIIICSTA DNLWVTVYYG VPVWRDAETT
 51    LFCASDAKAY STEKHNVWAT HACVPTDPNP QEIPLDNVTE EFNMWKNNMV
101    DQMHEDIISL WDQSLKPCVQ LTPLCVTLNC SNARVNATFN STEDREGMKN
151    CSFNMTTELR DKKQQVYSLF YRLDIEKINS SNNNSEYRLV NCNTSAITQA
201    CPKVTFEPIP IHYCAPAGFA ILKCNDTEFN GTGPCKNVST VQCTHGIKPV
251    VSTQLLLNGS LAEREVRIRS ENIANNAKNI IVQFASPVKI NCIRPNNNTR
301    KSYRIGPGQT FYATDIVGDI RQAHCNVSRT DWNNTLRLVA NQLRKYFSNK
351    TIIFTNSSGG DLEITTHSFN CGGEFFYCNT SGLFNSTWTT NNMQESNDTS
401    NGTITLPCRI KQIIRMWQRV GQAMYAPPIE GVIRCESNIT GLILTRDGGN
451    NNSANETFRP GGGDIRDNWR SELYKYKVVK IEPLGVAPTR AKRRVVEREK
501    RAVGIGAVFL GFLGAAGSTM GAASITLTVQ ARQLLSGIVQ QQSNLLRAIE
551    AQQQLLKLTV WGIKQLQARV LAVERYLRDQ QLLGIWGCSG KLICTTNVPW
601    NSSWSNKSYD DIWQNMTWLQ WDKEISNYTD IIYSLIEESQ NQQEKNEQDL
651    LALDKWANLW NWFDISKWLW YIRS
```

SEQ ID No 7:

```
atgaaagtga aggagaccag gaagaattat cagcacttgt ggagatgggg      50
caccatgctc cttgggatgt tgatgatctg tagtgctgca gaacaattgt     100
gggtcacagt ctattatggg gtacctgtgt ggaaagaagc aactaccact     150
ctattctgtg catcagatgc taaagcatat gatacagagg tacataatgt     200
ttgggccaca catgcctgtg tacccacaga ccccaaccca caagaagtag     250
tattgggaaa tgtgacagaa tattttaaca tgtggaaaaa taacatggta     300
gaccagatgc atgaggatat aatcagttta tgggatcaaa gcttgaagcc     350
atgtgtaaaa ttaaccccac tctgtgttac tttagattgc gatgatgtga     400
ataccactaa tagtactact accactagta atggttggac aggagaaata     450
aggaaaggag aaataaaaaa ctgctctttt aatatcacca caagcataag     500
agataaggtt caaaaagaat atgcactttt ttataacctt gatgtagtac     550
caatagatga tgataatgct actaccaaaa ataaaactac tagaaacttt     600
aggttgatac attgtaactc ctcagtcatg acacaggcct gtccaaaggt     650
atcatttgaa ccaattccca tacattattg tgccccggct ggttttgcga     700
ttctgaagtg taacaataag acgtttgatg gaaaaggact atgtacaaat     750
gtcagcacag tacaatgtac acatggaatt aggccagtag tgtcaactca     800
actgctgtta aatggcagtc tagcagaaga agaggtagta attagatctg     850
acaatttcat ggacaatact aaaaccataa tagtacagct gaatgaatct     900
gtagcaatta attgtacaag acccaacaac aatacaagaa aaggtataca     950
tataggacca gggagagcct tttatgcagc aagaaaaata ataggagata    1000
taagacaagc acattgtaac cttagtagag cacaatggaa taacacttta    1050
aaacagatag ttataaaatt aagagaacac tttgggaata aaacaataaa    1100
atttaatcaa tcctcaggag gggacccaga aattgtaagg catagtttta    1150
attgtggagg ggaatttttc tactgtgata caacacaact gtttaatagt    1200
acttggaatg gtactgaagg aaataacact gaaggaaata gcacaatcac    1250
actcccatgt agaataaaac aaattataaa catgtggcag gaagtaggaa    1300
aagcaatgta tgcccctccc atcggaggac aaattagatg ttcatcaaat    1350
attacagggc tgctattaac aagagatggt ggtaccgaag ggaatgggac    1400
```

-continued

| SEQUENCE |
|---|
| agagaatgag acagagatct tcagacctgg aggaggagat atgagggaca 1450 |
| attggagaag tgaattatat aaatataaag tagtaaaagt tgaaccacta 1500 |
| ggagtagcac ccaccagggc aaagagaaga gtggtgcaga gataa 1545 |
| |
| SEQ ID No 8: |
| MKVKETRKNY QHLWRWGTML LGMLMICSAA EQLWVTVYYG VPVWKEATTT 50 |
| LFCASDAKAY DTEVHNVWAT HACVPTDPNP QEVVLGNVTE YFNMWKNNMV 100 |
| DQMHEDIISL WDQSLKPCVK LTPLCVTLDC DDVNTTNSTT TTSNGWTGEI 150 |
| RKGEIKNCSF NITTSIRDKV QKEYALFYNL DVVPIDDDNA TTKNKTTRNF 200 |
| RLIHCNSSVM TQACPKVSFE PIPIHYCAPA GFAILKCNNK TFDGKGLCTN 250 |
| VSTVQCTHGI RPVVSTQLLL NGSLAEEEVV IRSDNFMDNT KTIIVQLNES 300 |
| VAINCTRPNN NTRKGIHIGP GRAFYAARKI IGDIRQAHCN LSRAQWNNTL 350 |
| KQIVIKLREH FGNKTIKFNQ SSGGDPEIVR HSFNCGGEFF YCDTTQLFNS 400 |
| TWNGTEGNNT EGNSTITLPC RIKQIINMWQ EVGKAMYAPP IGGQIRCSSN 450 |
| ITGLLLTRDG GTEGNGTENE TEIFRPGGGD MRDNWRSELY KYKVVKVEPL 500 |
| GVAPTRAKRR VVQR 514 |
| |
| SEQ ID No 9: |
| atgcatcaca cggccgcgtc cgataacttc cagctgtccc agggtgggca gggattcgcc 60 |
| attccgatcg ggcaggcgat ggcgatcgcg ggccagatcc gatcgggtgg ggggtcaccc 120 |
| accgttcata tcgggcctac cgccttcctc ggcttgggtg ttgtcgacaa caacggcaac 180 |
| ggcgcacgag tccaacgcgt ggtcgggagc gctccggcgg caagtctcgg catctccacc 240 |
| ggcgacgtga tcaccgcggt cgacggcgct ccgatcaact cggccaccgc gatggcggac 300 |
| gcgcttaacg ggcatcatcc cggtgacgtc atctcggtga cctggcaaac caagtcgggc 360 |
| ggcacgcgta cagggaacgt gacattggcc gagggacccc cggccgaatt catggtggat 420 |
| ttcggggcgt taccaccgga gatcaactcc gcgaggatgt acgccggccc gggttcggcc 480 |
| tcgctggtgg ccgcggctca gatgtgggac agcgtggcga gtgacctgtt ttcggccgcg 540 |
| tcggcgtttc agtcggtggt ctggggtctg acggtggggt cgtggatagg ttcgtcggcg 600 |
| ggtctgatgg tggcggcggc ctcgccgtat gtggcgtgga tgagcgtcac cgcggggcag 660 |
| gccgagctga ccgccgccca ggtccgggtt gctgcggcgg cctacgagac ggcgtatggg 720 |
| ctgacggtgc cccgccggt gatcgccgag aaccgtgctg aactgatgat tctgatagcg 780 |
| accaacctct tggggcaaaa caccccggcg atcgcggtca acgaggccga atacggcgag 840 |
| atgtgggccc aagacgccgc cgcgatgttt ggctacgccg cggcgacggc gacggcgacg 900 |
| gcgacgttgc tgccgttcga ggaggcgccg gagatgacca gcgcgggtgg gctcctcgag 960 |
| caggccgccg cggtcgagga ggcctccgac accgccgcgg cgaaccagtt gatgaacaat 1020 |
| gtgccccagg cgctgcaaca gctggcccag cccacgcagg gcaccacgcc ttcttccaag 1080 |
| ctgggtggcc tgtggaagac ggtctcgccg catcggtcgc cgatcagcaa catggtgtcg 1140 |
| atggccaaca accacatgtc gatgaccaac tcgggtgtgt cgatgaccaa caccttgagc 1200 |
| tcgatgttga agggctttgc tccggcggcg gccgcccagg ccgtgcaaac cgcggcgcaa 1260 |
| aacggggtcc gggcgatgag ctcgctgggc agctcgctgg gttcttcggg tctgggcggt 1320 |
| ggggtggccg ccaacttggg tcgggcggcc tcggtcggtt cgttgtcggt gccgcaggcc 1380 |
| tgggccgcgg ccaaccaggc agtcaccccg gcggcgcggg cgctgccgct gaccagcctg 1440 |
| accagcgccg cggaaagagg gcccgggcag atgctgggcg ggctgccggt ggggcagatg 1500 |
| ggcgccaggg ccggtggtgg gctcagtggt gtgctgcgtg ttccgccgcg accctatgtg 1560 |
| atgccgcatt ctccggcagc cggcgatatc gccccgccgg ccttgtcgca ggaccggttc 1620 |
| gccgacttcc ccgcgctgcc cctcgacccg tccgcgatgg tcgcccaagt ggggccacag 1680 |
| gtggtcaaca tcaacaccaa actgggctac aacaacgccg tgggcgccgg gaccggcatc 1740 |
| gtcatcgatc ccaacggtgt cgtgctgacc aacaaccacg tgatcgcggg cgccaccgac 1800 |
| atcaatgcgt tcagcgtcgg ctccggccaa acctacggcg tcgatgtggt cgggtatgac 1860 |
| cgcacccagg atgtcgcggt gctgcagctg cgcggtgccg gtggcctgcc gtcggcggcg 1920 |
| atcggtggcg gcgtcgcggt tggtgagccc gtcgtcgcga tgggcaacag cggtgggcag 1980 |
| ggcggaacgc cccgtgcggt gcctggcagg gtggtcgcgc tcggccaaac cgtgcaggcg 2040 |
| tcggattcgc tgaccggtgc cgaagagaca ttgaacgggt tgatccagtt cgatgccgcg 2100 |
| atccagcccg gtgatgcggg cgggcccgtc gtcaacggcc taggacaggt ggtcggtatg 2160 |
| aacacggccg cgtcctag 2178 |
| |
| SEQ ID No 10: |
| MHHTAASDNF QLSQGGQGFA IPIGQAMAIA GQIRSGGGSP TVHIGPTAFL GLGVVDNNGN 60 |
| GARVQRVVGS APAASLGIST GDVITAVDGA PINSATAMAD ALNGHHPGDV ISVTWQTKSG 120 |
| GTRTGNVTLA EGPPAEFMVD FGALPPEINS ARMYAGPGSA SLVAAAQMWD SVASDLFSAA 180 |
| SAFQSVVWGL TVGSWIGSSA GLMVAAASPY VAWMSVTAGQ AELTAAQVRV AAAAYETAYG 240 |
| LTVPPPVIAE NRAELMILIA TNLLGQNTPA IAVNEAEYGE MWAQDAAAMF GYAAATATAT 300 |
| ATLLPFEEAP EMTSAGGLLE QAAAVEEASD TAAANQLMNN VPQALQQLAQ PTQGTTPSSK 360 |
| LGGLWKTVSP HRSPISNMVS MANNHMSMTN SGVSMTNTLS SMLKGFAPAA AAQAVQTAAQ 420 |
| NGVRAMSSLG SSLGSSGLGG GVAANLGRAA SVGSLSVPQA WAAANQAVTP AARALPLTSL 480 |
| TSAAERGPGQ MLGGLPVGQM GARAGGGLSG VLRVPPRPYV MPHSPAAGDI APPALSQDRF 540 |
| ADFPALPLDP SAMVAQVGPQ VVNINTKLGY NNAVGAGTGI VIDPNGVVLT NNHVIAGATD 600 |
| INAFSVGSGQ TYGVDVVGYD RTQDVAVLQL RGAGGLPSAA IGGGVAVGEP VVAMGNSGGQ 660 |
| GGTPRAVPGR VVALGQTVQA SDSLTGAEET LNGLIQFDAA IQPGDAGGPV VNGLGQVVGM 720 |
| NTAAS 725 |
| |
| SEQ ID No 11: |
| atgatgagaa aacttgccat cctcagcgtc agctctttcc tgttcgtgga 50 |
| ggccctcttc caggagtatc agtgctacgg aagcagcagc aatacaaggg 100 |
| tcctgaacga gctcaactat gacaacgctg gaacgaacct gtataacgag 150 |
| ctggagatga actactatgg caagcaggag aactggtata gcctgaagaa 200 |
| gaacagccgg tccctgggcg agaacgacga cggcaacaac aacaacggcg 250 |

-continued

| SEQUENCE | |
|---|---|
| acaacggcag ggagggcaaa gatgaggaca agagggacgg gaacaacgag | 300 |
| gataacgaga agctgcggaa gcccaagcac aagaaactca agcagcccgc | 350 |
| cgacgggaac ccggacccca atgcaaatcc caacgtcgac ccaaacgcaa | 400 |
| accctaacgt ggaccccaac gccaatccca acgtcgatcc taatgccaat | 450 |
| ccaaatgcca accctaacgc aaatcctaat gcaaacccca acgccaatcc | 500 |
| taacgccaac ccaaatgcca acccaaacgc taaccccaac gctaacccaa | 550 |
| atgcaaatcc caatgctaac ccaaacgtgg accctaacgc taaccccaac | 600 |
| gcaaacccta acgccaatcc taacgcaaac cccaatgcaa acccaaacgc | 650 |
| aaatcccaac gctaacccta acgcaaaccc caacgccaac cctaatgcca | 700 |
| accccaatgc taaccccaac gccaatccaa acgcaaatcc aaacgccaac | 750 |
| ccaaatgcaa accccaacgc taatcccaac gccaacccaa acgccaatcc | 800 |
| taacaagaac aatcagggca acgggcaggg ccataacatg ccgaacgacc | 850 |
| ctaatcggaa tgtggacgag aacgccaacg ccaacagcgc cgtgaagaac | 900 |
| aacaacaacg aggagccctc cgacaagcac atcaaggaat acctgaacaa | 950 |
| gatccagaac agtctgagca ccgagtggtc cccctgctcc gtgacctgcg | 1000 |
| gcaacggcat ccaggtgagg atcaagcccg gctccgccaa caagcccaag | 1050 |
| gacgagctgg actacgccaa cgacatcgag aagaagatct gcaagatgga | 1100 |
| gaaatgcagc tctgtgttca acgtcgtgaa ctccgccatc ggcctgtga | 1149 |
| | |
| SEQ ID No 12: | |
| MMRKLAILSV SSFLFVEALF QEYQCYGSSS NTRVLNELNY DNAGTNLYNE | 50 |
| LEMNYYGKQE NWYSLKKNSR SLGENDDGNN NNGDNGREGK DEDKRDGNNE | 100 |
| DNEKLRKPKH KKLKQPADGN PDPNANPNVD PNANPNVDPN ANPNVDPNAN | 150 |
| PNANPNANPN ANPNANPNAN PNANPNANPN ANPNANPNAN PNVDPNANPN | 200 |
| ANPNANPNAN PNANPNANPN ANPNANPNAN PNANPNANPN ANPNANPNAN | 250 |
| PNANPNANPN ANPNANPNKN NQGNGQGHNM PNDPNRNVDE NANANSAVKN | 300 |
| NNNEEPSDKH IKEYLNKIQN SLSTEWSPCS VTCGNGIQVR IKPGSANKPK | 350 |
| DELDYANDIE KKICKMEKCS SVFNVVNSAI GL | 382 |
| | |
| SEQ ID No 13: | |
| atgatggctc ccgatcctaa tgcaaatcca aatgcaaacc caaacgcaaa | 50 |
| ccccaatgca aatcctaatg caaaccccaa tgcaaatcct aatgcaaatc | 100 |
| ctaatgccaa tccaaatgca aatccaaatg caaacccaaa cgcaaacccc | 150 |
| aatgcaaatc ctaatgccaa tccaaatgca aatccaaatg caaacccaaa | 200 |
| tgcaaaccca aatgcaaacc ccaatgcaaa tcctaataaa aacaatcaag | 250 |
| gtaatggaca aggtcacaat atgccaaatg acccaaaccg aaatgtagat | 300 |
| gaaaatgcta atgccaacag tgctgtaaaa aataataata acgaagaacc | 350 |
| aagtgataag cacataaaag aatatttaaa caaaatacaa aattctcttt | 400 |
| caactgaatg gtccccatgt agtgtaactt gtggaaatgg tattcaagtt | 450 |
| agaataaagc ctggctctgc taataaacct aaagacgaat tagattatgc | 500 |
| aaatgatatt gaaaaaaaaa tttgtaaaat ggaaaaatgt tccagtgtgt | 550 |
| ttaatgtcgt aaatagttca ataggattag ggcctgtgac gaacatggag | 600 |
| aacatcacat caggattcct aggacccctg ctcgtgttac aggcggggtt | 650 |
| tttcttgttg acaagaatcc tcacaatacc gcagagtcta gactcgtggt | 700 |
| ggacttctct caattttcta gggggatcac ccgtgtgtct tggccaaaat | 750 |
| tcgcagtccc caacctccaa tcactcacca acctcctgtc ctccaatttg | 800 |
| tcctggttat cgctggatgt gtctgcggcg ttttatcata ttcctcttca | 850 |
| tcctgctgct atgcctcatc ttcttattgg ttcttctgga ttatcaaggt | 900 |
| atgttgcccg tttgtcctct aattccagga tcaacaacaa ccaatacggg | 950 |
| accatgcaaa acctgcacga ctcctgctca aggcaactct atgtttccct | 1000 |
| catgttgctg tacaaaacct acggatggaa attgcacctg tattcccatc | 1050 |
| ccatcgtcct gggctttcgc aaaataccta tgggagtggg cctcagtccg | 1100 |
| tttctcttgg ctcagtttac tagtgccatt tgttcagtgg ttcgtagggc | 1150 |
| tttcccccac tgtttggctt tcagctatat ggatgatgtg gtattggggg | 1200 |
| ccaagtctgt acagcatcgt gagtcccttt ataccgctgt taccaatttt | 1250 |
| cttttgtctc tgggtataca tttaa | 1275 |
| | |
| SEQ ID No 14: | |
| MMAPDPNANP NANPNANPNA NPNANPNANP NANPNANPNA NPNANPNANP | 50 |
| NANPNANPNA NPNANPNANP NANPNANPNK NNQGNGQGHN MPNDPNRNVD | 100 |
| ENANANSAVK NNNNEEPSDK HIKEYLNKIQ NSLSTEWSPC SVTCGNGIQV | 150 |
| RIKPGSANKP KDELDYANDI EKKICKMEKC SSVFNVVNSS IGLGPVTNME | 200 |
| NITSGFLGPL LVLQAGFFLL TRILTIPQSL DSWWTSLNFL GGSPVCLGQN | 250 |
| SQSPTSNHSP TSCPPICPGY RWMCLRRFII FLFILLLCLI FLLVLLDYQG | 300 |
| MLPVCPLIPG STTTNTGPCK TCTTPAQGNS MFPSCCCTKP TDGNCTCIPI | 350 |
| PSSWAFAKYL WEWASVRFSW LSLLVPFVQW FVGLSPTVWL SAIWMMWYWG | 400 |
| PSLYSIVSPF IPLLPIFFCL WVYI | 424 |
| | |
| SEQ ID No 15: | |
| atggtcattg ttcagaacat acagggccaa atggtccacc aggcaattag | 50 |
| tccgcgaact cttaatgcat gggtgaaggt cgtggaggaa aaggcattct | 100 |
| ccccggaggt cattccgatg ttttctgcgc tatctgaggg cgcaacgccg | 150 |
| caagacctta ataccatgct taacacggta ggcgggcacc aagccgctat | 200 |
| gcaaatgcta aaagagacta taaacgaaga ggccgccgaa tgggatcgag | 250 |
| tgcacccggt gcacgccggc ccaattgcac caggccagat gcgcgagccg | 300 |
| cgcgggtctg atattgcagg aactacgtct acccttcagg agcagattgg | 350 |
| gtggatgact aacaatccac caatcccggt cggagagatc tataagaggt | 400 |

-continued

| SEQUENCE | |
|---|---|
| ggatcatact gggactaaac aagatagtcc gcatgtattc tccgacttct | 450 |
| atactggata tacgccaagg cccaaaggag ccgttcaggg actatgtcga | 500 |
| ccgattctat aagacccttc gcgcagagca ggcatcccag gaggtcaaaa | 550 |
| attggatgac agaaactctt ttggtgcaga atgcgaatcc ggattgtaaa | 600 |
| acaattttaa aggctctagg accggccgca acgctagaag agatgatgac | 650 |
| ggcttgtcag ggagtcggtg gaccggggca taaagcccgc gtcttacaca | 700 |
| tgggcccgat atctccgata gaaacagttt cggtcaagct taaaccaggg | 750 |
| atggatggtc caaaggtcaa gcagtggccg ctaacggaag agaagattaa | 800 |
| ggcgctcgta gagatttgta ctgaaatgga gaaggaaggc aagataagca | 850 |
| agatcgggcc agagaacccg tacaatacac cggtatttgc aataaagaaa | 900 |
| aaggattcaa caaaatggcg aaagcttgta gattttaggg aactaaacaa | 950 |
| gcgaacccaa gacttttggg aagtccaact agggatccca catccagccg | 1000 |
| gtctaaagaa gaagaaatcg gtcacagtcc tggatgtagg agacgcatat | 1050 |
| tttagtgtac cgcttgatga ggacttccga aagtatactg cgtttactat | 1100 |
| accgagcata aacaatgaaa cgccaggcat tcgctatcag tacaacgtgc | 1150 |
| tcccgcaggg ctggaagggg tctccggcga tatttcagag ctgtatgaca | 1200 |
| aaaatacttg aaccattccg aaagcagaat ccggatattg taatttacca | 1250 |
| atacatggac gatctctatg tgggctcgga tctagaaatt gggcagcatc | 1300 |
| gcactaagat tgaggaactg aggcaacatc tgcttcgatg gggcctcact | 1350 |
| actcccgaca agaagcacca gaaggagccg ccgttcctaa agatgggcta | 1400 |
| cgagcttcat ccggacaagt ggacagtaca gccgatagtg ctgcccgaaa | 1450 |
| aggattcttg gaccgtaaat gatattcaga aactagtcgg caagcttaac | 1500 |
| tgggcctctc agatttaccc aggcattaag gtccgacagc tttgcaagct | 1550 |
| actgagggga actaaggctc taacagaggt catcccatta acggaggaag | 1600 |
| cagagcttga gctggcagag aatcgcgaaa ttcttaagga gccggtgcac | 1650 |
| ggggtatact acgacccctc caaggacctt atagccgaga tccagaagca | 1700 |
| ggggcagggc caatggacgt accagatata tcaagaaccg tttaagaatc | 1750 |
| tgaagactgg gaagtacgcg cgcatgcgag ggctcatac taatgatgta | 1800 |
| aagcaactta cggaagcagt acaaaagatt actactgagt ctattgtgat | 1850 |
| atggggcaag accccaaagt tcaagctgcc catacagaag gaaacatggg | 1900 |
| aaacatggtg gactgaatat tggcaagcta cctggattcc agaatgggaa | 1950 |
| tttgtcaaca cgccgccact tgttaagctt tggtaccagc ttgaaaagga | 2000 |
| gccgatagta ggggcagaga ccttctatgt cgatggcgcc gcgaatcgcg | 2050 |
| aaacgaagct aggcaaggcg ggatacgtga ctaatagggg ccgccaaaag | 2100 |
| gtcgtaaccc ttacggatac caccaatcag aagactgaac tacaagcgat | 2150 |
| ttaccttgca cttcaggata gtggcctaga ggtcaacata gtcacggact | 2200 |
| ctcaatatgc gcttggcatt attcaagcgc agccagatca aagcgaaagc | 2250 |
| gagcttgtaa accaaataat agaacagctt ataaagaaag agaaggtata | 2300 |
| tctggcctgg gtccccgctc acaagggaat tggcggcaat gagcaagtgg | 2350 |
| acaagctagt cagcgctggg attcgcaagg ttcttgcgat ggggggtaag | 2400 |
| tggtctaagt ctagcgtagt cggctggccg acagtccgcg agcgcatgcg | 2450 |
| acgcgccgaa ccagccgcag atggcgtggg ggcagcgtct agggatctgg | 2500 |
| agaagcacgg ggctataact tccagtaaca cggcggcgac gaacgccgca | 2550 |
| tgcgcatggt tagaagccca agaagaggaa gaagtagggt ttccggtaac | 2600 |
| tccccaggtg ccgttaaggc cgatgaccta taaggcagcg gtggatcttt | 2650 |
| ctcacttcct taaggagaaa ggggggctgg agggcttaat tcacagccag | 2700 |
| aggcgacagg atattcttga tctgtggatt taccataccc aggggtactt | 2750 |
| tccggactgg cagaattaca ccccggggcc aggcgtgcgc tatcccctga | 2800 |
| ctttcgggtg gtgctacaaa ctagtcccag tggaacccga caaggtcgaa | 2850 |
| gaggctaata agggcgagaa cacttctctt cttcacccgg taagcctgca | 2900 |
| cgggatggat gacccagaac gagaggttct agaatggagg ttcgactctc | 2950 |
| gacttgcgtt ccatcacgta gcacgcgagc tgcatccaga atatttcaag | 3000 |
| aactgccgcc caatgggcgc cagggccagt gtacttagtg gcggagaact | 3050 |
| agatcgatgg gaaaagatac gcctacgccc ggggggcaag aagaagtaca | 3100 |
| agcttaagca cattgtgtgg gcctctcgcg aacttgagcg attcgcagtg | 3150 |
| aatccaggcc tgcttgagac gagtgaaggc tgtaggcaaa ttctggggca | 3200 |
| gctacagccg agcctacaga ctggcagcga ggagcttcgt agtctttata | 3250 |
| ataccgtcgc gactctctac tgcgttcatc aacgaattga aataaaggat | 3300 |
| actaaagagg cccttgataa aattgaggag gaacagaata agtcgaaaaa | 3350 |
| gaaggcccag caggccgccg ccgacaccgg gcacagcaac caggtgtccc | 3400 |
| aaaactacta a | 3411 |
| | |
| SEQ ID No 16: | |
| MVIVQNIQGQ MVHQAISPRT LNAWVKVVEE KAFSPEVIPM FSALSEGATP | 50 |
| QDLNTMLNTV GGHQAAMQML KETINEEAAE WDRVHPVHAG PIAPGQMREP | 100 |
| RGSDIAGTTS TLQEQIGWMT NNPPIPVGEI YKRWIILGLN KIVRMYSPTS | 150 |
| ILDIRQGPKE PFRDYVDRFY KTLRAEQASQ EVKNWMTETL LVQNANPDCK | 200 |
| TILKALGPAA TLEEMMTACQ GVGGPGHKAR VLHMGPISPI ETVSVKLKPG | 250 |
| MDGPKVKQWP LTEEKIKALV EICTEMEKEG KISKIGPENP YNTPVFAIKK | 300 |
| KDSTKWRKLV DFRELNKRTQ DFWEVQLGIP HPAGLKKKKS VTVLDVGDAY | 350 |
| FSVPLDEDFR KYTAFTIPSI NNETPGIRYQ YNVLPQGWKG SPAIFQSCMT | 400 |
| KILEPFRKQN PDIVIYQYMD DLYVGSDLEI GQHRTKIEEL RQHLLRWGLT | 450 |
| TPDKKHQKEP PFLKMGYELH PDKWTVQPIV LPEKDSWTVN DIQKLVGKLN | 500 |
| WASQIYPGIK VRQLCKLLRG TKALTEVIPL TEEAELELAE NREILKEPVH | 550 |
| GVYYDPSKDL IAEIQKQGQG QWTYQIYQEP FKNLKTGKYA RMRGAHTNDV | 600 |
| KQLTEAVQKI TTESIVIWGK TPKFKLPIQK ETWETWWTEY WQATWIPEWE | 650 |
| FVNTPPLVKL WYQLEKEPIV GAETFYVDGA ANRETKLGKA GYVTNRGRQK | 700 |

-continued

| SEQUENCE | |
|---|---|
| VVTLTDTTNQ KTELQAIYLA LQDSGLEVNI VTDSQYALGI IQAQPDQSES | 750 |
| ELVNQIIEQL IKKEKVYLAW VPAHKGIGGN EQVDKLVSAG IRKVLAMGGK | 800 |
| WSKSSVVGWP TVRERMRRAE PAADGVGAAS RDLEKHGAIT SSNTAATNAA | 850 |
| CAWLEAQEEE EVGFPVTPQV PLRPMTYKAA VDLSHFLKEK GGLEGLIHSQ | 900 |
| RRQDILDLWI YHTQGYFPDW QNYTPGPGVR YPLTFGWCYK LVPVEPDKVE | 950 |
| EANKGENTSL LHPVSLHGMD DPEREVLEWR FDSRLAFHHV ARELHPEYFK | 1000 |
| NCRPMGARAS VLSGGELDRW EKIRLRPGGK KKYKLKHIVW ASRELERFAV | 1050 |
| NPGLLETSEG CRQILGQLQP SLQTGSEELR SLYNTVATLY CVHQRIEIKD | 1100 |
| TKEALDKIEE EQNKSKKKAQ QAAADTGHSN QVSQNY | 1136 |

All references referred to in this application, including patent and patent applications, are incorporated herein by reference to the fullest extent possible.

Throughout the specification and the claims which follow, unless the context requires otherwise, the word ‘comprise’, and variations such as ‘comprises’ and ‘comprising’, will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. A vaccine composition comprising (i) one or more first immunogenic polypeptides derived from *Mycobacterium tuberculosis*; (ii) one or more adenoviral vectors comprising one or more heterologous polynucleotides encoding one or more second immunogenic polypeptides derived from said *Mycobacterium tuberculosis*; and (iii) an adjuvant;

wherein all of said immunogenic polypeptides have a sequence identity greater than 80% to SEQ ID NO: 10.

2. The vaccine composition according to claim 1 wherein one or more of said immunogenic polypeptides have a sequence identity greater than 90% to SEQ ID NO: 10.

3. The vaccine composition according to claim 2 wherein one or more of said immunogenic polypeptides comprises residues 4-725 of SEQ ID NO: 10.

4. The vaccine composition according to claim 1 wherein one or more of any of the said immunogenic polypeptides comprise TbH9 (Mtb39a), wherein TbH9 (Mtb39a) is residues 139-528 of SEQ ID NO: 10.

5. The vaccine composition according to claim 1 wherein one or more of the adenoviral vectors is a human adenovirus.

6. The vaccine composition according to claim 1 wherein one or more of the adenoviral vectors is replication defective.

7. A kit comprising (i) one or more first immunogenic polypeptides derived from *Mycobacterium tuberculosis*; (ii) one or more adenoviral vectors comprising one or more heterologous polynucleotides encoding one or more second immunogenic polypeptides derived from said *Mycobacterium tuberculosis*; and (iii) an adjuvant;

wherein all of said immunogenic polypeptides have a sequence identity greater than 80% to SEQ ID NO: 10.

* * * * *

SEQUENCE LISTING

<160> NUMBER OF SEQ ID NOS: 16

<210> SEQ ID NO 1
<211> LENGTH: 3204
<212> TYPE: DNA
<213> ORGANISM: Artificial Sequence
<220> FEATURE:
<223> OTHER INFORMATION: HIV

<400> SEQUENCE: 1
atgggtgccc gagcttcggt actgtctggt ggagagctgg acagatggga gaaaattagg 60
ctgcgcccgg gaggcaaaaa gaaatacaag ctcaagcata tcgtgtgggc ctcgagggag 120
cttgaacggt ttgccgtgaa cccaggcctg ctggaaacat ctgagggatg tcgccagatc 180
ctggggcaat tgcagccatc cctccagacc gggagtgaag agctgaggtc cttgtataac 240
acagtggcta ccctctactg cgtacaccag aggatcgaga ttaaggatac caaggaggcc 300
ttggacaaaa ttgaggagga gcaaaacaag agcaagaaga aggcccagca ggcagctgct 360
gacactgggc atagcaacca ggtatcacag aactatccta ttgtccaaaa cattcagggc 420
cagatggttc atcaggccat cagcccccgg acgctcaatg cctgggtgaa ggttgtcgaa 480
gagaaggcct tttctcctga ggttatcccc atgttctccg ctttgagtga gggggccact 540
cctcaggacc tcaatacaat gcttaatacc gtgggcggcc atcaggccgc catgcaaatg 600
ttgaaggaga ctatcaacga ggaggcagcc gagtgggaca gagtgcatcc cgtccacgct 660
ggcccaatcg cgcccggaca gatgcgggag cctcgcggct ctgacattgc cggcaccacc 720
tctacactgc aagagcaaat cggatggatg accaacaatc ctcccatccc agttggagaa 780
atctataaac ggtggatcat cctgggcctg aacaagatcg tgcgcatgta ctctccgaca 840
tccatccttg acattagaca gggacccaaa gagcctttta gggattacgt cgaccggttt 900
tataagaccc tgcgagcaga gcaggcctct caggaggtca aaaactggat gacggagaca 960
ctcctggtac agaacgctaa ccccgactgc aaaacaatct tgaaggcact aggcccggct 1020
gccaccctgg aagagatgat gaccgcctgt cagggagtag gcggacccgg acacaaagcc 1080
agagtgttga tgggccccat cagtcccatc gagaccgtgc cggtgaagct gaaacccggg 1140
atggacggcc ccaaggtcaa gcagtggcca ctcaccgagg agaagatcaa ggccctggtg 1200

-continued

```
gagatctgca ccgagatgga gaaagagggc aagatcagca agatcgggcc ggagaaccca   1260
tacaacaccc ccgtgtttgc catcaagaag aaggacagca ccaagtggcg caagctggtg   1320
gatttccggg agctgaataa gcggacccag gatttctggg aggtccagct gggcatcccc   1380
catccggccg gcctgaagaa gaagaagagc gtgaccgtgc tggacgtggg cgacgcttac   1440
ttcagcgtcc ctctggacga ggactttaga aagtacaccg cctttaccat cccatctatc   1500
aacaacgaga cccctggcat cagatatcag tacaacgtcc tcccccaggg ctggaagggc   1560
tctcccgcca ttttccagag ctccatgacc aagatcctgg agccgtttcg gaagcagaac   1620
cccgatatcg tcatctacca gtacatggac gacctgtacg tgggctctga cctggaaatc   1680
gggcagcatc gcacgaagat tgaggagctg aggcagcatc tgctgagatg gggcctgacc   1740
actccggaca agaagcatca gaaggagccg ccattcctga agatgggcta cgagctccat   1800
cccgacaagt ggaccgtgca gcctatcgtc ctccccgaga aggacagctg gaccgtgaac   1860
gacatccaga agctggtggg caagctcaac tgggctagcc agatctatcc cgggatcaag   1920
gtgcgccagc tctgcaagct gctgcgcggc accaaggccc tgaccgaggt gattcccctc   1980
acggaggaag ccgagctcga gctggctgag aaccgggaga tcctgaagga gcccgtgcac   2040
ggcgtgtact atgacccctc caaggacctg atcgccgaaa tccagaagca gggccagggg   2100
cagtggacat accagattta ccaggagcct ttcaagaacc tcaagaccgg caagtacgcc   2160
cgcatgaggg gcgcccacac caacgatgtc aagcagctga ccgaggccgt ccagaagatc   2220
acgaccgagt ccatcgtgat ctgggggaag acacccaagt tcaagctgcc tatccagaag   2280
gagacctggg agacgtggtg gaccgaatat tggcaggcca cctggattcc cgagtgggag   2340
ttcgtgaata cacctcctct ggtgaagctg tggtaccagc tcgagaagga gcccatcgtg   2400
ggcgcggaga cattctacgt ggacggcgcg gccaaccgcg aaacaaagct cgggaaggcc   2460
gggtacgtca ccaaccgggg ccgccagaag gtcgtcaccc tgaccgacac caccaaccag   2520
aagacggagc tgcaggccat ctatctcgct ctccaggact ccggcctgga ggtgaacatc   2580
gtgacggaca gccagtacgc gctgggcatt attcaggccc agccggacca gtccgagagc   2640
gaactggtga accagattat cgagcagctg atcaagaaag agaaggtcta cctcgcctgg   2700
gtcccggccc ataagggcat tggcggcaac gagcaggtcg acaagctggt gagtgcgggg   2760
attagaaagg tgctgatggt gggttttcca gtcacacctc aggtaccttt aagaccaatg   2820
acttacaagg cagctgtaga tcttagccac tttttaaaag aaaagggggg actggaaggg   2880
ctaattcact cccaaagaag acaagatatc cttgatctgt ggatctacca cacacaaggc   2940
tacttccctg attggcagaa ctacacacca gggccagggg tcagatatcc actgaccttt   3000
ggatggtgct acaagctagt accagttgag ccagataagg tagaagaggc caataaagga   3060
gagaacacca gcttgttaca ccctgtgagc ctgcatggga tggatgaccc ggagagagaa   3120
gtgttagagt ggaggtttga cagccgccta gcatttcatc acgtggcccg agagctgcat   3180
ccggagtact tcaagaactg ctga                                          3204
```

<210> SEQ ID NO 2
<211> LENGTH: 1067
<212> TYPE: PRT
<213> ORGANISM: Artificial Sequence
<220> FEATURE:
<223> OTHER INFORMATION: HIV

<400> SEQUENCE: 2

-continued

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Met Gly Pro Ile Ser
        355                 360                 365

Pro Ile Glu Thr Val Pro Val Lys Leu Lys Pro Gly Met Asp Gly Pro
    370                 375                 380

Lys Val Lys Gln Trp Pro Leu Thr Glu Glu Lys Ile Lys Ala Leu Val
385                 390                 395                 400

Glu Ile Cys Thr Glu Met Glu Lys Glu Gly Lys Ile Ser Lys Ile Gly
                405                 410                 415

Pro Glu Asn Pro Tyr Asn Thr Pro Val Phe Ala Ile Lys Lys Lys Asp
```

-continued

```
            420                 425                 430

Ser Thr Lys Trp Arg Lys Leu Val Asp Phe Arg Glu Leu Asn Lys Arg
        435                 440                 445

Thr Gln Asp Phe Trp Glu Val Gln Leu Gly Ile Pro His Pro Ala Gly
    450                 455                 460

Leu Lys Lys Lys Lys Ser Val Thr Val Leu Asp Val Gly Asp Ala Tyr
465                 470                 475                 480

Phe Ser Val Pro Leu Asp Glu Asp Phe Arg Lys Tyr Thr Ala Phe Thr
                485                 490                 495

Ile Pro Ser Ile Asn Asn Glu Thr Pro Gly Ile Arg Tyr Gln Tyr Asn
            500                 505                 510

Val Leu Pro Gln Gly Trp Lys Gly Ser Pro Ala Ile Phe Gln Ser Ser
        515                 520                 525

Met Thr Lys Ile Leu Glu Pro Phe Arg Lys Gln Asn Pro Asp Ile Val
    530                 535                 540

Ile Tyr Gln Tyr Met Asp Asp Leu Tyr Val Gly Ser Asp Leu Glu Ile
545                 550                 555                 560

Gly Gln His Arg Thr Lys Ile Glu Glu Leu Arg Gln His Leu Leu Arg
                565                 570                 575

Trp Gly Leu Thr Thr Pro Asp Lys Lys His Gln Lys Glu Pro Pro Phe
            580                 585                 590

Leu Lys Met Gly Tyr Glu Leu His Pro Asp Lys Trp Thr Val Gln Pro
        595                 600                 605

Ile Val Leu Pro Glu Lys Asp Ser Trp Thr Val Asn Asp Ile Gln Lys
    610                 615                 620

Leu Val Gly Lys Leu Asn Trp Ala Ser Gln Ile Tyr Pro Gly Ile Lys
625                 630                 635                 640

Val Arg Gln Leu Cys Lys Leu Leu Arg Gly Thr Lys Ala Leu Thr Glu
                645                 650                 655

Val Ile Pro Leu Thr Glu Glu Ala Glu Leu Glu Leu Ala Glu Asn Arg
            660                 665                 670

Glu Ile Leu Lys Glu Pro Val His Gly Val Tyr Tyr Asp Pro Ser Lys
        675                 680                 685

Asp Leu Ile Ala Glu Ile Gln Lys Gln Gly Gln Gly Gln Trp Thr Tyr
    690                 695                 700

Gln Ile Tyr Gln Glu Pro Phe Lys Asn Leu Lys Thr Gly Lys Tyr Ala
705                 710                 715                 720

Arg Met Arg Gly Ala His Thr Asn Asp Val Lys Gln Leu Thr Glu Ala
                725                 730                 735

Val Gln Lys Ile Thr Thr Glu Ser Ile Val Ile Trp Gly Lys Thr Pro
            740                 745                 750

Lys Phe Lys Leu Pro Ile Gln Lys Glu Thr Trp Glu Thr Trp Trp Thr
        755                 760                 765

Glu Tyr Trp Gln Ala Thr Trp Ile Pro Glu Trp Glu Phe Val Asn Thr
    770                 775                 780

Pro Pro Leu Val Lys Leu Trp Tyr Gln Leu Glu Lys Glu Pro Ile Val
785                 790                 795                 800

Gly Ala Glu Thr Phe Tyr Val Asp Gly Ala Ala Asn Arg Glu Thr Lys
                805                 810                 815

Leu Gly Lys Ala Gly Tyr Val Thr Asn Arg Gly Arg Gln Lys Val Val
            820                 825                 830

Thr Leu Thr Asp Thr Thr Asn Gln Lys Thr Glu Leu Gln Ala Ile Tyr
        835                 840                 845
```

-continued

```
Leu Ala Leu Gln Asp Ser Gly Leu Glu Val Asn Ile Val Thr Asp Ser
    850                 855                 860

Gln Tyr Ala Leu Gly Ile Ile Gln Ala Gln Pro Asp Gln Ser Glu Ser
865                 870                 875                 880

Glu Leu Val Asn Gln Ile Ile Glu Gln Leu Ile Lys Lys Glu Lys Val
                885                 890                 895

Tyr Leu Ala Trp Val Pro Ala His Lys Gly Ile Gly Gly Asn Glu Gln
            900                 905                 910

Val Asp Lys Leu Val Ser Ala Gly Ile Arg Lys Val Leu Met Val Gly
        915                 920                 925

Phe Pro Val Thr Pro Gln Val Pro Leu Arg Pro Met Thr Tyr Lys Ala
    930                 935                 940

Ala Val Asp Leu Ser His Phe Leu Lys Glu Lys Gly Gly Leu Glu Gly
945                 950                 955                 960

Leu Ile His Ser Gln Arg Arg Gln Asp Ile Leu Asp Leu Trp Ile Tyr
                965                 970                 975

His Thr Gln Gly Tyr Phe Pro Asp Trp Gln Asn Tyr Thr Pro Gly Pro
            980                 985                 990

Gly Val Arg Tyr Pro Leu Thr Phe Gly Trp Cys Tyr Lys Leu Val Pro
        995                 1000                1005

Val Glu Pro Asp Lys Val Glu Glu Ala Asn Lys Gly Glu Asn Thr Ser
    1010                1015                1020

Leu Leu His Pro Val Ser Leu His Gly Met Asp Asp Pro Glu Arg Glu
1025                1030                1035                1040

Val Leu Glu Trp Arg Phe Asp Ser Arg Leu Ala Phe His His Val Ala
                1045                1050                1055

Arg Glu Leu His Pro Glu Tyr Phe Lys Asn Cys
            1060                1065


<210> SEQ ID NO 3
<211> LENGTH: 4665
<212> TYPE: DNA
<213> ORGANISM: Artificial Sequence
<220> FEATURE:
<223> OTHER INFORMATION: HIV

<400> SEQUENCE: 3

atggccgcca gagccagcat cctgagcggg ggcaagctgg acgcctggga gaagatcaga      60

ctgaggcctg gcggcaagaa gaagtaccgg ctgaagcacc tggtgtgggc cagcagagag     120

ctggatcgct tcgccctgaa tcctagcctg ctggagacca ccgagggctg ccagcagatc     180

atgaaccagc tgcagcccgc cgtgaaaacc ggcaccgagg agatcaagag cctgttcaac     240

accgtggcca ccctgtactg cgtgcaccag cggatcgacg tgaaggatac caaggaggcc     300

ctggacaaga tcgaggagat ccagaacaag agcaagcaga aaacccagca ggccgctgcc     360

gacaccggcg acagcagcaa agtgagccag aactacccca tcatccagaa tgcccagggc     420

cagatgatcc accagaacct gagccccaga accctgaatg cctgggtgaa agtgatcgag     480

gaaaaggcct tcagccccga agtgatccct atgttcagcg ccctgagcga gggcgccacc     540

ccccaggacc tgaacgtgat gctgaacatt gtgggcggac accaggccgc catgcagatg     600

ctgaaggaca ccatcaatga ggaggccgcc gagtgggaca gactgcaccc cgtgcaggcc     660

ggacccatcc cccctggcca gatcagagag cccagaggca gcgacatcgc cggcaccacc     720

tccacccctc aagaacagct gcagtggatg accggcaacc ctcccatccc tgtgggcaac     780
```

-continued

```
atctacaagc ggtggatcat cctgggcctg aacaagattg tgcggatgta cagccccgtg    840
tccatcctgg atatcaagca gggccccaag gagcccttca gagactacgt ggaccggttc    900
ttcaaggccc tgagagccga gcaggccacc caggacgtga agggctggat gaccgagacc    960
ctgctggtgc agaacgccaa ccccgactgc aagagcatcc tgaaggccct gggcagcggc   1020
gccacactgg aggagatgat gaccgcctgc cagggagtgg gcggacccgg ccacaaggcc   1080
agagtgctgg ccgaggccat gagccaggcc cagcagacca acatcatgat gcagcggggc   1140
aacttcagag gccagaagcg gatcaagtgc ttcaactgcg gcaaggaggg ccacctggcc   1200
agaaactgca gagcccccag gaagaagggc tgctggaagt gtggcaagga agggcaccag   1260
atgaaggact gcaccgagag gcaggccaat ttcctgggca agatttggcc tagcagcaag   1320
ggcagacccg gcaatttccc ccagagcaga cccgagccca ccgcccctcc cgccgagctg   1380
ttcggcatgg gcgagggcat cgccagcctg cccaagcagg agcagaagga cagagagcag   1440
gtgccccccc tggtgtccct gaagtccctg ttcggcaacg atcctctgag ccagggatcc   1500
cccatcagcc ccatcgagac cgtgcccgtg accctgaagc ccggcatgga tggccccaaa   1560
gtgaaacagt ggcccctgac cgaggagaag attaaggccc tgaccgaaat ctgtaccgag   1620
atggagaagg agggcaagat cagcaagatc ggcccccgaga accccctacaa cacccccatc   1680
ttcgccatca agaagaagga cagcaccaag tggcggaaac tggtggactt ccgggagctg   1740
aacaagagga cccaggactt ctgggaagtg cagctgggca tcccccaccc tgccggcctg   1800
aagaagaaga agtccgtgac agtgctggat gtgggcgacg cctacttcag cgtgcccctg   1860
gacgagaact tcaggaagta caccgccttc accatcccca gcaccaacaa cgagaccccc   1920
ggagtgagat accagtacaa cgtgctgcct cagggctgga agggcagccc cgccatcttc   1980
cagagcagca tgaccaagat cctggagccc ttccggagca agaaccccga gatcatcatc   2040
taccagtaca tggccgccct gtatgtgggc agcgatctgg agatcggcca gcacaggacc   2100
aagatcgaag agctgagggc ccacctgctg agctggggct tcaccacccc cgataagaag   2160
caccagaagg agcccccttt cctgtggatg ggctacgagc tgcaccccga taagtggacc   2220
gtgcagccca tcatgctgcc cgataaggag agctggaccg tgaacgacat ccagaaactg   2280
gtgggcaagc tgaattgggc cagccaaatc tacgccggca ttaaagtgaa gcagctgtgc   2340
aggctgctga gaggcgccaa agccctgaca gacatcgtga cactgacaga ggaggccgag   2400
ctggagctgg ccgagaacag ggagatcctg aaggaccccg tgcacggcgt gtactacgac   2460
cccagcaagg acctggtggc cgagattcag aagcagggcc aggaccagtg gacctaccaa   2520
atctaccagg agcctttcaa gaacctgaaa accgggaagt acgccaggaa gagaagcgcc   2580
cacaccaacg atgtgaggca gctggccgaa gtggtgcaga aagtggctat ggagagcatc   2640
gtgatctggg gcaagacccc caagttcaag ctgcccatcc agaaggagac ctgggaaacc   2700
tggtggatgg actactggca ggccacctgg attcctgagt gggagttcgt gaacaccccc   2760
cctctggtga agctgtggta tcagctggag aaggacccca tcctgggcgc cgagaccttc   2820
tacgtggacg gagccgccaa tagagagacc aagctgggca aggccggcta cgtgaccgac   2880
agaggcagac agaaagtggt gtctctgacc gagacaacca accagaaaac cgagctgcac   2940
gccatcctgc tggccctgca ggacagcggc agcgaagtga acatcgtgac cgactcccag   3000
tacgccctgg gcatcattca ggcccagccc gatagaagcg agagcgagct ggtgaaccag   3060
atcatcgaga agctgatcgg caaggacaaa atctacctga gctgggtgcc cgcccacaag   3120
ggcatcggcg gcaacgagca ggtggacaag ctggtgtcca gcggcatccg gaaagtgctg   3180
```

```
tttctggacg gcatcgacaa ggcccaggag gaccacgaga gataccacag caactggcgg   3240

acaatggcca gcgacttcaa cctgcctccc atcgtggcca aggagatcgt ggccagctgc   3300

gataagtgtc agctgaaggg cgaggccatg cacggccagg tggactgcag ccctggcatc   3360

tggcagctgg cctgcaccca cctggagggc aaagtgattc tggtggccgt gcacgtggcc   3420

agcggctaca tcgaggccga agtgattccc gccgagaccg gccaggagac cgcctacttc   3480

ctgctgaagc tggccggcag atggcccgtg aaagtggtgc acaccgccaa cggcagcaac   3540

ttcacctctg ccgccgtgaa ggccgcctgt tggtgggcca atatccagca ggagttcggc   3600

atcccctaca accctcagag ccagggcgtg gtggccagca tgaacaagga gctgaagaag   3660

atcatcggcc aggtgaggga ccaggccgag cacctgaaaa cagccgtgca gatggccgtg   3720

ttcatccaca acttcaagcg gaagggcggc attggcggct acagcgccgg agagcggatc   3780

atcgacatca tcgccaccga tatccagacc aaggaactgc agaagcagat caccaagatt   3840

cagaacttca gagtgtacta ccgggacagc agggaccccca tctggaaggg ccctgccaag   3900

ctgctgtgga agggcgaagg cgccgtggtg atccaggaca acagcgacat caaagtggtg   3960

ccccggagga aggccaagat tctgcgggac tacggcaaac agatggccgg cgatgactgc   4020

gtggccggca ggcaggatga ggacagatct atgggcggca agtggtccaa gggcagcatt   4080

gtgggctggc ccgagatccg ggagagaatg agaagagccc ctgccgccgc tcctggagtg   4140

ggcgccgtgt ctcaggatct ggataagcac ggcgccatca ccagcagcaa catcaacaac   4200

cccagctgtg tgtggctgga ggcccaggaa gaggaggaag tgggcttccc tgtgagaccc   4260

caggtgcccc tgagacccat gacctacaag ggcgccttcg acctgagcca cttcctgaag   4320

gagaagggcg gcctggacgg cctgatctac agccggaagc ggcaggagat cctggatctg   4380

tgggtgtacc acacccaggg ctacttcccc gactggcaga attacacccc tggccctgga   4440

gtgcggtatc ccctgacctt cggctggtgc ttcaagctgg tgcctatgga gcccgacgaa   4500

gtggagaagg ccacagaggg cgagaacaac agcctgctgc accctatctg ccagcacggc   4560

atggacgatg aggagcggga agtgctgatc tggaagttcg acagcaggct ggccctgaag   4620

cacagagccc aggaactgca cccagagttc tacaaggact gctga                   4665
```

```
<210> SEQ ID NO 4
<211> LENGTH: 1554
<212> TYPE: PRT
<213> ORGANISM: Artificial Sequence
<220> FEATURE:
<223> OTHER INFORMATION: HIV

<400> SEQUENCE: 4

Met Ala Ala Arg Ala Ser Ile Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Asp Arg Phe Ala Leu Asn Pro
        35                  40                  45

Ser Leu Leu Glu Thr Thr Glu Gly Cys Gln Gln Ile Met Asn Gln Leu
    50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
                85                  90                  95
```

-continued

```
Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
    210                 215                 220

Pro Gly Gln Ile Arg Glu Pro Arg Gly Ser Asp Ile Ala Gly Thr Thr
225                 230                 235                 240

Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
        275                 280                 285

Pro Lys Glu Pro Phe Arg Asp Tyr Val Asp Arg Phe Phe Lys Ala Leu
    290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Gln Gln Thr Asn Ile Met Met Gln Arg Gly Asn Phe Arg Gly
    370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Pro Ala Glu Leu Phe Gly Met Gly
    450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln Gly Ser Pro Ile Ser Pro Ile Glu Thr Val Pro Val Thr Leu
            500                 505                 510

Lys Pro Gly Met Asp Gly Pro Lys Val Lys Gln Trp Pro Leu Thr Glu
```

-continued

```
        515                 520                 525

Glu Lys Ile Lys Ala Leu Thr Glu Ile Cys Thr Glu Met Glu Lys Glu
    530                 535                 540

Gly Lys Ile Ser Lys Ile Gly Pro Glu Asn Pro Tyr Asn Thr Pro Ile
545                 550                 555                 560

Phe Ala Ile Lys Lys Lys Asp Ser Thr Lys Trp Arg Lys Leu Val Asp
                565                 570                 575

Phe Arg Glu Leu Asn Lys Arg Thr Gln Asp Phe Trp Glu Val Gln Leu
            580                 585                 590

Gly Ile Pro His Pro Ala Gly Leu Lys Lys Lys Lys Ser Val Thr Val
        595                 600                 605

Leu Asp Val Gly Asp Ala Tyr Phe Ser Val Pro Leu Asp Glu Asn Phe
    610                 615                 620

Arg Lys Tyr Thr Ala Phe Thr Ile Pro Ser Thr Asn Asn Glu Thr Pro
625                 630                 635                 640

Gly Val Arg Tyr Gln Tyr Asn Val Leu Pro Gln Gly Trp Lys Gly Ser
                645                 650                 655

Pro Ala Ile Phe Gln Ser Ser Met Thr Lys Ile Leu Glu Pro Phe Arg
            660                 665                 670

Ser Lys Asn Pro Glu Ile Ile Ile Tyr Gln Tyr Met Ala Ala Leu Tyr
        675                 680                 685

Val Gly Ser Asp Leu Glu Ile Gly Gln His Arg Thr Lys Ile Glu Glu
    690                 695                 700

Leu Arg Ala His Leu Leu Ser Trp Gly Phe Thr Thr Pro Asp Lys Lys
705                 710                 715                 720

His Gln Lys Glu Pro Pro Phe Leu Trp Met Gly Tyr Glu Leu His Pro
                725                 730                 735

Asp Lys Trp Thr Val Gln Pro Ile Met Leu Pro Asp Lys Glu Ser Trp
            740                 745                 750

Thr Val Asn Asp Ile Gln Lys Leu Val Gly Lys Leu Asn Trp Ala Ser
        755                 760                 765

Gln Ile Tyr Ala Gly Ile Lys Val Lys Gln Leu Cys Arg Leu Leu Arg
    770                 775                 780

Gly Ala Lys Ala Leu Thr Asp Ile Val Thr Leu Thr Glu Glu Ala Glu
785                 790                 795                 800

Leu Glu Leu Ala Glu Asn Arg Glu Ile Leu Lys Asp Pro Val His Gly
                805                 810                 815

Val Tyr Tyr Asp Pro Ser Lys Asp Leu Val Ala Glu Ile Gln Lys Gln
            820                 825                 830

Gly Gln Asp Gln Trp Thr Tyr Gln Ile Tyr Gln Glu Pro Phe Lys Asn
        835                 840                 845

Leu Lys Thr Gly Lys Tyr Ala Arg Lys Arg Ser Ala His Thr Asn Asp
    850                 855                 860

Val Arg Gln Leu Ala Glu Val Val Gln Lys Val Ala Met Glu Ser Ile
865                 870                 875                 880

Val Ile Trp Gly Lys Thr Pro Lys Phe Lys Leu Pro Ile Gln Lys Glu
                885                 890                 895

Thr Trp Glu Thr Trp Trp Met Asp Tyr Trp Gln Ala Thr Trp Ile Pro
            900                 905                 910

Glu Trp Glu Phe Val Asn Thr Pro Pro Leu Val Lys Leu Trp Tyr Gln
        915                 920                 925

Leu Glu Lys Asp Pro Ile Leu Gly Ala Glu Thr Phe Tyr Val Asp Gly
    930                 935                 940
```

```
Ala Ala Asn Arg Glu Thr Lys Leu Gly Lys Ala Gly Tyr Val Thr Asp
945                 950                 955                 960

Arg Gly Arg Gln Lys Val Val Ser Leu Thr Glu Thr Thr Asn Gln Lys
                965                 970                 975

Thr Glu Leu His Ala Ile Leu Leu Ala Leu Gln Asp Ser Gly Ser Glu
            980                 985                 990

Val Asn Ile Val Thr Asp Ser Gln Tyr Ala Leu Gly Ile Ile Gln Ala
        995                 1000                1005

Gln Pro Asp Arg Ser Glu Ser Glu Leu Val Asn Gln Ile Ile Glu Lys
    1010                1015                1020

Leu Ile Gly Lys Asp Lys Ile Tyr Leu Ser Trp Val Pro Ala His Lys
1025                1030                1035                1040

Gly Ile Gly Gly Asn Glu Gln Val Asp Lys Leu Val Ser Ser Gly Ile
                1045                1050                1055

Arg Lys Val Leu Phe Leu Asp Gly Ile Asp Lys Ala Gln Glu Asp His
            1060                1065                1070

Glu Arg Tyr His Ser Asn Trp Arg Thr Met Ala Ser Asp Phe Asn Leu
        1075                1080                1085

Pro Pro Ile Val Ala Lys Glu Ile Val Ala Ser Cys Asp Lys Cys Gln
    1090                1095                1100

Leu Lys Gly Glu Ala Met His Gly Gln Val Asp Cys Ser Pro Gly Ile
1105                1110                1115                1120

Trp Gln Leu Ala Cys Thr His Leu Glu Gly Lys Val Ile Leu Val Ala
                1125                1130                1135

Val His Val Ala Ser Gly Tyr Ile Glu Ala Glu Val Ile Pro Ala Glu
            1140                1145                1150

Thr Gly Gln Glu Thr Ala Tyr Phe Leu Leu Lys Leu Ala Gly Arg Trp
        1155                1160                1165

Pro Val Lys Val Val His Thr Ala Asn Gly Ser Asn Phe Thr Ser Ala
    1170                1175                1180

Ala Val Lys Ala Ala Cys Trp Trp Ala Asn Ile Gln Gln Glu Phe Gly
1185                1190                1195                1200

Ile Pro Tyr Asn Pro Gln Ser Gln Gly Val Val Ala Ser Met Asn Lys
                1205                1210                1215

Glu Leu Lys Lys Ile Ile Gly Gln Val Arg Asp Gln Ala Glu His Leu
            1220                1225                1230

Lys Thr Ala Val Gln Met Ala Val Phe Ile His Asn Phe Lys Arg Lys
        1235                1240                1245

Gly Gly Ile Gly Gly Tyr Ser Ala Gly Glu Arg Ile Ile Asp Ile Ile
    1250                1255                1260

Ala Thr Asp Ile Gln Thr Lys Glu Leu Gln Lys Gln Ile Thr Lys Ile
1265                1270                1275                1280

Gln Asn Phe Arg Val Tyr Tyr Arg Asp Ser Arg Asp Pro Ile Trp Lys
                1285                1290                1295

Gly Pro Ala Lys Leu Leu Trp Lys Gly Glu Gly Ala Val Val Ile Gln
            1300                1305                1310

Asp Asn Ser Asp Ile Lys Val Val Pro Arg Arg Lys Ala Lys Ile Leu
        1315                1320                1325

Arg Asp Tyr Gly Lys Gln Met Ala Gly Asp Asp Cys Val Ala Gly Arg
    1330                1335                1340

Gln Asp Glu Asp Arg Ser Met Gly Gly Lys Trp Ser Lys Gly Ser Ile
1345                1350                1355                1360
```

```
Val Gly Trp Pro Glu Ile Arg Glu Arg Met Arg Arg Ala Pro Ala Ala
                1365                1370                1375

Ala Pro Gly Val Gly Ala Val Ser Gln Asp Leu Asp Lys His Gly Ala
            1380                1385                1390

Ile Thr Ser Ser Asn Ile Asn Asn Pro Ser Cys Val Trp Leu Glu Ala
        1395                1400                1405

Gln Glu Glu Glu Glu Val Gly Phe Pro Val Arg Pro Gln Val Pro Leu
    1410                1415                1420

Arg Pro Met Thr Tyr Lys Gly Ala Phe Asp Leu Ser His Phe Leu Lys
1425                1430                1435                1440

Glu Lys Gly Gly Leu Asp Gly Leu Ile Tyr Ser Arg Lys Arg Gln Glu
                1445                1450                1455

Ile Leu Asp Leu Trp Val Tyr His Thr Gln Gly Tyr Phe Pro Asp Trp
            1460                1465                1470

Gln Asn Tyr Thr Pro Gly Pro Gly Val Arg Tyr Pro Leu Thr Phe Gly
        1475                1480                1485

Trp Cys Phe Lys Leu Val Pro Met Glu Pro Asp Glu Val Glu Lys Ala
    1490                1495                1500

Thr Glu Gly Glu Asn Asn Ser Leu Leu His Pro Ile Cys Gln His Gly
1505                1510                1515                1520

Met Asp Asp Glu Glu Arg Glu Val Leu Ile Trp Lys Phe Asp Ser Arg
                1525                1530                1535

Leu Ala Leu Lys His Arg Ala Gln Glu Leu His Pro Glu Phe Tyr Lys
            1540                1545                1550

Asp Cys


<210> SEQ ID NO 5
<211> LENGTH: 2025
<212> TYPE: DNA
<213> ORGANISM: Artificial Sequence
<220> FEATURE:
<223> OTHER INFORMATION: HIV

<400> SEQUENCE: 5

atgagggtga tggagatcca gcggaactgc cagcacctgc tgagatgggg catcatgatc     60

ctgggcatga ttatcatctg cagcaccgcc gacaacctgt gggtgaccgt gtactacggc    120

gtgcctgtgt ggagagatgc cgagaccacc ctgttctgcg ccagcgacgc caaggcctac    180

agcaccgaga agcacaatgt gtgggccacc cacgcctgcg tgcctaccga tcccaaccct    240

caggagatcc ccctggacaa cgtgaccgag gagttcaaca tgtggaagaa caacatggtg    300

gaccagatgc acgaggacat catcagcctg tgggaccaga gcctgaagcc ctgcgtgcag    360

ctgacccccc tgtgcgtgac cctgaactgc agcaacgcca gagtgaacgc caccttcaac    420

tccaccgagg acagggaggg catgaagaac tgcagcttca acatgaccac cgagctgcgg    480

gataagaagc agcaggtgta cagcctgttc taccggctgg acatcgagaa gatcaacagc    540

agcaacaaca acagcgagta ccggctggtg aactgcaata ccagcgccat cacccaggcc    600

tgccctaagg tgaccttcga gcccatcccc atccactact gcgcccctgc cggcttcgcc    660

atcctgaagt gcaacgacac cgagttcaat ggcaccggcc cctgcaagaa tgtgagcacc    720

gtgcagtgca cccacggcat caagcccgtg gtgtccaccc agctgctgct gaacggcagc    780

ctggccgaga gagaagtgcg gatcaggagc gagaacatcg ccaacaacgc caagaacatc    840

atcgtgcagt tcgccagccc cgtgaagatc aactgcatcc ggcccaacaa caatacccgg    900

aagagctaca gaatcggccc tggccagacc ttctacgcca ccgacattgt gggcgacatc    960
```

agacaggccc actgcaacgt gtccaggacc gactggaaca acaccctgag actggtggcc 1020
aaccagctgc ggaagtactt cagcaacaag accatcatct tcaccaacag cagcggcgga 1080
gacctggaga tcaccaccca cagcttcaat tgtggcggcg agttcttcta ctgcaacacc 1140
tccggcctgt tcaatagcac ctggaccacc aacaacatgc aggagtccaa cgacaccagc 1200
aacggcacca tcaccctgcc ctgccggatc aagcagatca tccggatgtg gcagcgcgtg 1260
ggccaggcca tgtacgcccc tcccatcgag ggcgtgattc gctgcgagag caacatcacc 1320
ggcctgatcc tgaccagaga tggcggcaac aacaattccg ccaacgagac cttcagacct 1380
ggcggcggag atatccggga caactggcgg agcgagctgt acaagtacaa ggtggtgaag 1440
atcgagcccc tgggcgtggc ccccaccaga gccaagagaa gagtggtgga gcgggagaag 1500
agagccgtgg gcatcggcgc cgtgtttctg ggcttcctgg gagccgccgg atctacaatg 1560
ggagccgcca gcatcaccct gaccgtgcag gccagacagc tgctgagcgg catcgtgcag 1620
cagcagagca atctgctgag agccatcgag gcccagcagc agctgctgaa gctgacagtg 1680
tggggcatca agcagctgca ggccagggtg ctggccgtgg agagatacct gagggaccag 1740
cagctcctgg gcatctgggg ctgcagcggc aagctgatct gcaccaccaa cgtgccctgg 1800
aatagcagct ggagcaacaa gagctacgac gacatctggc agaacatgac ctggctgcag 1860
tgggacaagg agatcagcaa ctacaccgac atcatctaca gcctgatcga ggagagccag 1920
aaccagcagg agaagaacga gcaggatctg ctggccctgg acaagtgggc caacctgtgg 1980
aactggttcg acatcagcaa gtggctgtgg tacatcagat cttga 2025

<210> SEQ ID NO 6
<211> LENGTH: 674
<212> TYPE: PRT
<213> ORGANISM: Artificial Sequence
<220> FEATURE:
<223> OTHER INFORMATION: HIV

<400> SEQUENCE: 6

Met Arg Val Met Glu Ile Gln Arg Asn Cys Gln His Leu Leu Arg Trp
1 5 10 15

Gly Ile Met Ile Leu Gly Met Ile Ile Ile Cys Ser Thr Ala Asp Asn
20 25 30

Leu Trp Val Thr Val Tyr Tyr Gly Val Pro Val Trp Arg Asp Ala Glu
35 40 45

Thr Thr Leu Phe Cys Ala Ser Asp Ala Lys Ala Tyr Ser Thr Glu Lys
50 55 60

His Asn Val Trp Ala Thr His Ala Cys Val Pro Thr Asp Pro Asn Pro
65 70 75 80

Gln Glu Ile Pro Leu Asp Asn Val Thr Glu Glu Phe Asn Met Trp Lys
85 90 95

Asn Asn Met Val Asp Gln Met His Glu Asp Ile Ile Ser Leu Trp Asp
100 105 110

Gln Ser Leu Lys Pro Cys Val Gln Leu Thr Pro Leu Cys Val Thr Leu
115 120 125

Asn Cys Ser Asn Ala Arg Val Asn Ala Thr Phe Asn Ser Thr Glu Asp
130 135 140

Arg Glu Gly Met Lys Asn Cys Ser Phe Asn Met Thr Thr Glu Leu Arg
145 150 155 160

Asp Lys Lys Gln Gln Val Tyr Ser Leu Phe Tyr Arg Leu Asp Ile Glu
165 170 175

-continued

```
Lys Ile Asn Ser Ser Asn Asn Asn Ser Glu Tyr Arg Leu Val Asn Cys
            180                 185                 190

Asn Thr Ser Ala Ile Thr Gln Ala Cys Pro Lys Val Thr Phe Glu Pro
        195                 200                 205

Ile Pro Ile His Tyr Cys Ala Pro Ala Gly Phe Ala Ile Leu Lys Cys
    210                 215                 220

Asn Asp Thr Glu Phe Asn Gly Thr Gly Pro Cys Lys Asn Val Ser Thr
225                 230                 235                 240

Val Gln Cys Thr His Gly Ile Lys Pro Val Val Ser Thr Gln Leu Leu
                245                 250                 255

Leu Asn Gly Ser Leu Ala Glu Arg Glu Val Arg Ile Arg Ser Glu Asn
            260                 265                 270

Ile Ala Asn Asn Ala Lys Asn Ile Ile Val Gln Phe Ala Ser Pro Val
        275                 280                 285

Lys Ile Asn Cys Ile Arg Pro Asn Asn Asn Thr Arg Lys Ser Tyr Arg
    290                 295                 300

Ile Gly Pro Gly Gln Thr Phe Tyr Ala Thr Asp Ile Val Gly Asp Ile
305                 310                 315                 320

Arg Gln Ala His Cys Asn Val Ser Arg Thr Asp Trp Asn Asn Thr Leu
                325                 330                 335

Arg Leu Val Ala Asn Gln Leu Arg Lys Tyr Phe Ser Asn Lys Thr Ile
            340                 345                 350

Ile Phe Thr Asn Ser Ser Gly Gly Asp Leu Glu Ile Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Thr Thr Asn Asn Met Gln Glu Ser Asn Asp Thr Ser
385                 390                 395                 400

Asn Gly Thr Ile Thr Leu Pro Cys Arg Ile Lys Gln Ile Ile Arg Met
                405                 410                 415

Trp Gln Arg Val Gly Gln Ala Met Tyr Ala Pro Pro Ile Glu Gly Val
            420                 425                 430

Ile Arg Cys Glu Ser Asn Ile Thr Gly Leu Ile Leu Thr Arg Asp Gly
        435                 440                 445

Gly Asn Asn Asn Ser Ala Asn Glu Thr Phe Arg Pro Gly Gly Gly Asp
    450                 455                 460

Ile Arg Asp Asn Trp Arg Ser Glu Leu Tyr Lys Tyr Lys Val Val Lys
465                 470                 475                 480

Ile Glu Pro Leu Gly Val Ala Pro Thr Arg Ala Lys Arg Arg Val Val
                485                 490                 495

Glu Arg Glu Lys Arg Ala Val Gly Ile Gly Ala Val Phe Leu Gly Phe
            500                 505                 510

Leu Gly Ala Ala Gly Ser Thr Met Gly Ala Ala Ser Ile Thr Leu Thr
        515                 520                 525

Val Gln Ala Arg Gln Leu Leu Ser Gly Ile Val Gln Gln Gln Ser Asn
    530                 535                 540

Leu Leu Arg Ala Ile Glu Ala Gln Gln Gln Leu Leu Lys Leu Thr Val
545                 550                 555                 560

Trp Gly Ile Lys Gln Leu Gln Ala Arg Val Leu Ala Val Glu Arg Tyr
                565                 570                 575

Leu Arg Asp Gln Gln Leu Leu Gly Ile Trp Gly Cys Ser Gly Lys Leu
            580                 585                 590
```

-continued

```
Ile Cys Thr Thr Asn Val Pro Trp Asn Ser Ser Trp Ser Asn Lys Ser
        595                 600                 605

Tyr Asp Asp Ile Trp Gln Asn Met Thr Trp Leu Gln Trp Asp Lys Glu
    610                 615                 620

Ile Ser Asn Tyr Thr Asp Ile Ile Tyr Ser Leu Ile Glu Glu Ser Gln
625                 630                 635                 640

Asn Gln Gln Glu Lys Asn Glu Gln Asp Leu Leu Ala Leu Asp Lys Trp
                645                 650                 655

Ala Asn Leu Trp Asn Trp Phe Asp Ile Ser Lys Trp Leu Trp Tyr Ile
            660                 665                 670

Arg Ser


<210> SEQ ID NO 7
<211> LENGTH: 1545
<212> TYPE: DNA
<213> ORGANISM: Artificial Sequence
<220> FEATURE:
<223> OTHER INFORMATION: HIV

<400> SEQUENCE: 7

atgaaagtga aggagaccag gaagaattat cagcacttgt ggagatgggg caccatgctc      60

cttgggatgt tgatgatctg tagtgctgca gaacaattgt gggtcacagt ctattatggg     120

gtacctgtgt ggaaagaagc aactaccact ctattctgtg catcagatgc taaagcatat     180

gatacagagg tacataatgt ttgggccaca catgcctgtg tacccacaga ccccaaccca     240

caagaagtag tattgggaaa tgtgacagaa tattttaaca tgtggaaaaa taacatggta     300

gaccagatgc atgaggatat aatcagttta tgggatcaaa gcttgaagcc atgtgtaaaa     360

ttaaccccac tctgtgttac tttagattgc gatgatgtga ataccactaa tagtactact     420

accactagta atggttggac aggagaaata aggaaaggag aaataaaaaa ctgctctttt     480

aatatcacca caagcataag agataaggtt caaaaagaat atgcactttt ttataacctt     540

gatgtagtac caatagatga tgataatgct actaccaaaa ataaaactac tagaaacttt     600

aggttgatac attgtaactc ctcagtcatg acacaggcct gtccaaaggt atcatttgaa     660

ccaattccca tacattattg tgccccggct ggttttgcga ttctgaagtg taacaataag     720

acgtttgatg gaaaaggact atgtacaaat gtcagcacag tacaatgtac acatggaatt     780

aggccagtag tgtcaactca actgctgtta aatggcagtc tagcagaaga agaggtagta     840

attagatctg acaatttcat ggacaatact aaaaccataa tagtacagct gaatgaatct     900

gtagcaatta attgtacaag acccaacaac aatacaagaa aaggtataca tataggacca     960

gggagagcct tttatgcagc aagaaaaata ataggagata taagacaagc acattgtaac    1020

cttagtagag cacaatggaa taacacttta aaacagatag ttataaaatt aagagaacac    1080

tttgggaata aaacaataaa atttaatcaa tcctcaggag gggacccaga aattgtaagg    1140

catagtttta attgtggagg ggaatttttc tactgtgata caacacaact gtttaatagt    1200

acttggaatg gtactgaagg aaataacact gaaggaaata gcacaatcac actcccatgt    1260

agaataaaac aaattataaa catgtggcag gaagtaggaa aagcaatgta tgcccctccc    1320

atcggaggac aaattagatg ttcatcaaat attacagggc tgctattaac aagagatggt    1380

ggtaccgaag ggaatgggac agagaatgag acagagatct tcagacctgg aggaggagat    1440

atgagggaca attggagaag tgaattatat aaatataaag tagtaaaagt tgaaccacta    1500

ggagtagcac ccaccagggc aaagagaaga gtggtgcaga gataa                    1545
```

-continued

<210> SEQ ID NO 8
<211> LENGTH: 514
<212> TYPE: PRT
<213> ORGANISM: Artificial Sequence
<220> FEATURE:
<223> OTHER INFORMATION: HIV

<400> SEQUENCE: 8

```
Met Lys Val Lys Glu Thr Arg Lys Asn Tyr Gln His Leu Trp Arg Trp
1               5                   10                  15

Gly Thr Met Leu Leu Gly Met Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Tyr Phe Asn Met Trp Lys
                85                  90                  95

Asn Asn Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asp Cys Asp Asp Val Asn Thr Thr Asn Ser Thr Thr Thr Thr Ser Asn
    130                 135                 140

Gly Trp Thr Gly Glu Ile Arg Lys Gly Glu Ile Lys Asn Cys Ser Phe
145                 150                 155                 160

Asn Ile Thr Thr Ser Ile Arg Asp Lys Val Gln Lys Glu Tyr Ala Leu
                165                 170                 175

Phe Tyr Asn Leu Asp Val Val Pro Ile Asp Asp Asp Asn Ala Thr Thr
            180                 185                 190

Lys Asn Lys Thr Thr Arg Asn Phe Arg Leu Ile His Cys Asn Ser Ser
        195                 200                 205

Val Met Thr Gln Ala Cys Pro Lys Val Ser Phe Glu Pro Ile Pro Ile
    210                 215                 220

His Tyr Cys Ala Pro Ala Gly Phe Ala Ile Leu Lys Cys Asn Asn Lys
225                 230                 235                 240

Thr Phe Asp Gly Lys Gly Leu Cys Thr Asn Val Ser Thr Val Gln Cys
                245                 250                 255

Thr His Gly Ile Arg Pro Val Val Ser Thr Gln Leu Leu Leu Asn Gly
            260                 265                 270

Ser Leu Ala Glu Glu Glu Val Val Ile Arg Ser Asp Asn Phe Met Asp
        275                 280                 285

Asn Thr Lys Thr Ile Ile Val Gln Leu Asn Glu Ser Val Ala Ile Asn
    290                 295                 300

Cys Thr Arg Pro Asn Asn Asn Thr Arg Lys Gly Ile His Ile Gly Pro
305                 310                 315                 320

Gly Arg Ala Phe Tyr Ala Ala Arg Lys Ile Ile Gly Asp Ile Arg Gln
                325                 330                 335

Ala His Cys Asn Leu Ser Arg Ala Gln Trp Asn Asn Thr Leu Lys Gln
            340                 345                 350

Ile Val Ile Lys Leu Arg Glu His Phe Gly Asn Lys Thr Ile Lys Phe
        355                 360                 365
```

-continued

```
Asn Gln Ser Ser Gly Gly Asp Pro Glu Ile Val Arg His Ser Phe Asn
    370                 375                 380

Cys Gly Gly Glu Phe Phe Tyr Cys Asp Thr Thr Gln Leu Phe Asn Ser
385                 390                 395                 400

Thr Trp Asn Gly Thr Glu Gly Asn Asn Thr Glu Gly Asn Ser Thr Ile
                405                 410                 415

Thr Leu Pro Cys Arg Ile Lys Gln Ile Ile Asn Met Trp Gln Glu Val
            420                 425                 430

Gly Lys Ala Met Tyr Ala Pro Pro Ile Gly Gly Gln Ile Arg Cys Ser
        435                 440                 445

Ser Asn Ile Thr Gly Leu Leu Leu Thr Arg Asp Gly Gly Thr Glu Gly
    450                 455                 460

Asn Gly Thr Glu Asn Glu Thr Glu Ile Phe Arg Pro Gly Gly Gly Asp
465                 470                 475                 480

Met Arg Asp Asn Trp Arg Ser Glu Leu Tyr Lys Tyr Lys Val Val Lys
                485                 490                 495

Val Glu Pro Leu Gly Val Ala Pro Thr Arg Ala Lys Arg Arg Val Val
            500                 505                 510

Gln Arg


<210> SEQ ID NO 9
<211> LENGTH: 2178
<212> TYPE: DNA
<213> ORGANISM: Artificial Sequence
<220> FEATURE:
<223> OTHER INFORMATION: Mycobacterium tuberculosis

<400> SEQUENCE: 9

atgcatcaca cggccgcgtc cgataacttc cagctgtccc agggtgggca gggattcgcc     60

attccgatcg ggcaggcgat ggcgatcgcg ggccagatcc gatcgggtgg ggggtcaccc    120

accgttcata tcgggcctac cgccttcctc ggcttgggtg ttgtcgacaa caacggcaac    180

ggcgcacgag tccaacgcgt ggtcgggagc gctccggcgg caagtctcgg catctccacc    240

ggcgacgtga tcaccgcggt cgacggcgct ccgatcaact cggccaccgc gatggcggac    300

gcgcttaacg ggcatcatcc cggtgacgtc atctcggtga cctggcaaac caagtcgggc    360

ggcacgcgta cagggaacgt gacattggcc gagggacccc cggccgaatt catggtggat    420

ttcggggcgt taccaccgga gatcaactcc gcgaggatgt acgccggccc gggttcggcc    480

tcgctggtgg ccgcggctca gatgtgggac agcgtggcga gtgacctgtt ttcggccgcg    540

tcggcgtttc agtcggtggt ctggggtctg acggtggggt cgtggatagg ttcgtcggcg    600

ggtctgatgg tggcggcggc ctcgccgtat gtggcgtgga tgagcgtcac cgcggggcag    660

gccgagctga ccgccgccca ggtccgggtt gctgcggcgg cctacgagac ggcgtatggg    720

ctgacggtgc ccccgccggt gatcgccgag aaccgtgctg aactgatgat tctgatagcg    780

accaacctct tggggcaaaa caccccggcg atcgcggtca acgaggccga atacggcgag    840

atgtgggccc aagacgccgc cgcgatgttt ggctacgccg cggcgacggc gacggcgacg    900

gcgacgttgc tgccgttcga ggaggcgccg gagatgacca gcgcgggtgg gctcctcgag    960

caggccgccg cggtcgagga ggcctccgac accgccgcgg cgaaccagtt gatgaacaat   1020

gtgccccagg cgctgcaaca gctggcccag cccacgcagg gcaccacgcc ttcttccaag   1080

ctgggtggcc tgtggaagac ggtctcgccg catcggtcgc cgatcagcaa catggtgtcg   1140

atggccaaca accacatgtc gatgaccaac tcgggtgtgt cgatgaccaa caccttgagc   1200
```

-continued

```
tcgatgttga agggctttgc tccggcggcg gccgcccagg ccgtgcaaac cgcggcgcaa   1260

aacggggtcc gggcgatgag ctcgctgggc agctcgctgg gttcttcggg tctgggcggt   1320

ggggtggccg ccaacttggg tcgggcggcc tcggtcggtt cgttgtcggt gccgcaggcc   1380

tgggccgcgg ccaaccaggc agtcaccccg gcggcgcggg cgctgccgct gaccagcctg   1440

accagcgccg cggaaagagg gcccgggcag atgctgggcg ggctgccggt ggggcagatg   1500

ggcgccaggg ccggtggtgg gctcagtggt gtgctgcgtg ttccgccgcg accctatgtg   1560

atgccgcatt ctccggcagc cggcgatatc gccccgccgg ccttgtcgca ggaccggttc   1620

gccgacttcc ccgcgctgcc cctcgacccg tccgcgatgg tcgcccaagt ggggccacag   1680

gtggtcaaca tcaacaccaa actgggctac aacaacgccg tgggcgccgg gaccggcatc   1740

gtcatcgatc ccaacggtgt cgtgctgacc aacaaccacg tgatcgcggg cgccaccgac   1800

atcaatgcgt tcagcgtcgg ctccggccaa acctacggcg tcgatgtggt cgggtatgac   1860

cgcacccagg atgtcgcggt gctgcagctg cgcggtgccg gtggcctgcc gtcggcggcg   1920

atcggtggcg gcgtcgcggt tggtgagccc gtcgtcgcga tgggcaacag cggtgggcag   1980

ggcggaacgc cccgtgcggt gcctggcagg gtggtcgcgc tcggccaaac cgtgcaggcg   2040

tcggattcgc tgaccggtgc cgaagagaca ttgaacgggt tgatccagtt cgatgccgcg   2100

atccagcccg gtgatgcggg cgggcccgtc gtcaacggcc taggacaggt ggtcggtatg   2160

aacacggccg cgtcctag                                                 2178
```

<210> SEQ ID NO 10
<211> LENGTH: 725
<212> TYPE: PRT
<213> ORGANISM: Artificial Sequence
<220> FEATURE:
<223> OTHER INFORMATION: Mycobacterium tuberculosis

<400> SEQUENCE: 10

```
Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
            20                  25                  30

Ile Arg Ser Gly Gly Gly Ser Pro Thr Val His Ile Gly Pro Thr Ala
        35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
145                 150                 155                 160

Ser Leu Val Ala Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
            180                 185                 190
```

-continued

```
Gly Ser Trp Ile Gly Ser Ser Ala Gly Leu Met Val Ala Ala Ala Ser
        195                 200                 205

Pro Tyr Val Ala Trp Met Ser Val Thr Ala Gly Gln Ala Glu Leu Thr
    210                 215                 220

Ala Ala Gln Val Arg Val Ala Ala Ala Ala Tyr Glu Thr Ala Tyr Gly
225                 230                 235                 240

Leu Thr Val Pro Pro Pro Val Ile Ala Glu Asn Arg Ala Glu Leu Met
                245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
        275                 280                 285

Met Phe Gly Tyr Ala Ala Ala Thr Ala Thr Ala Thr Ala Thr Leu Leu
    290                 295                 300

Pro Phe Glu Glu Ala Pro Glu Met Thr Ser Ala Gly Gly Leu Leu Glu
305                 310                 315                 320

Gln Ala Ala Ala Val Glu Glu Ala Ser Asp Thr Ala Ala Ala Asn Gln
                325                 330                 335

Leu Met Asn Asn Val Pro Gln Ala Leu Gln Gln Leu Ala Gln Pro Thr
            340                 345                 350

Gln Gly Thr Thr Pro Ser Ser Lys Leu Gly Gly Leu Trp Lys Thr Val
        355                 360                 365

Ser Pro His Arg Ser Pro Ile Ser Asn Met Val Ser Met Ala Asn Asn
    370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Ala Gln Ala Val Gln
                405                 410                 415

Thr Ala Ala Gln Asn Gly Val Arg Ala Met Ser Ser Leu Gly Ser Ser
            420                 425                 430

Leu Gly Ser Ser Gly Leu Gly Gly Gly Val Ala Ala Asn Leu Gly Arg
        435                 440                 445

Ala Ala Ser Val Gly Ser Leu Ser Val Pro Gln Ala Trp Ala Ala Ala
    450                 455                 460

Asn Gln Ala Val Thr Pro Ala Ala Arg Ala Leu Pro Leu Thr Ser Leu
465                 470                 475                 480

Thr Ser Ala Ala Glu Arg Gly Pro Gly Gln Met Leu Gly Gly Leu Pro
                485                 490                 495

Val Gly Gln Met Gly Ala Arg Ala Gly Gly Gly Leu Ser Gly Val Leu
            500                 505                 510

Arg Val Pro Pro Arg Pro Tyr Val Met Pro His Ser Pro Ala Ala Gly
        515                 520                 525

Asp Ile Ala Pro Pro Ala Leu Ser Gln Asp Arg Phe Ala Asp Phe Pro
    530                 535                 540

Ala Leu Pro Leu Asp Pro Ser Ala Met Val Ala Gln Val Gly Pro Gln
545                 550                 555                 560

Val Val Asn Ile Asn Thr Lys Leu Gly Tyr Asn Asn Ala Val Gly Ala
                565                 570                 575

Gly Thr Gly Ile Val Ile Asp Pro Asn Gly Val Val Leu Thr Asn Asn
            580                 585                 590

His Val Ile Ala Gly Ala Thr Asp Ile Asn Ala Phe Ser Val Gly Ser
        595                 600                 605
```

-continued

```
Gly Gln Thr Tyr Gly Val Asp Val Val Gly Tyr Asp Arg Thr Gln Asp
    610                 615                 620

Val Ala Val Leu Gln Leu Arg Gly Ala Gly Gly Leu Pro Ser Ala Ala
625                 630                 635                 640

Ile Gly Gly Gly Val Ala Val Gly Glu Pro Val Val Ala Met Gly Asn
                645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
        675                 680                 685

Glu Thr Leu Asn Gly Leu Ile Gln Phe Asp Ala Ala Ile Gln Pro Gly
    690                 695                 700

Asp Ala Gly Gly Pro Val Val Asn Gly Leu Gly Gln Val Val Gly Met
705                 710                 715                 720

Asn Thr Ala Ala Ser
                725
```

<210> SEQ ID NO 11
<211> LENGTH: 1149
<212> TYPE: DNA
<213> ORGANISM: Artificial Sequence
<220> FEATURE:
<223> OTHER INFORMATION: Plasmodium falciparum

<400> SEQUENCE: 11

```
atgatgagaa aacttgccat cctcagcgtc agctctttcc tgttcgtgga ggccctcttc      60

caggagtatc agtgctacgg aagcagcagc aatacaaggg tcctgaacga gctcaactat     120

gacaacgctg gaacgaacct gtataacgag ctggagatga actactatgg caagcaggag     180

aactggtata gcctgaagaa gaacagccgg tccctgggcg agaacgacga cggcaacaac     240

aacaacggcg acaacggcag ggagggcaaa gatgaggaca agagggacgg gaacaacgag     300

gataacgaga agctgcggaa gcccaagcac aagaaactca agcagcccgc cgacgggaac     360

ccggacccca atgcaaatcc caacgtcgac ccaaacgcaa accctaacgt ggaccccaac     420

gccaatccca acgtcgatcc taatgccaat ccaaatgcca accctaacgc aaatcctaat     480

gcaaacccca acgccaatcc taacgccaac ccaaatgcca acccaaacgc taaccccaac     540

gctaacccaa atgcaaatcc caatgctaac ccaaacgtgg accctaacgc taaccccaac     600

gcaaacccta acgccaatcc taacgcaaac cccaatgcaa acccaaacgc aaatcccaac     660

gctaacccta acgcaaaccc caacgccaac cctaatgcca accccaatgc taaccccaac     720

gccaatccaa acgcaaatcc aaacgccaac ccaaatgcaa accccaacgc taatcccaac     780

gccaacccaa acgccaatcc taacaagaac aatcagggca acgggcaggg ccataacatg     840

ccgaacgacc ctaatcggaa tgtggacgag aacgccaacg ccaacagcgc cgtgaagaac     900

aacaacaacg aggagccctc cgacaagcac atcaaggaat acctgaacaa gatccagaac     960

agtctgagca ccgagtggtc cccctgctcc gtgacctgcg gcaacggcat ccaggtgagg    1020

atcaagcccg gctccgccaa caagcccaag gacgagctgg actacgccaa cgacatcgag    1080

aagaagatct gcaagatgga gaaatgcagc tctgtgttca acgtcgtgaa ctccgccatc    1140

ggcctgtga                                                            1149
```

<210> SEQ ID NO 12
<211> LENGTH: 382
<212> TYPE: PRT
<213> ORGANISM: Artificial Sequence
<220> FEATURE:
<223> OTHER INFORMATION: Plasmodium falciparum

<400> SEQUENCE: 12

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Ala Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Val Asp Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Lys Asn Asn Gln
            260                 265                 270

Gly Asn Gly Gln Gly His Asn Met Pro Asn Asp Pro Asn Arg Asn Val
        275                 280                 285

Asp Glu Asn Ala Asn Ala Asn Ser Ala Val Lys Asn Asn Asn Asn Glu
    290                 295                 300

Glu Pro Ser Asp Lys His Ile Lys Glu Tyr Leu Asn Lys Ile Gln Asn
305                 310                 315                 320

Ser Leu Ser Thr Glu Trp Ser Pro Cys Ser Val Thr Cys Gly Asn Gly
                325                 330                 335

Ile Gln Val Arg Ile Lys Pro Gly Ser Ala Asn Lys Pro Lys Asp Glu
            340                 345                 350

Leu Asp Tyr Ala Asn Asp Ile Glu Lys Lys Ile Cys Lys Met Glu Lys
        355                 360                 365

Cys Ser Ser Val Phe Asn Val Val Asn Ser Ala Ile Gly Leu
    370                 375                 380
```

<210> SEQ ID NO 13

<211> LENGTH: 1275
<212> TYPE: DNA
<213> ORGANISM: Artificial Sequence
<220> FEATURE:
<223> OTHER INFORMATION: Plasmodium falciparum

<400> SEQUENCE: 13

```
atgatggctc ccgatcctaa tgcaaatcca aatgcaaacc caaacgcaaa ccccaatgca     60

aatcctaatg caaaccccaa tgcaaatcct aatgcaaatc ctaatgccaa tccaaatgca    120

aatccaaatg caaacccaaa cgcaaacccc aatgcaaatc ctaatgccaa tccaaatgca    180

aatccaaatg caaacccaaa tgcaaaccca aatgcaaacc ccaatgcaaa tcctaataaa    240

aacaatcaag gtaatggaca aggtcacaat atgccaaatg acccaaaccg aaatgtagat    300

gaaaatgcta atgccaacag tgctgtaaaa aataataata acgaagaacc aagtgataag    360

cacataaaag aatatttaaa caaaatacaa aattctcttt caactgaatg gtccccatgt    420

agtgtaactt gtggaaatgg tattcaagtt agaataaagc ctggctctgc taataaacct    480

aaagacgaat tagattatgc aaatgatatt gaaaaaaaaa tttgtaaaat ggaaaaatgt    540

tccagtgtgt ttaatgtcgt aaatagttca ataggattag ggcctgtgac gaacatggag    600

aacatcacat caggattcct aggacccctg ctcgtgttac aggcggggtt tttcttgttg    660

acaagaatcc tcacaatacc gcagagtcta gactcgtggt ggacttctct caattttcta    720

gggggatcac ccgtgtgtct tggccaaaat tcgcagtccc caacctccaa tcactcacca    780

acctcctgtc ctccaatttg tcctggttat cgctggatgt gtctgcggcg ttttatcata    840

ttcctcttca tcctgctgct atgcctcatc ttcttattgg ttcttctgga ttatcaaggt    900

atgttgcccg tttgtcctct aattccagga tcaacaacaa ccaatacggg accatgcaaa    960

acctgcacga ctcctgctca aggcaactct atgtttccct catgttgctg tacaaaacct   1020

acggatggaa attgcacctg tattcccatc ccatcgtcct gggctttcgc aaaataccta   1080

tgggagtggg cctcagtccg tttctcttgg ctcagtttac tagtgccatt tgttcagtgg   1140

ttcgtagggc tttcccccac tgtttggctt tcagctatat ggatgatgtg gtattggggg   1200

ccaagtctgt acagcatcgt gagtcccttt ataccgctgt taccaatttt cttttgtctc   1260

tgggtataca tttaa                                                     1275
```

<210> SEQ ID NO 14
<211> LENGTH: 424
<212> TYPE: PRT
<213> ORGANISM: Artificial Sequence
<220> FEATURE:
<223> OTHER INFORMATION: Plasmodium falciparum

<400> SEQUENCE: 14

```
Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95
```

```
Arg Asn Val Asp Glu Asn Ala Asn Ala Asn Ser Ala Val Lys Asn Asn
            100                 105                 110

Asn Asn Glu Glu Pro Ser Asp Lys His Ile Lys Glu Tyr Leu Asn Lys
        115                 120                 125

Ile Gln Asn Ser Leu Ser Thr Glu Trp Ser Pro Cys Ser Val Thr Cys
    130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
            180                 185                 190

Leu Gly Pro Val Thr Asn Met Glu Asn Ile Thr Ser Gly Phe Leu Gly
        195                 200                 205

Pro Leu Leu Val Leu Gln Ala Gly Phe Phe Leu Leu Thr Arg Ile Leu
    210                 215                 220

Thr Ile Pro Gln Ser Leu Asp Ser Trp Trp Thr Ser Leu Asn Phe Leu
225                 230                 235                 240

Gly Gly Ser Pro Val Cys Leu Gly Gln Asn Ser Gln Ser Pro Thr Ser
                245                 250                 255

Asn His Ser Pro Thr Ser Cys Pro Pro Ile Cys Pro Gly Tyr Arg Trp
            260                 265                 270

Met Cys Leu Arg Arg Phe Ile Ile Phe Leu Phe Ile Leu Leu Leu Cys
        275                 280                 285

Leu Ile Phe Leu Leu Val Leu Leu Asp Tyr Gln Gly Met Leu Pro Val
    290                 295                 300

Cys Pro Leu Ile Pro Gly Ser Thr Thr Thr Asn Thr Gly Pro Cys Lys
305                 310                 315                 320

Thr Cys Thr Thr Pro Ala Gln Gly Asn Ser Met Phe Pro Ser Cys Cys
                325                 330                 335

Cys Thr Lys Pro Thr Asp Gly Asn Cys Thr Cys Ile Pro Ile Pro Ser
            340                 345                 350

Ser Trp Ala Phe Ala Lys Tyr Leu Trp Glu Trp Ala Ser Val Arg Phe
        355                 360                 365

Ser Trp Leu Ser Leu Leu Val Pro Phe Val Gln Trp Phe Val Gly Leu
    370                 375                 380

Ser Pro Thr Val Trp Leu Ser Ala Ile Trp Met Met Trp Tyr Trp Gly
385                 390                 395                 400

Pro Ser Leu Tyr Ser Ile Val Ser Pro Phe Ile Pro Leu Leu Pro Ile
                405                 410                 415

Phe Phe Cys Leu Trp Val Tyr Ile
            420
```

<210> SEQ ID NO 15
<211> LENGTH: 3411
<212> TYPE: DNA
<213> ORGANISM: Artificial Sequence
<220> FEATURE:
<223> OTHER INFORMATION: HIV

<400> SEQUENCE: 15

```
atggtcattg ttcagaacat acagggccaa atggtccacc aggcaattag tccgcgaact     60

cttaatgcat gggtgaaggt cgtggaggaa aaggcattct ccccggaggt cattccgatg    120

ttttctgcgc tatctgaggg cgcaacgccg caagacctta ataccatgct taacacggta    180
```

```
ggcgggcacc aagccgctat gcaaatgcta aaagagacta taaacgaaga ggccgccgaa    240
tgggatcgag tgcacccggt gcacgccggc ccaattgcac caggccagat gcgcgagccg    300
cgcgggtctg atattgcagg aactacgtct acccttcagg agcagattgg gtggatgact    360
aacaatccac caatcccggt cggagagatc tataagaggt ggatcatact gggactaaac    420
aagatagtcc gcatgtattc tccgacttct atactggata tacgccaagg cccaaaggag    480
ccgttcaggg actatgtcga ccgattctat aagacccttc gcgcagagca ggcatcccag    540
gaggtcaaaa attggatgac agaaactctt ttggtgcaga atgcgaatcc ggattgtaaa    600
acaattttaa aggctctagg accggccgca acgctagaag agatgatgac ggcttgtcag    660
ggagtcggtg gaccggggca taaagcccgc gtcttacaca tgggcccgat atctccgata    720
gaaacagttt cggtcaagct taaaccaggg atggatggtc caaaggtcaa gcagtggccg    780
ctaacggaag agaagattaa ggcgctcgta gagatttgta ctgaaatgga gaaggaaggc    840
aagataagca agatcgggcc agagaacccg tacaatacac cggtatttgc aataaagaaa    900
aaggattcaa caaaatggcg aaagcttgta gattttaggg aactaaacaa gcgaacccaa    960
gacttttggg aagtccaact agggatccca catccagccg gtctaaagaa gaagaaatcg   1020
gtcacagtcc tggatgtagg agacgcatat tttagtgtac cgcttgatga ggacttccga   1080
aagtatactg cgtttactat accgagcata aacaatgaaa cgccaggcat tcgctatcag   1140
tacaacgtgc tcccgcaggg ctggaagggg tctccggcga tatttcagag ctgtatgaca   1200
aaaatacttg aaccattccg aaagcagaat ccggatattg taatttacca atacatggac   1260
gatctctatg tgggctcgga tctagaaatt gggcagcatc gcactaagat tgaggaactg   1320
aggcaacatc tgcttcgatg gggcctcact actcccgaca agaagcacca gaaggagccg   1380
ccgttcctaa agatgggcta cgagcttcat ccggacaagt ggacagtaca gccgatagtg   1440
ctgcccgaaa aggattcttg gaccgtaaat gatattcaga aactagtcgg caagcttaac   1500
tgggcctctc agatttaccc aggcattaag gtccgacagc tttgcaagct actgagggga   1560
actaaggctc taacagaggt catcccatta acggaggaag cagagcttga gctggcagag   1620
aatcgcgaaa ttcttaagga gccggtgcac ggggtatact acgacccctc caaggacctt   1680
atagccgaga tccagaagca ggggcagggc caatggacgt accagatata tcaagaaccg   1740
tttaagaatc tgaagactgg gaagtacgcg cgcatgcgag ggctcatac taatgatgta    1800
aagcaactta cggaagcagt acaaaagatt actactgagt ctattgtgat atggggcaag   1860
accccaaagt tcaagctgcc catacagaag gaaacatggg aaacatggtg gactgaatat   1920
tggcaagcta cctggattcc agaatgggaa tttgtcaaca cgccgccact tgttaagctt   1980
tggtaccagc ttgaaaagga gccgatagta ggggcagaga ccttctatgt cgatggcgcc   2040
gcgaatcgcg aaacgaagct aggcaaggcg ggatacgtga ctaatagggg ccgccaaaag   2100
gtcgtaaccc ttacggatac caccaatcag aagactgaac tacaagcgat ttaccttgca   2160
cttcaggata gtggcctaga ggtcaacata gtcacggact ctcaatatgc gcttggcatt   2220
attcaagcgc agccagatca aagcgaaagc gagcttgtaa accaaataat agaacagctt   2280
ataaagaaag agaaggtata tctggcctgg gtccccgctc acaagggaat tggcggcaat   2340
gagcaagtgg acaagctagt cagcgctggg attcgcaagg ttcttgcgat ggggggtaag   2400
tggtctaagt ctagcgtagt cggctggccg acagtccgcg agcgcatgcg acgcgccgaa   2460
ccagccgcag atggcgtggg ggcagcgtct agggatctgg agaagcacgg ggctataact   2520
```

-continued

```
tccagtaaca cggcggcgac gaacgccgca tgcgcatggt tagaagccca agaagaggaa   2580

gaagtagggt ttccggtaac tccccaggtg ccgttaaggc cgatgaccta taaggcagcg   2640

gtggatcttt ctcacttcct taaggagaaa ggggggctgg agggcttaat tcacagccag   2700

aggcgacagg atattcttga tctgtggatt taccataccc aggggtactt tccggactgg   2760

cagaattaca ccccggggcc aggcgtgcgc tatcccctga ctttcgggtg gtgctacaaa   2820

ctagtcccag tggaacccga caaggtcgaa gaggctaata agggcgagaa cacttctctt   2880

cttcacccgg taagcctgca cgggatggat gacccagaac gagaggttct agaatggagg   2940

ttcgactctc gacttgcgtt ccatcacgta gcacgcgagc tgcatccaga atatttcaag   3000

aactgccgcc caatgggcgc cagggccagt gtacttagtg gcggagaact agatcgatgg   3060

gaaaagatac gcctacgccc gggggcaag aagaagtaca agcttaagca cattgtgtgg    3120

gcctctcgcg aacttgagcg attcgcagtg aatccaggcc tgcttgagac gagtgaaggc   3180

tgtaggcaaa ttctggggca gctacagccg agcctacaga ctggcagcga ggagcttcgt   3240

agtctttata ataccgtcgc gactctctac tgcgttcatc aacgaattga aataaaggat   3300

actaaagagg cccttgataa aattgaggag gaacagaata agtcgaaaaa gaaggcccag   3360

caggccgccg ccgacaccgg gcacagcaac caggtgtccc aaaactacta a            3411
```

```
<210> SEQ ID NO 16
<211> LENGTH: 1136
<212> TYPE: PRT
<213> ORGANISM: Artificial Sequence
<220> FEATURE:
<223> OTHER INFORMATION: HIV

<400> SEQUENCE: 16

Met Val Ile Val Gln Asn Ile Gln Gly Gln Met Val His Gln Ala Ile
1               5                   10                  15

Ser Pro Arg Thr Leu Asn Ala Trp Val Lys Val Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Val His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205
```

-continued

```
Ala Ala Thr Leu Glu Glu Met Met Thr Ala Cys Gln Gly Val Gly Gly
    210                 215                 220

Pro Gly His Lys Ala Arg Val Leu His Met Gly Pro Ile Ser Pro Ile
225                 230                 235                 240

Glu Thr Val Ser Val Lys Leu Lys Pro Gly Met Asp Gly Pro Lys Val
                245                 250                 255

Lys Gln Trp Pro Leu Thr Glu Glu Lys Ile Lys Ala Leu Val Glu Ile
            260                 265                 270

Cys Thr Glu Met Glu Lys Glu Gly Lys Ile Ser Lys Ile Gly Pro Glu
        275                 280                 285

Asn Pro Tyr Asn Thr Pro Val Phe Ala Ile Lys Lys Lys Asp Ser Thr
    290                 295                 300

Lys Trp Arg Lys Leu Val Asp Phe Arg Glu Leu Asn Lys Arg Thr Gln
305                 310                 315                 320

Asp Phe Trp Glu Val Gln Leu Gly Ile Pro His Pro Ala Gly Leu Lys
                325                 330                 335

Lys Lys Lys Ser Val Thr Val Leu Asp Val Gly Asp Ala Tyr Phe Ser
            340                 345                 350

Val Pro Leu Asp Glu Asp Phe Arg Lys Tyr Thr Ala Phe Thr Ile Pro
        355                 360                 365

Ser Ile Asn Asn Glu Thr Pro Gly Ile Arg Tyr Gln Tyr Asn Val Leu
    370                 375                 380

Pro Gln Gly Trp Lys Gly Ser Pro Ala Ile Phe Gln Ser Cys Met Thr
385                 390                 395                 400

Lys Ile Leu Glu Pro Phe Arg Lys Gln Asn Pro Asp Ile Val Ile Tyr
                405                 410                 415

Gln Tyr Met Asp Asp Leu Tyr Val Gly Ser Asp Leu Glu Ile Gly Gln
            420                 425                 430

His Arg Thr Lys Ile Glu Glu Leu Arg Gln His Leu Leu Arg Trp Gly
        435                 440                 445

Leu Thr Thr Pro Asp Lys Lys His Gln Lys Glu Pro Pro Phe Leu Lys
    450                 455                 460

Met Gly Tyr Glu Leu His Pro Asp Lys Trp Thr Val Gln Pro Ile Val
465                 470                 475                 480

Leu Pro Glu Lys Asp Ser Trp Thr Val Asn Asp Ile Gln Lys Leu Val
                485                 490                 495

Gly Lys Leu Asn Trp Ala Ser Gln Ile Tyr Pro Gly Ile Lys Val Arg
            500                 505                 510

Gln Leu Cys Lys Leu Leu Arg Gly Thr Lys Ala Leu Thr Glu Val Ile
        515                 520                 525

Pro Leu Thr Glu Glu Ala Glu Leu Glu Leu Ala Glu Asn Arg Glu Ile
    530                 535                 540

Leu Lys Glu Pro Val His Gly Val Tyr Tyr Asp Pro Ser Lys Asp Leu
545                 550                 555                 560

Ile Ala Glu Ile Gln Lys Gln Gly Gln Gly Gln Trp Thr Tyr Gln Ile
                565                 570                 575

Tyr Gln Glu Pro Phe Lys Asn Leu Lys Thr Gly Lys Tyr Ala Arg Met
            580                 585                 590

Arg Gly Ala His Thr Asn Asp Val Lys Gln Leu Thr Glu Ala Val Gln
        595                 600                 605

Lys Ile Thr Thr Glu Ser Ile Val Ile Trp Gly Lys Thr Pro Lys Phe
    610                 615                 620

Lys Leu Pro Ile Gln Lys Glu Thr Trp Glu Thr Trp Trp Thr Glu Tyr
```

-continued

```
625                 630                 635                 640

Trp Gln Ala Thr Trp Ile Pro Glu Trp Glu Phe Val Asn Thr Pro Pro
                645                 650                 655

Leu Val Lys Leu Trp Tyr Gln Leu Glu Lys Glu Pro Ile Val Gly Ala
            660                 665                 670

Glu Thr Phe Tyr Val Asp Gly Ala Ala Asn Arg Glu Thr Lys Leu Gly
        675                 680                 685

Lys Ala Gly Tyr Val Thr Asn Arg Gly Arg Gln Lys Val Val Thr Leu
    690                 695                 700

Thr Asp Thr Thr Asn Gln Lys Thr Glu Leu Gln Ala Ile Tyr Leu Ala
705                 710                 715                 720

Leu Gln Asp Ser Gly Leu Glu Val Asn Ile Val Thr Asp Ser Gln Tyr
                725                 730                 735

Ala Leu Gly Ile Ile Gln Ala Gln Pro Asp Gln Ser Glu Ser Glu Leu
            740                 745                 750

Val Asn Gln Ile Ile Glu Gln Leu Ile Lys Lys Glu Lys Val Tyr Leu
        755                 760                 765

Ala Trp Val Pro Ala His Lys Gly Ile Gly Gly Asn Glu Gln Val Asp
    770                 775                 780

Lys Leu Val Ser Ala Gly Ile Arg Lys Val Leu Ala Met Gly Gly Lys
785                 790                 795                 800

Trp Ser Lys Ser Ser Val Val Gly Trp Pro Thr Val Arg Glu Arg Met
                805                 810                 815

Arg Arg Ala Glu Pro Ala Ala Asp Gly Val Gly Ala Ala Ser Arg Asp
            820                 825                 830

Leu Glu Lys His Gly Ala Ile Thr Ser Ser Asn Thr Ala Ala Thr Asn
        835                 840                 845

Ala Ala Cys Ala Trp Leu Glu Ala Gln Glu Glu Glu Glu Val Gly Phe
    850                 855                 860

Pro Val Thr Pro Gln Val Pro Leu Arg Pro Met Thr Tyr Lys Ala Ala
865                 870                 875                 880

Val Asp Leu Ser His Phe Leu Lys Glu Lys Gly Gly Leu Glu Gly Leu
                885                 890                 895

Ile His Ser Gln Arg Arg Gln Asp Ile Leu Asp Leu Trp Ile Tyr His
            900                 905                 910

Thr Gln Gly Tyr Phe Pro Asp Trp Gln Asn Tyr Thr Pro Gly Pro Gly
        915                 920                 925

Val Arg Tyr Pro Leu Thr Phe Gly Trp Cys Tyr Lys Leu Val Pro Val
    930                 935                 940

Glu Pro Asp Lys Val Glu Glu Ala Asn Lys Gly Glu Asn Thr Ser Leu
945                 950                 955                 960

Leu His Pro Val Ser Leu His Gly Met Asp Asp Pro Glu Arg Glu Val
                965                 970                 975

Leu Glu Trp Arg Phe Asp Ser Arg Leu Ala Phe His His Val Ala Arg
            980                 985                 990

Glu Leu His Pro Glu Tyr Phe Lys Asn Cys Arg Pro Met Gly Ala Arg
        995                 1000                1005

Ala Ser Val Leu Ser Gly Gly Glu Leu Asp Arg Trp Glu Lys Ile Arg
    1010                1015                1020

Leu Arg Pro Gly Gly Lys Lys Lys Tyr Lys Leu Lys His Ile Val Trp
1025                1030                1035                1040

Ala Ser Arg Glu Leu Glu Arg Phe Ala Val Asn Pro Gly Leu Leu Glu
                1045                1050                1055
```

-continued

```
Thr Ser Glu Gly Cys Arg Gln Ile Leu Gly Gln Leu Gln Pro Ser Leu
            1060                1065                1070

Gln Thr Gly Ser Glu Glu Leu Arg Ser Leu Tyr Asn Thr Val Ala Thr
        1075                1080                1085

Leu Tyr Cys Val His Gln Arg Ile Glu Ile Lys Asp Thr Lys Glu Ala
    1090                1095                1100

Leu Asp Lys Ile Glu Glu Glu Gln Asn Lys Ser Lys Lys Lys Ala Gln
1105                1110                1115                1120

Gln Ala Ala Ala Asp Thr Gly His Ser Asn Gln Val Ser Gln Asn Tyr
                1125                1130                1135
```